US012104206B2

(12) United States Patent
Thompson et al.

(10) Patent No.: US 12,104,206 B2
(45) Date of Patent: Oct. 1, 2024

(54) METHOD OF DIRECT TARGET SEQUENCING USING NUCLEASE PROTECTION

(71) Applicant: HTG Molecular Diagnostics, Inc., Tucson, AZ (US)

(72) Inventors: Debrah Thompson, Tucson, AZ (US); Matthew Rounseville, Tucson, AZ (US)

(73) Assignee: HTG Molecular Diagnostics, Inc., Tucson, AZ (US)

( * ) Notice: Subject to any disclaimer, the term of this patent is extended or adjusted under 35 U.S.C. 154(b) by 789 days.

(21) Appl. No.: 16/070,678

(22) PCT Filed: Feb. 10, 2017

(86) PCT No.: PCT/US2017/017512
§ 371 (c)(1),
(2) Date: Jul. 17, 2018

(87) PCT Pub. No.: WO2017/139672
PCT Pub. Date: Aug. 17, 2017

(65) Prior Publication Data
US 2019/0017112 A1    Jan. 17, 2019

Related U.S. Application Data

(60) Provisional application No. 62/294,143, filed on Feb. 11, 2016, provisional application No. 62/435,459, filed on Dec. 16, 2016.

(51) Int. Cl.
*C12Q 1/6806* (2018.01)
*C12Q 1/6869* (2018.01)

(52) U.S. Cl.
CPC ......... *C12Q 1/6869* (2013.01); *C12Q 1/6806* (2013.01)

(58) Field of Classification Search
None
See application file for complete search history.

(56) References Cited

U.S. PATENT DOCUMENTS

| | | | | |
|---|---|---|---|---|
| 4,035,234 A | * | 7/1977 | Schutt ................ | C07K 14/8117 435/268 |
| 4,177,038 A | * | 12/1979 | Biebricher et al. ......................... | C08G 18/3893 210/198.2 |
| 4,652,525 A | * | 3/1987 | Rutter et al. .......... | C07K 14/62 435/252.33 |
| 4,879,214 A | * | 11/1989 | Kornher et al. ..... | C12Q 1/6816 435/6.18 |
| 4,885,237 A | * | 12/1989 | Evans ..................... | C12Q 1/68 435/6.11 |
| 5,349,123 A | * | 9/1994 | Shewmaker et al. .... | A01H 1/00 435/412 |
| 8,741,564 B2 | * | 6/2014 | Seligmann et al. . | C12Q 1/6853 435/6.1 |
| 2006/0223122 A1 | * | 10/2006 | Fogo et al. ......... | G01N 33/6851 435/7.2 |
| 2006/0223197 A1 | * | 10/2006 | Vielsack et al. ..... | G01N 33/533 436/524 |
| 2006/0234234 A1 | * | 10/2006 | Van Dongen et al. ...................... | C12Q 1/6886 435/6.12 |
| 2006/0246453 A1 | * | 11/2006 | Kato et al. ......... | C12N 15/1096 435/6.11 |
| 2008/0199916 A1 | | 8/2008 | Zheng et al. | |
| 2008/0268451 A1 | | 10/2008 | Seligmann et al. | |
| 2010/0062436 A1 | | 3/2010 | Jarosch et al. | |
| 2011/0104693 A1 | | 5/2011 | Seligmann | |
| 2012/0115744 A1 | | 3/2012 | Raymond | |
| 2013/0035248 A1 | * | 2/2013 | Icenhour .............. | C12Q 1/6895 506/9 |
| 2013/0040344 A1 | * | 2/2013 | Ju ........................ | C12Q 1/6853 435/91.21 |
| 2013/0040843 A1 | * | 2/2013 | Von Toerne et al. .. | C12Q 1/686 506/9 |
| 2013/0040847 A1 | * | 2/2013 | Thrippleton et al. ....................... | C12Q 1/6841 506/9 |
| 2014/0357515 A1 | | 12/2014 | Friedrich et al. | |

FOREIGN PATENT DOCUMENTS

| | | |
|---|---|---|
| JP | 2006-501842 | 1/2006 |
| JP | 2008-504842 | 2/2008 |
| JP | 2013-520980 | 6/2013 |
| JP | 2014-512838 | 5/2014 |
| WO | WO 2004/087916 | 10/2004 |
| WO | WO 2006/007567 A2 | 1/2006 |
| WO | WO 2008/121927 A1 | 10/2008 |
| WO | WO 2010/117817 A2 | 10/2010 |
| WO | WO 2011/056863 A1 | 5/2011 |
| WO | WO 2012/151111 | 11/2012 |
| WO | WO 2013/087630 A1 | 6/2013 |

(Continued)

OTHER PUBLICATIONS

Zhu et al., "A Novel Coronavirus from Patients with Pneumonia in China, 2019", The New England Journal of Medicine</i>, 328, 8, pp. 727-733, Feb. 20, 2020. (Year: 2020).*
Zhu et al., "A Novel Coronavirus from Patients with Pneumonia in China, 2019", The New England Journal of Medicine, 328, 8, Feb. 20, 2020, pp. 727-733. (Year: 2020).*
"Science Brief: Emerging SARS-COV-2 Variants", Centers for Disease Control and Prevention, Jan. 28, 2021, pp. 1-4. (Year: 2021).*
Gabbatiss et al., "New form of DNA discovered inside living human cells", The Independent, accessed Apr. 24, 2018. (2018).*

(Continued)

*Primary Examiner* — Bradley L. Sisson
(74) *Attorney, Agent, or Firm* — Klarquist Sparkman, LLP

(57) ABSTRACT

The present disclosure provides methods and kits for direct sequencing of nucleic acid targets. Such methods can be used to determine if one or more nucleic acid targets are present in a sample.

29 Claims, 20 Drawing Sheets
Specification includes a Sequence Listing.

(56) References Cited

FOREIGN PATENT DOCUMENTS

WO    WO 2014/093330    6/2014

OTHER PUBLICATIONS

Stratagene Catalog p. 39 (1988).*
PCT/US2017/017512 International Search Report and Written Opinion mailed on May 15, 2017 (10 pages).
Notice of Reasons for Rejection mailed in Japanese Patent Application No. 2018-541683, mailed on Oct. 7, 2020, 3 pages (with English translation, 7 pages).

* cited by examiner

Capture at hybridization:

Post-nuclease capture:

Post-Hybridization capture:

One CFS embodiments
(CFS on the 3' end or the 5' end of the Target)

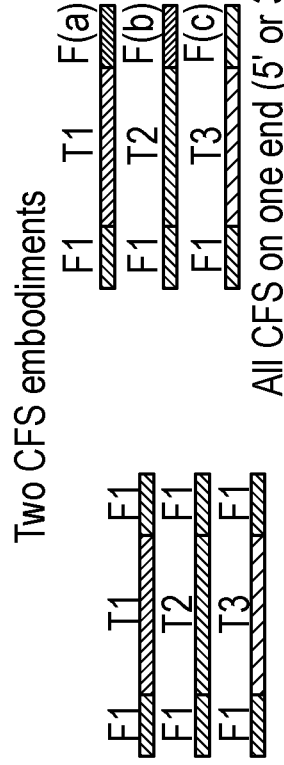

Two CFS embodiments

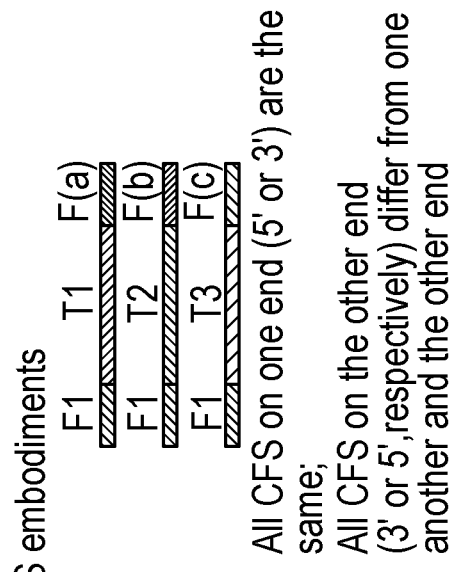

FIG. 6C
All 5' and 3' CFSs the same

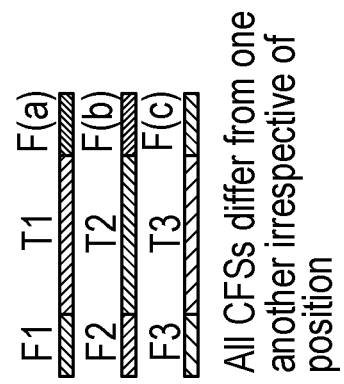

FIG. 6E
All CFS on one end (5' or 3') are the same;
All CFS on the other end (3' or 5', respectively) differ from one another and the other end

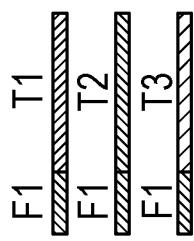

FIG. 6D
All CFSs on each end are the same;
But 5CFS differs from 3CFS

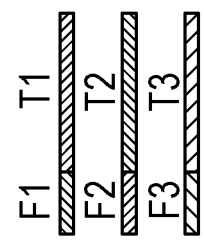

FIG. 6F
All CFSs differ from one another irrespective of position

Targets also may be tagged (either similarly or differentially) on either or both the 5' or 3' end using tagged primers in subsequent amplification step(s)

| | |
|---|---|
| EGFR Exon19 | p.E746_A750del<br>p.L747_T751del<br>p.L747_S752del<br>p.L747_P753del<br>p.E746_T751del<br>p.L747_E749del<br>p.L747_A750del<br>p.E746_E749del<br>p.E746_S752del<br>E746 - T751 del I ins<br>E746 - A750 del V ins<br>2248 G>C L747 - E749 del P ins<br>2251 A>C L747 - T750 del P ins<br>L747 - S752 del Q ins<br>L748 - S752 del S ins<br>E746 - T 751 del V ins |
| EGFR Exon20 | ASV770-772 ins<br>H774 ins<br>G771 ins<br>CV770-771 ins<br>NP773-744 ins H775Y<br>PH774-775 ins<br>NPH774-776 ins<br>HV775-776 ins |

| | |
|---|---|
| BRAF | V600wt<br>V600E<br>V600K<br>V600R<br>V600E2<br>V600D |
| KRAS | G12wt<br>G12D<br>G12V<br>G12A<br>G12C<br>G12S<br>G12R<br>G13D |
| KRAS | Q61wt<br>Q61E<br>Q61R<br>Q61L<br>Q61H-C<br>Q61H-T |
| EGFR | T790M<br>L858R<br>D761Y<br>G719A<br>G719S<br>G719C |

FIG. 9

```
BRAF V600 NPPF        TGATGGGACCCGCUCCATCGAGATTCACTGTAGCUAGACCAAAATCACC

BRAF V600wt  target   TGATGGGACCCACTCCATCGAGATTCACTGTAGCTAGACCAAAATCACC
BRAF V600E   target   TGATGGGACCCACTCCATCGAGATTCTCTGTAGCTAGACCAAAATCACC
BRAF V600K   target   TGATGGGACCCACTCCATCGAGATTCTTTGTAGCTAGACCAAAATCACC
BRAF V600R   target   TGATGGGACCCACTCCATCGAGATTCCTGTAGCTAGACCAAAATCACC
BRAF V600E2  target   TGATGGGACCCACTCCATCGAGATTTTCTGTAGCTAGACCAAAATCACC
BRAF V600D   target   TGATGGGACCCACTCCATCGAGATTATCTGTAGCTAGACCAAAATCACC

KRAS G12 NPPF         TGTATCGTCAAGGCGCUCUUGCCTACGCCACCAGCUCCAACTACCACAAG

KRAS G12wt   target   TGTATCGTCAAGGCACTCUUGCCTACGCCACCAGCUCCAACTACCACAAG
KRAS G12D    target   TGTATCGTCAAGGCACUCUUGCCTACGCCACCATCAGCUCCAACTACCACAAG
KRAS G12V    target   TGTATCGTCAAGGCACUCUUGCCTACGCCACCAACAGCUCCAACTACCACAAG
KRAS G12A    target   TGTATCGTCAAGGCACUCUUGCCTACGCCACCAGCAGCUCCAACTACCACAAG
KRAS G12C    target   TGTATCGTCAAGGCACUCUUGCCTACGCCACCAAGCUCCAAGCUCCAACTACCACAAG
KRAS G12S    target   TGTATCGTCAAGGCACUCUUGCCTACGCCACCACTAGCUCCAACTACCACAAG
KRAS G12R    target   TGTATCGTCAAGGCACUCUUGCCTACGCCACCAGAGCUCCAACTACCACAAG
KRAS G13D    target   TGTATCGTCAAGGCACUCUUGCCTACGCCACCTCACCAGCUCCAACTACCACAAG

KRAS Q61 NPPF         GGTCCCTCATTGTACUGTACTCCTCTTGACCTGCTGUGTCGAGAATATCC

KRAS Q61wt   target   GGTCCCTCATTGCACTGTACTCCTCTTGACCTGCTGTGTCGAGAATATCC
KRAS Q61E    target   GGTCCCTCATTGCACTGTACTCCTCTTCACCTGCTGTGTCGAGAATATCC
KRAS Q61R    target   GGTCCCTCATTGCACTGTACTCCTCTTGACCTGCTGTGTCGAGAATATCC
KRAS Q61L    target   GGTCCCTCATTGCACTGTACTCCTCTCGACCTGCTGTGTCGAGAATATCC
KRAS Q61H-C  target   GGTCCCTCATTGCACTGTACTCCTCCTGTGACCTGCTGTGTCGAGAATATCC
KRAS Q61H-T  target   GGTCCCTCATTGCACTGTACTCCTCATGACCTGCTGTGTCGAGAATATCC
```

(note that only the target(s)-complementary portion of the NPPF complementary is displayed)
(all target sequences are shown reverse-complemented for ease of comparison to NPPE sequence)

FIG. 10

| Target detected / Amplicon concentration in sample | BRAF_V600wt | BRAF_V600E | KRAS_Q61wt | KRAS_Q61HC |
|---|---|---|---|---|
| 100 fM | 44063 +/- 1838 (4.2% CV) | 50011 +/- 2244 (4.5% CV) | 26855 +/- 1862 (6.9% CV) | 32994 +/- 2400 (7.3% CV) |
| 31.6 fM | 14081 +/- 489 (3.5% CV) | 16264 +/- 961 (5.9% CV) | 9215 +/- 751 (8.2% CV) | 11520 +/- 704 (6.1% CV) |
| 10 fM | 6067 +/- 243 (4.0% CV) | 7109 +/- 700 (9.8% CV) | 3880 +/- 492 12.7% CV) | 4871 +/- 501 (10.3% CV) |
| 3.16 fM | 1443 +/- 112 (7.8% CV) | 1663 +/- 86 (5.2% CV) | 892 +/- 90 (10.1% CV) | 1184 +/- 95 (8.0% CV) |
| 1 fM | 398 +/- 52 (13.1% CV) | 459 +/- 34 (7.5% CV) | 285 +/- 38 (13.3% CV) | 350 +/- 18 (5.1% CV) |
| 316 aM | 189 +/- 26 (13.5% CV) | 217 +/- 39 (18.2% CV) | 126 +/- 16 (12.8% CV) | 172 +/- 24 (14.0% CV) |
| 100 aM | 61 +/- 11 (18.6% CV) | 56 +/- 16 (28.9% CV) | 45 +/- 6 (14.3% CV) | 40 +/- 18 (46.0% CV) |

FIG. 14

METHOD OF DIRECT TARGET SEQUENCING USING NUCLEASE PROTECTION

CROSS-REFERENCE TO RELATED APPLICATIONS

This is the U.S. National Stage of International Application No. PCT/US2017/017512 filed Feb. 10, 2017, which was published in English under PCT Article 21 (2), which in turn claims priority to U.S. Provisional Application No. 62/294,143 filed Feb. 11, 2016 and U.S. Provisional Application No. 62/435,459 filed Dec. 16, 2016, both herein incorporated by reference.

FIELD

The present disclosure provides quantitative nuclease protection sequencing (qNPS) methods, and kits, that allow for direct sequencing of nucleic acid targets. Such methods can be used to determine if one or more nucleic acid targets are present in a sample.

BACKGROUND

Although methods of sequencing nucleic acid molecules are known, there is still a need for methods that permit direct sequencing analysis of multiple samples or multiple sequences simultaneously or contemporaneously. Methods of direct multiplexing nucleic acid molecule sequencing reactions have not been realized at the most desired performance or simplicity levels.

SUMMARY

Methods are provided that improve prior quantitative nuclease protection sequencing (qNPS) methods (such as those disclosed in U.S. Publication No. US 2011-0104693 and U.S. Pat. No. 8,741,564) and represent an improvement to current nucleic acid sequencing methods. In some examples, the disclosed methods are used to sequence several different target nucleic acid molecules in a sample using a plurality of nuclease protection probes with a flanking sequence (NPPFs), wherein each NPPF specifically binds to one or more particular target nucleic acid molecules. In some examples, the disclosed methods are used to sequence at least one target nucleic acid molecule in a plurality of samples simultaneously.

The disclosed methods of determining a sequence of at least one target nucleic acid molecule in a sample can include contacting the sample with at least one NPPF under conditions sufficient for the NPPF to specifically bind to the target nucleic acid molecule. The NPPF includes a sequence that is complementary to all or a portion of the target nucleic acid molecule, thus permitting specific binding or hybridization between the target nucleic acid molecule and the NPPF. For example, the region of the NPPF that is complementary to a region of the target nucleic acid molecule binds to or hybridizes to that region of the target nucleic acid molecule with high specificity. The NPPFs further include one or more flanking sequences at the 5'-end and/or 3'-end of the NPPF. Thus, the one or more flanking sequences are located 5', 3', or both, to the sequence complementary to the target nucleic acid molecule. If the NPPF includes a flanking sequence at both the 5'-end and 3'-end, in some examples the sequence of each NPPF is different and not complementary. The flanking sequence(s) includes several contiguous nucleotides having a sequence (such as a sequence of at least 12 nucleotides) not found in a nucleic acid molecule present in the sample. In some examples, the NPPF (for example in one or both flanking sequences and/or the sequence of the region complementary to all or a portion of the target nucleic acid molecule) includes one or more dUTPs, to permit later degradation of the NPPF (for example using uracil DNA deglycosylase). In one example, the NPPF (for example in one or both flanking sequences and/or the sequence of the region complementary to all or a portion of the target nucleic acid molecule) can include dUTPs at a position that would otherwise be a dTTP.

In some examples, the NPPF (such as a flanking sequence or the region of the NPPF that is complementary to a region of the target nucleic acid molecule) includes a single nucleotide mismatch (such as replacing an A with a G, or a C with a T, such that an A:T base pair becomes a G:T base pair, or a C:G base pair becomes a T:G base pair; or when the target nucleic acid is an RNA, an A:rU base pair would become a G:rU base pair, or C:rG base pair becomes a T:rG base pair), which does not adversely affect the ability of the NPPF to hybridize to the target nucleic acid molecule with high specificity, and which is not typically recognized or cleaved by single stranded nucleases such as S1 nuclease. The region of the NPPF that is complementary to a region of the target nucleic acid molecule is therefore unique and can be distinguished from target nucleic acid sequences in the sample. For example, the presence of the mismatched nucleotide can allow one to determine if what is being detected (e.g., sequenced) is an NPPF or the target nucleic acid molecule. In some examples, the mismatched nucleotide is not present at the very 5'-end or very 3'-end of the NPPF, such as not within two bases of the 5'-end or 3'-end of the NPPF. In some examples, the mismatched nucleotide is not present at the junction between a flanking sequence and the region of the NPPF that is complementary to a region of the target nucleic acid molecule, for example is about 10 to 15 bases from such a junction. In some examples, the mismatched nucleotide is within the region complementary to the target, such as not within two bases of the junction between flanking sequence and the sequence complementary to the target within the NPPF. In one example, the mismatched nucleotide is about 10-15 nucleotides within the sequence complementary to the target, such as 12 nucleotides within the region complementary to the target.

The methods also include contacting the sample with a nucleic acid molecule having complementarity to the flanking sequence (CFS) of the NPPF. For example, if the NPPF has a 5'-flanking sequence, the sample is contacted with a nucleic acid molecule having sequence complementarity to the 5'-flanking sequence (5CFS) and a 5'-end phosphate, under conditions sufficient for the 5'-flanking sequence to specifically bind to the 5CFS. Similarly, if the NPPF has a 3'-flanking sequence, the sample is contacted with a nucleic acid molecule having sequence complementarity to the 3'-flanking sequence (3CFS) under conditions sufficient for the 3'-flanking sequence to specifically bind to the 3CFS. In some examples, at least one of the 3CFS and the 5CFS includes a capture moiety that permits capture or isolation of a target nucleic acid molecule. In some examples, the NPPF includes a capture moiety that permits capture or isolation of a target nucleic acid molecule. This hybridization results in the generation of a double-stranded (ds) nucleic acid molecule, with the NPPF hybridized to the target nucleic acid molecule, and to the 5CFS and/or 3CFS.

The methods also include contacting the sample with a nuclease specific for single-stranded (ss) nucleic acid molecules under conditions sufficient to degrade or remove unbound ss nucleic acid molecules in the reaction. Thus for example, NPPFs that have not bound target nucleic acid molecule or CFSs, as well as unbound target nucleic acid molecules or unbound portions of target nucleic acid molecules, other ss nucleic acid molecules in the sample, and unbound CFSs, are degraded. This results in a digested sample that includes an NPPF hybridized to its target nucleic acid molecule, hybridized to its corresponding 3CFS, hybridized to its corresponding 5CFS, or hybridized to both its corresponding 3CFS and its corresponding 5CFS. This ds nucleic acid molecule is captured (e.g., separated from other nucleic acid molecules in the sample, for example by use of the capture moiety, such as by immobilizing the ds nucleic acid molecule to a solid support and washing away the rest of the sample). Capture of the target nucleic acid molecule can occur any time (e.g., at any step) prior to the ligation (e.g., the complex that includes the NPPF hybridized to the target and CFS(s) can be captured or retrieved during hybridization, following hybridization, or after nuclease digestion).

Subsequently, the CFS(s) is/are ligated to the target nucleic acid, for example the 5'-phosphate of the 5CFS is ligated to the 3'-end of the target nucleic acid molecule, and the 3'-end of the 3CFS is ligated to the 5'-end of the target nucleic acid molecule, thereby generating a ligated target nucleic acid molecule (referred to herein as a ligated target). In some examples, in addition to ligation, a polymerization step is performed (for example simultaneously with the ligation, or following ligation). For example, polymerase can be used to replace nucleotides of the CFS(s) or the target that were inadvertently removed by the nuclease (i.e., via the propensity of ss-specific nucleases to "nibble" bases at the exposed ends of double-stranded nucleic acids). The double-stranded NPPF: ligated target nucleic acid molecule is separated into its corresponding ss nucleic acid molecules, thereby generating a mixture of ss NPPFs and ss ligated target nucleic acid molecules. In some examples, separation of the double-stranded NPPF: ligated target into its corresponding ss nucleic acid molecules includes treatment with a DNase, for example if the target molecule is RNA, the NPPF is DNA, and the 3CFS and 5 CFS are RNA. In such an example, the ss NPPFs are degraded, digested, separated from the ss ligated RNA target molecules, or combinations thereof. In some examples the ss ligated RNA target molecule is converted to complementary DNA (cDNA) by use of reverse transcriptase. In one example, an RNA strand of the NPPF: ligated target can be selectively removed by treating the complex with RNase H, which selectively removes the RNA moiety of a DNA: RNA complex (for example, if the if the target molecule is DNA, the NPPF is RNA, and the 3CFS and 5 CFS are DNA). Alternative nucleases can be used to degrade DNA separately from RNA or RNA separately from DNA. The ligated target nucleic acid molecules are optionally captured (e.g., separated from other nucleic acid molecules, for example by use of the capture moiety, such as by immobilizing the ligated target nucleic acid molecules to the bottom of a tube and washing away undesired other molecules) or otherwise separated from the ss NPPFs, for example by use of the capture moiety on the NPPF, 5CFS or 3CFS. The ligated target nucleic acid molecules are optionally amplified (for example to add an experiment tag and/or sequence adaptor). At least a portion of the ss ligated target nucleic acid molecule (or amplicon thereof) is sequenced, thereby determining the sequence of the at least one target nucleic acid molecule in the sample.

Also described herein are kits that can be used to directly sequence one or more target nucleic acid molecules.

The foregoing and other objects and features of the disclosure will become more apparent from the following detailed description, which proceeds with reference to the accompanying figures.

BRIEF DESCRIPTION OF THE DRAWINGS

FIG. 2B shows that capture 320 of one or more target nucleic acid molecules (e.g., 200 in FIG. 2A, such as 214 in FIG. 2A) can occur during hybridization 310. FIG. 2C shows that capture 420 of a target can occur following nuclease digestion 430. FIG. 2D shows that capture 520 of a target can occur following hybridization 510.

FIGS. 6A-F are schematic drawings showing exemplary embodiments of ligated target molecules, including embodiments with (A and B) a CFS only on one end of the ligated target or (C-F) with CFSs on both ends of the ligated target.

FIG. 9 provides examples of genes, each with numerous different mutations, which can be detected (for example simultaneously or in the same reaction) with the disclosed methods. In some examples, the wild type version of the gene, and at least two different mutations of the gene (such as 2, 3, 4, 5, 6, 7, 8, 9 or 10 different mutations), are detected with a single NPPF (e.g., see FIG. 10).

FIG. 10 provides exemplary probes (shown is the region of the NPPF that is complementary to a region of the target nucleic acid molecule, that is, the flanking sequences are not shown) (SEQ ID NOS: 1, 8 and 17), each of which can detect a plurality of different point mutations (see red nucleotides) was well as the wild type gene. The target sequences shown below the NPPF sequence are not the strand to which the NPPF will hybridize, but are instead the opposite strand, so that the changes made to the NPPF sequence relative to the target to be identified are illustrated. Note that the NPPF sequence is unique; it does not share 100% sequence identity to either the wild type or mutant sequence. SEQ ID NOS: 1-23 from top to bottom. The mismatched nucleotide in each NPPF is italicized (blue).

FIG. 14 is a table showing the ability of the disclosed methods to discern single nucleotide variations in a dilution series; average, standard deviation, and % CV for each of the four detected targets is displayed.

SEQUENCE LISTING

Figure 1A:
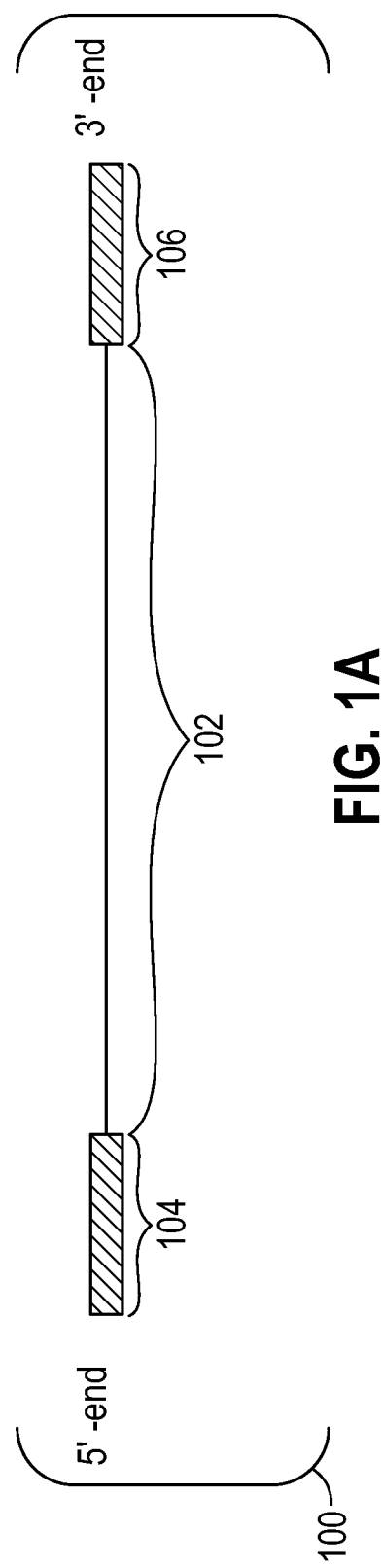
FIG. 1A is a schematic diagram showing an exemplary nuclease protection probe having flanking sequences (NPPF), 100. The NPPF 100 includes a region 102 having a sequence that specifically binds to/hybridizes to a target nucleic acid sequence. The NPPF also includes a 5'-flanking sequence 104, a 3'-flanking sequence 106, or both (the embodiment with both is shown).

The nucleic acid and protein sequences are shown using standard letter abbreviations for nucleotide bases as defined in 37 C.F.R. 1.822. Only one strand of each nucleic acid sequence is shown, but the complementary strand is understood as included by any reference to the displayed strand. The contents of the text file named "seq listing" which was created on Feb. 9, 2017 and is 16 KB in size, are hereby incorporated by reference in their entirety.

SEQ ID NO: 1 shows an NPPF nucleic acid sequence that can detect a plurality of BRAF coding sequences at amino acid 600.

SEQ ID NO: 2 shows a portion of wild type human BRAF sequence.

SEQ ID NO: 3 shows a portion of BRAF sequence that codes for a V600E mutation.

SEQ ID NO: 4 shows a portion of BRAF sequence that codes for a V600K mutation.

SEQ ID NO: 5 shows a portion of BRAF sequence that codes for a V600R mutation.

SEQ ID NO: 6 shows a portion of BRAF sequence that codes for a V600E2 mutation.

SEQ ID NO: 7 shows a portion of BRAF sequence that codes for a V600D mutation.

SEQ ID NO: 8 shows an NPPF nucleic acid sequence that can detect a plurality of KRAS coding sequences at amino acid 12.

SEQ ID NO: 9 shows a portion of wild type human KRAS sequence.

SEQ ID NO: 10 shows a portion of KRAS sequence that codes for a G12D mutation.

SEQ ID NO: 11 shows a portion of KRAS sequence that codes for a G12V mutation.

SEQ ID NO: 12 shows a portion of KRAS sequence that codes for a G12A mutation.

SEQ ID NO: 13 shows a portion of KRAS sequence that codes for a G12C mutation.

SEQ ID NO: 14 shows a portion of KRAS sequence that codes for a G12S mutation.

SEQ ID NO: 15 shows a portion of KRAS sequence that codes for a G12R mutation.

SEQ ID NO: 16 shows a portion of KRAS sequence that codes for a G13D mutation.

SEQ ID NO: 17 shows an NPPF nucleic acid sequence that can detect a plurality of KRAS coding sequences at amino acid 61.

SEQ ID NO: 18 shows a portion of wild type human KRAS sequence.

SEQ ID NO: 19 shows a portion of KRAS sequence that codes for a Q61E mutation.

SEQ ID NO: 20 shows a portion of KRAS sequence that codes for a Q61R mutation.

SEQ ID NO: 21 shows a portion of KRAS sequence that codes for a Q61L mutation.

SEQ ID NO: 22 shows a portion of KRAS sequence that codes for a Q61H-C mutation.

SEQ ID NO: 23 shows a portion of KRAS sequence that codes for a Q61H-T mutation.

SEQ ID NO: 24 shows a 5'-flanking sequence of an NPPF.

SEQ ID NO: 25 shows a 3'-flanking sequence of an NPPF.

SEQ ID NO: 26 shows a forward primer sequence with a region of eight nucleotides that can be used to include an experimental tag (such as SEQ ID NO: 28, 29, 36, 37, 38, 39, 40, 50, 51, or 54).

SEQ ID NO: 27 shows a reverse primer sequence with a region of six nucleotides that can be used to include an experimental tag (such as SEQ ID NO: 30, 31, 32, 33, 34, 35, 41, 42, 43, 44, 45, 46, 47, 48, 49, 52, 53, 55, 56, 57, 58, 59, 60 or 61).

SEQ ID NOS: 28 to 61 show exemplary experimental tag sequences.

SEQ ID NO: 62 shows a portion of target wild type human BRAF sequence.

SEQ ID NO: 63 shows a portion of target BRAF sequence that codes for a V600E mutation.

SEQ ID NO: 64 shows a portion of target BRAF sequence that codes for a V600E2 mutation.

DETAILED DESCRIPTION

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The singular forms "a," "an," and "the" refer to one or more than one, unless the context clearly dictates otherwise. For example, the term "comprising an NPPF" includes single or plural NPPFs and is considered equivalent to the phrase "comprising at least one NPPF." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety, as are the GENBANK® Accession numbers (for the sequence present on Feb. 11, 2016). In case of conflict, the present specification, including explanations of terms, will control. In addition, the materials, methods, and examples are illustrative only and not intended to be limiting.

Except as otherwise noted, the methods and techniques of the present disclosure are generally performed according to conventional methods well known in the art and as described in various general and more specific references that are cited and discussed throughout the present specification. See, e.g., Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

I. Overview

The present disclosure provides methods that allow for direct sequencing of a target nucleic acid molecule, which methods further can be multiplexed (e.g., detecting a plurality of targets in a single sample) or are amenable to high-throughput (e.g., detecting a target in a plurality of samples) or are multiplexed and high-throughput (e.g., detecting a plurality of targets in a plurality of samples). The disclosed methods provide several improvements over currently available sequencing methods. For example, because the methods directly sequence the target nucleic acid molecule of interest (or an amplicon thereof), instead of using a surrogate, the detection of the target (such as a point mutation) can be more accurate. In addition, because the disclosed methods are targeted, the data analysis is simplified, because, for example, the sequencer output can be aligned against a relatively small database of the applicable NPPF sequence(s) (or the complement of the applicable NPPF sequence(s)), which avoids the need to align sequencer output against a complex nucleic acid database (such as, a complete genome) and assembly of sequenced fragments to identify the target. Long reads of nucleotides also are not required because, for example, the ligated targets being sequenced consist of relatively few nucleotides (compared, e.g., to an intact mRNA encoding the same target) and only a sufficient number of nucleotides of a ligated target must be read (often less than the full ligated target sequence) to enable successful alignment against the relatively simple reference database (discussed above). Further, some sequencers restrict the number of nucleotides that can be "read" in a single sequencing run; by reducing the number of nucleotides that must be read in order to identify the target(s) of interest, more useful data may be obtained from each sequencing run. In addition, the results can be simply counted, without the need for complicated bioinformatics analysis. In addition, because the methods require less processing of the target nucleic acid molecules, bias introduced by such processing can be reduced or eliminated. For example, in some current methods, for example when the target is an RNA (such as mRNA and/or miRNA), methods typically employ steps to isolate or extract the RNA from a sample, subject it to RT-PCR, ligate the RNA, or combinations thereof. Prior methods may also require a depletion or a separation step to remove undesired nucleic acid molecules, such as tRNA and/or rRNA. In some embodiments of the disclosed methods, such steps are not required. As a result, the methods permit one to analyze a range of sample types not otherwise amenable to detection sequencing. In addition, this results in less loss of the RNA from the sample, providing a more accurate result.

The methods can be used to detect DNA or RNA, mutations such as one or more gene fusions, insertions or deletions, tandem repeats, single nucleotide polymorphisms (SNPs), single nucleotide variants, and DNA methylation status. In one example the methods are used to detect a point mutation in a target nucleic acid molecule. Such a mutation can be a known mutation, or a mutation that is newly discovered using the disclosed methods. For example, the methods can be used to detect one or more point mutations (such as at least 2, at least 3, at least 4, at least 5, at least 6, at least 7, at least 8, at least 9, at least 10 or more point mutations, such as 1, 2, 3, 4, 5, 6, 7, 8, 9, 10 different point mutations) in a single target nucleic acid molecule or in multiple target nucleic acid molecules. In some examples, each different point mutation is considered a different target nucleic acid molecule (e.g., FIG. 10 shows that SEQ ID NO: 1 can be used to detect six different target nucleic acid molecules (SEQ ID NOS: 2-7), including the wild type BRAF gene and five different mutants thereof). In some examples, the methods can be used to detect one or more point mutations in two or more different target nucleic acid molecules. The method uses a nucleic acid probe, referred to herein as a nuclease protection probe comprising a flanking sequence (NPPF), as well as complementary flanking sequences (CFSs). The use of NPPFs and CFSs permits multiplexing, and in some examples roughly conserves the stoichiometry of the sequenced target nucleic acid molecule, because the CFSs permit universal primer binding sites for amplification and permit addition of sequencing adaptors and experimental tags (at either the 3'- or the 5'-end, or at both ends for example to increase multiplexing), without significantly altering the stoichiometry. As the CFSs can be universal, the same primers can be used to amplify any target nucleic acid molecule to which the CFSs is ligated, thus allowing for multiplexing and in some examples roughly conserving stoichiometry.

In addition, the primers (which hybridize to the CFSs) permit addition of tags to the target nucleic acid molecule to which the CFSs are ultimately ligated to (such as experiment tags to permit the identification of the target without necessitating the sequencing of the entire target itself or to permit samples from different patients or different experiments or otherwise to be combined into a single sequencing run, at either the 3'- or the 5'-end, or at both ends for example to increase multiplexing, as well as sequencing adaptors to permit attachment of a sequence needed for a particular sequencing platform and formation of colonies for some sequencing platforms). The use of NPPFs and CFSs also simplifies the complexity of the sequencer input (also called the sequencing library) that is analyzed (e.g., sequenced), as the sequencing library contains a known portion of the target of interest (or ligated target amplicons) rather than whole targets (or many fragments of whole targets). As the NPPF is ultimately disassociated (e.g., digested, cleaved, separated, or any combination thereof) from the ligated target, it is the ligated target (or amplicons thereof), not the NPPF as a surrogate, that is ultimately sequenced. The sequencing of ligated targets (or amplicons of ligated targets) simplifies data analysis compared to that required for other sequencing methods, reducing the algorithm to simply count the ligated targets sequenced, rather than having to match sequences to the genome and deconvolute the multiple sequences/gene that are obtained from standard methods of sequencing.

In one example, the disclosure provides methods for sequencing at least one target nucleic acid molecule in a sample (such as at least 2, at least 3, at least 4, at least 5, at least 10, at least 20, at least 30, at least 40, at least 50, at least 100, at least 500, at least 1000, at least 2000, or at least 3000 target nucleic acid molecules). In some examples, the sample, such as a sample including nucleic acids (such as DNAs and/or RNAs) is heated to denature nucleic acid molecules in the sample, for example to permit subsequent hybridization between the NPPF and the target nucleic acid molecules in the sample as well as hybridization between the NPPF and its corresponding CFS(s). In some examples, the sample is a lysed sample (and thus in some examples the methods include lysing the sample). In some examples, the sample is a fixed sample (such as a paraffin-embedded formalin-fixed (FFPE) sample, hematoxylin and eosin stained tissues, or glutaraldehyde fixed tissues). For example, the target nucleic acid molecules can be fixed, cross-linked, or insoluble.

In some examples, the disclosed methods sequence at least one target nucleic acid molecule (such as at least two different target nucleic acid molecules) in a plurality of samples simultaneously or contemporaneously. Simultaneous sequencing refers to sequencing that occurs at the same time or substantially the same time and/or occurring in the same sequencing library or the same sequencing reaction or performed on the same sequencing flowcell or semiconductor chip (for example, contemporaneous). In some examples, the events occur within 1 microsecond to 120 seconds of one another (for example within 0.5 to 120 seconds, 1 to 60 seconds, or 1 to 30 seconds, or 1 to 10 seconds). In some examples, the disclosed methods sequence two or more target nucleic acid molecules in a sample (for example simultaneously or contemporaneously), for example using (i) at least two different NPPFs, each NPPF specific for a different target nucleic acid molecule, (ii) by using one NPPF specific for a plurality of different target nucleic acid molecules (e.g., FIG. 10 shows that SEQ ID NO: 1 (which is the part of the NPPF that is complementary to a region of the target nucleic acid molecule) can be used to detect six different target nucleic acid molecules (SEQ ID NOS: 2-7), including the wild type BRAF gene and five different BRAF mutants; similar examples are given for KRAS), or (iii) combinations thereof. In one example, the sample is contacted with a plurality of NPPFs (such as at least 2, 3, 4, 5, 10, 15, 20, 25, 50, 75, 100, 200, 300, 500, 1000, 2000, 3000, 4000, 5000, or more), wherein each NPPF specifically binds to a particular target nucleic acid molecule. For example, if there are 10 target nucleic acid molecules, the sample can be contacted with 10 different NPPFs each specific for one of the 10 targets. However, in some examples, the sample is contacted with at least one NPPF (such as at least 2, 3, 4, 5, 10, 15, 20, 25, 50, 75, 100, 200, 300, 500, 1000, 2000, 3000, 4000, 5000, or more), wherein each NPPF specifically binds to at least two (such as at least 2, 3, 4, 5, 6, 7, 8, 9, 10, or more) different target nucleic acid molecules (such as a wild type gene and one or more mutations of the wild type gene). In some examples, the sample is contacted with one or more NPPFs that each specifically bind to a particular target nucleic acid molecule, and contacted with one or more NPPFs that each specifically bind to at least two different target nucleic acid molecules (such as a wild type gene and one or more mutations of the wild type gene, e.g., see FIG. 10). In one example, at least one NPPF is specific for a miRNA target nucleic acid molecule and at least one NPPF is specific for an mRNA target nucleic acid molecule. In some examples, at least 10 different NPPFs are incubated with the sample. However, it is appreciated that in some examples, more than one NPPF (such as 2, 3, 4, 5, 10, 20, or more) specific for a single target nucleic acid molecule can be used, such as a population of NPPFs that are specific for different regions of the same target nucleic acid, or a population of NPPFs that can bind to the target nucleic acid and variations thereof (such as those having mutations or polymorphisms). For example, a low expressed nucleic acid target may have more NPPFs that hybridize to it relative to a nucleic acid target expressed at a higher level, such as four NPPFs hybridizing to a low expressed nucleic acid target and a single NPPF hybridizing to a high expressed nucleic acid target. Thus, a population of NPPFs can include at least two different NPPF populations (such as 2, 3, 4, 5, 10, 20, or 50 different NPPF sequences), wherein each NPPF population (or sequence) specifically binds to a different target nucleic acid molecule.

The methods include contacting the sample with at least one nuclease protection probe comprising a flanking sequence (NPPF) under conditions sufficient for the NPPF to specifically bind to or hybridize to the target nucleic acid molecule. Hybridization is the process that occurs wherein there is a sufficient degree of complementarity between two nucleic acid molecules such that stable and specific binding (e.g., base pairing) occurs between the first (e.g., an NPPF) and the second nucleic acid molecule (e.g., the nucleic acid target and the CFSs). The NPPF molecule includes a 5'-end and a 3'-end, as well as a sequence in between that is complementary to all or a part of the target nucleic acid molecule. The 5'-end of a nucleic acid sequence is where the 5' position of the terminal residue is not bound by a nucleotide. The 3'-end of a nucleic acid molecule is the end that does not have a nucleotide bound to it 3' of the terminal residue. This permits specific binding or hybridization between the NPPF and the target nucleic acid molecule. For example, the region of the NPPF that is complementary to a region of the target nucleic acid molecule binds to or hybridizes to that region of the target nucleic acid molecule with high specificity. The NPPF molecule further includes one or more flanking sequences, which are at the 5'-end and/or 3'-end of the NPPF. Thus, the one or more flanking sequences are located 5', 3', or both, to the sequence complementary to the target nucleic acid molecule. Each flanking sequence includes several contiguous nucleotides, generating a sequence that is not found in a nucleic acid molecule otherwise present in the sample (such as a sequence of at least 12 contiguous nucleotides). If the NPPF includes a flanking sequence at both the 5'-end and 3'-end, in some examples the sequence of each NPPF is different and not complementary to each other. In one example, the NPPF (for example in one or both flanking sequences and/or the sequence of the region complementary to all or a portion of the target nucleic acid molecule) includes at least one dUTP, such as at least two, at least three, at least four, or at least five dUTPs (such as 1, 2, 3, 4, 5, 6, 7, 8, 9, or 10 dUTPs). In one example, all of the "Ts" in an NPPF are replaced by "U". The presence of such bases allows the single stranded NPPF to be degraded or destroyed with uracil DNA deglycosylase (UDG) in later step (e.g., after denaturation of the NPPF from the ligated target, but before sequencing, for example before or during amplification of a ligated target). In one example, the NPPF (for example in the sequence of the region complementary to all or a portion of the target nucleic acid molecule, or in the sequence of the flanking region) includes at least one nucleotide mismatch, for example, the nucleotide is not complementary to the target nucleic acid molecule. For example, as shown in FIG. 10, SEQ ID NO: 1 contains a "G" at positon 12 instead of an "A", SEQ ID NO: 8 contains a "G" at positon 15 instead of an "A", and SEQ ID NO: 17 contains a "T" at positon 13 instead of an "C". In some examples, the mismatch is not present in the flanking sequences. In some examples, the mismatch is not present within two bases of the flanking sequences (that is, not within two bases of the 5'-end or the 3'-end of the region complementary to all or a portion of the target nucleic acid molecule of the NPPF. In some examples, the mismatched nucleotide is not present at the junction between a flanking sequence a the region of the NPPF that is complementary to a region of the target nucleic acid molecule, for example is 10, 11, 12, 13, 14, or 15 nucleotides from such a junction. In some examples, the presence of the mismatch allows one to distinguish NPPF from the target nucleic acid molecule.

The flanking sequence(s) are complementary to complementary flanking sequences (CFS). The CFSs provide a universal hybridization/amplification sequence, which is complementary to at least a portion of an amplification primer. In some examples, the CFSs can include (or permit addition of) an experimental tag, sequencing adaptor, or combinations thereof. In some examples, at least one flanking sequence includes at least one dUTP. In some examples, the NPPF includes two flanking sequences, each having at least one dUTP. In some examples, the NPPF includes two flanking sequences, but only one has at least one dUTP. In some examples, the NPPF includes a single flanking sequence having at least one dUTP. In some examples, the location of the dUTP is close to the sequence complementary to a region of the target nucleic acid molecule, such as 1, 2, 3, 4, 5, bases away from (e.g., within 1, 2, 3, 4, 5, bases of) the sequence complementary to a region of the target nucleic acid molecule. In some examples, the location of the dUTP is at least two bases (such at least 3, at least 4, or at least 5 bases) away from the sequence complementary to a region of the target nucleic acid molecule.

The methods further include contacting the sample with at least one nucleic acid molecule having complementarity to the flanking sequence (CFS) under conditions sufficient for the CFS to specifically bind or hybridize to the flanking sequence of the NPPF. For example, if the NPPF has a 5'-flanking sequence, the sample is contacted with a nucleic acid molecule having sequence complementarity to the 5'-flanking sequence (5CFS) and a 5'-end phosphate, under conditions sufficient for the 5'-flanking sequence to specifically bind to the 5CFS. Similarly, if the NPPF has a 3'-flanking sequence, the sample is contacted with a nucleic acid molecule having sequence complementarity to the 3'-flanking sequence (3CFS) under conditions sufficient for the 3'-flanking sequence to specifically bind to the 3CFS. In one example, at least one of the 3CFS and the 5CFS includes a capture moiety that permits capture, separation, retrieval, or isolation of a target sequence. One skilled in the art will appreciate that instead of using a single CFS to protect a flanking sequence, multiple CFSs can be used to protect a flanking sequence (e.g., multiple 5CFSs can be used to protect a 5'-flanking sequence). In some examples, the target nucleic acid molecule is DNA, and the 5CFS and the 3CFS are DNA, or the 5CFS is DNA and the 3CFS is RNA. In some examples, the target nucleic acid molecule is RNA, and the 5CFS is DNA and the 3CFS is RNA or the 5CFS is RNA and the 3CFS is RNA. In some examples, the target nucleic acid molecule is a RNA or DNA, and the 5CFS and/or the 3CFS is an RNA-DNA hybrid oligo, for example wherein the 5' base or bases of the 5CFS and/or the 3' base or bases of the 3CFS are RNA, and the remainder of the 5CFS and 3CFS are DNA. In some examples, one or more CFSs contain modifications to a base, or a modification to the 3' or 5' end of the CFS, such as a phosphothiorate linkage, a nucleotide that will result in a locked nucleic acid (LNA) (e.g., a ribose s modified with an extra bridge connecting the 2' oxygen and 4' carbon), or a chain-terminator (e.g., ddCTP or inverted-T base).

This results in the generation of NPPF molecules that have bound thereto a target nucleic acid molecule (or portion thereof), as well as the CFS(s), thereby generating a double-stranded molecule that includes bases of the NPPF engaged in hybridization to complementary bases on the target and CFS. The CFS(s) hybridizes to and thus protects its corresponding flanking sequence from digestion with the nuclease in subsequent steps. In some examples, each CFS is the exact length of its corresponding flanking sequence. In some examples, the CFS is completely complementary to its corresponding flanking sequence. However, one skilled in the art will appreciate that the 3'-end of a 5CFS that protects a 5'-end flanking sequence or the 5'-end of a 3CFS that protects the 3'-end flanking sequence can have a difference, such as a nucleotide mismatch, a modification discussed above, or combinations thereof, at each of these positions.

After allowing the target nucleic acid molecule and the CFS(s) to bind to the NPPFs, the method further includes contacting the sample with a nuclease specific for single-stranded (ss) nucleic acid molecules or ss regions of a nucleic acid molecule, such as S1 nuclease, under conditions sufficient to remove nucleic acid bases that are not hybridized to complementary bases. Thus for example, NPPFs that have not bound to target nucleic acid molecule or CFSs, as well as unbound single-stranded target nucleic acid molecules, other ss nucleic acid molecules in the sample, and unbound CFSs, are degraded. This generates a digested sample that includes intact NPPFs present as double stranded adducts hybridized to 5CFS, 3CFS, or both, and a portion of the target nucleic acid. In some examples, for example if the NPPF is composed of DNA, the nuclease can include an exonuclease, an endonuclease, or a combination thereof.

Subsequently, the CFS(s) can be ligated to the target nucleic acid, for example the 5'-phosphate of the 5CFS is ligated to the 3'-end of the target nucleic acid molecule, and the 3'-end of the 3CFS is ligated to the 5'-end of the target nucleic acid molecule, thereby generating a ligated target nucleic acid molecule (referred to herein as a ligated target or a cNPPF). In some examples, in addition to ligation, the CFS(s) are exposed to polymerase treatment (e.g., a DNA polymerase), for example to replace nucleotide(s) that may have been removed during the nuclease treatment. The polymerase treatment can be performed at the same time as the ligation, for example in the same reaction vessel. In some examples, the polymerase treatment is performed before the ligation.

The double-stranded NPPF: ligated target nucleic acid molecule is separated into ss nucleic acid molecules (for example by creating an environment that encourages denaturation, such as heating (e.g., about 95° C. in a buffer or about 50° C. in dH$_2$O), increasing the pH of the sample, or treatment with 50% formamide/0.02% TWEEN® detergent), or a combination of such treatments, thereby generating a mixture of ss NPPFs and ss ligated target nucleic acid molecules. In one example, the double-stranded NPPF: ligated target nucleic acid molecule is separated into ss nucleic acid molecules by washing three times for 10 minutes at 50° C. in 0.02% TWEEN® detergent in water. In one example, the double-stranded NPPF: ligated target nucleic acid molecule is separated into ss nucleic acid molecules by washing with 50% formamide/0.02% TWEEN® detergent at room temperature. In some examples, separation of the double-stranded NPPF: ligated target into its corresponding ss nucleic acid molecules includes treatment with a DNase, for example if the target molecule is RNA, the NPPF is DNA, and the 3CFS and 5 CFS are RNA. In such an example, the NPPF can be degraded, cleaved, digested, separated from the ligated RNA target molecule, or combinations thereof, thereby allowing the liberated ss ligated target to be further analyzed (such as amplified, reverse transcribed, sequenced, or combinations thereof). In some examples, separation of the double-stranded NPPF: ligated target into its corresponding ss nucleic acid molecules includes treatment with a RNase, for example if the target molecule is DNA, the NPPF is RNA, and the 3CFS and 5 CFS are DNA. In such an example, the NPPF can be degraded, cleaved, digested, separated from the ligated DNA target molecule, or combinations thereof, thereby allowing the liberated ss ligated target to be further analyzed (such as amplified, sequenced, or combinations thereof). The ss ligated target nucleic acid molecules are optionally retrieved, for example by capturing it, for example by hybridization or use of a capture moiety (e.g., on the 5CFS or 3CFS). In some examples, the mixture of ss NPPFs and ss ligated target nucleic acid molecules are incubated with uracil DNA deglycosylase (UDG) under conditions sufficient for cleaving or destroying the ss NPPFs having at least one dUTP (such as 2, 3, 4, 5, or 6 or more dUTPs).

Figure 2A:
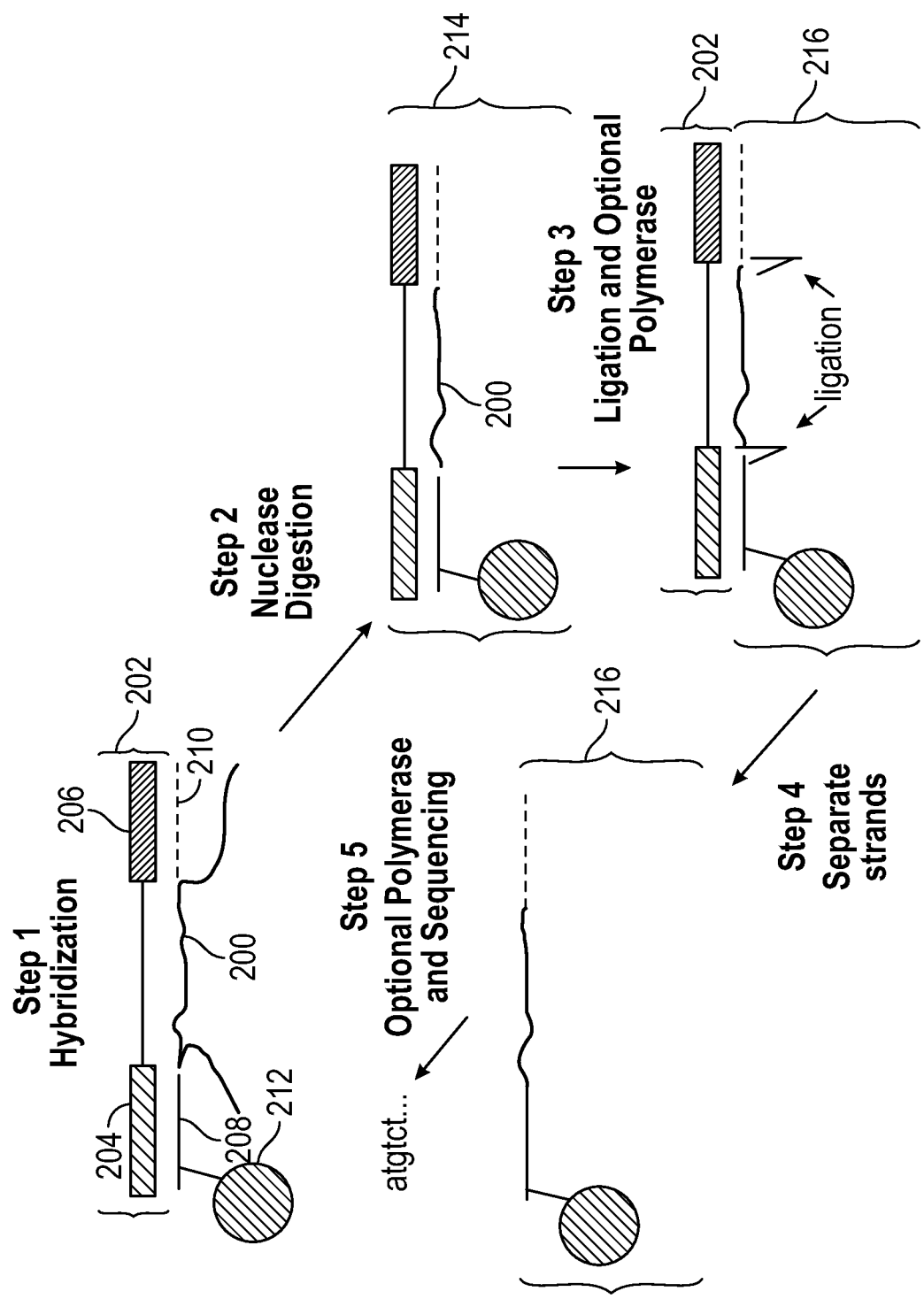
FIG. 2A is a schematic diagram showing an overview of the steps of an illustrative method for direct sequencing of one or more target nucleic acid molecules. (Step 1) A sample (such as cells or FFPE tissue) is contacted with sample disruption buffer (for example to permit lysis of cells and tissues in the sample) and incubated with at least one NPPF 202, and its complementary 5CFS 208 and 3CFS 210 under conditions that allow specific hybridization of the NPPF 202 to the target 200 and to the CFSs 208, 210. (Step 2) Unbound (e.g., single-stranded) nucleic acid is digested with a nuclease specific for ss nucleic acid molecules (such as S1 nuclease). (Step 3) The double stranded NPPF/target duplex 214 is optionally captured or otherwise removed from the nuclease reaction mixture (for example by a capture method that uses capture moiety 212). However, as shown in FIGS. 2B-2D, capture of nucleic acid molecules that include the target can be achieved at earlier steps. The CFSs 208, 210, are ligated to the target 200, for example by addition of ligase, thereby generating a ligated target 216. Optionally, the ligation reaction may include a polymerase (such as a DNA polymerase) to perform a fill-in reaction to replace any nucleotides removed by the nuclease; the polymerase and ligase may be added simultaneously or stepwise. (Step 4) The NPPF/ligated target duplex 214 is separated into ss NPPF 202 and ss ligated target 216. In some examples, to separate the NPPF/ligated target duplex 214 the NPPF of the duplex is treated with a nuclease, for example with a DNase. (Step 5) The ligated target 216 is optionally amplified and polymerized (FIG. 5), for example by using PCR or RT-PCR with appropriate primers, and then sequenced.
Figure 2B:
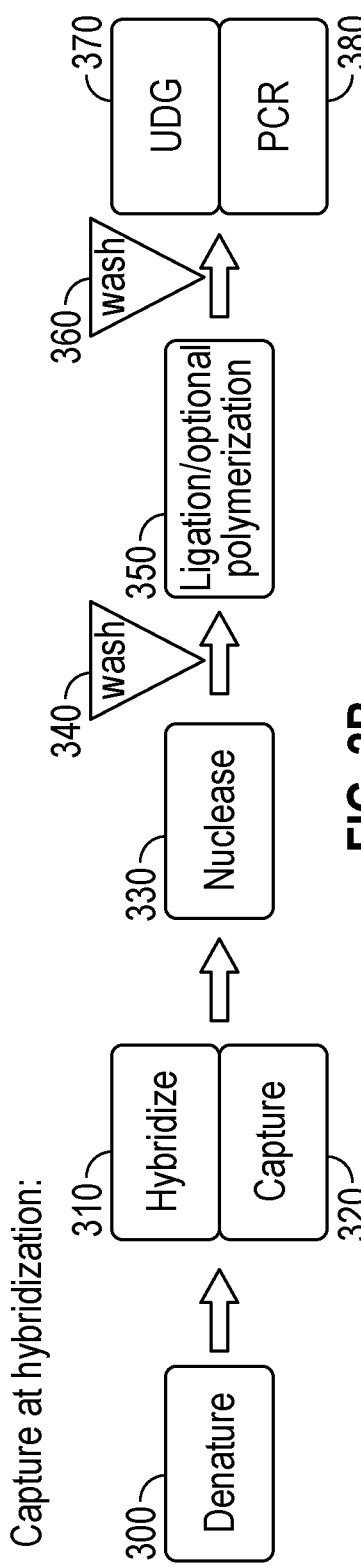
FIGS. 2B-2D are schematic diagrams showing an overview of the steps of an illustrative method for direct sequencing of one or more target nucleic acid molecules, with specific notations as to where capture or retrieval of the target can occur prior to ligation.
Figure 2C:
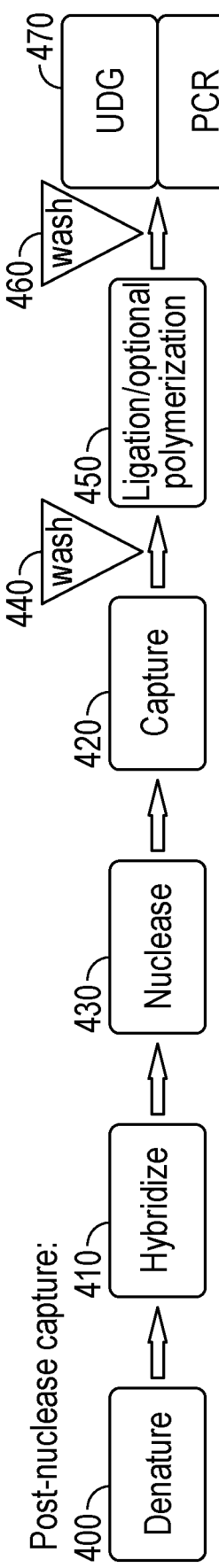
Figure 2D:
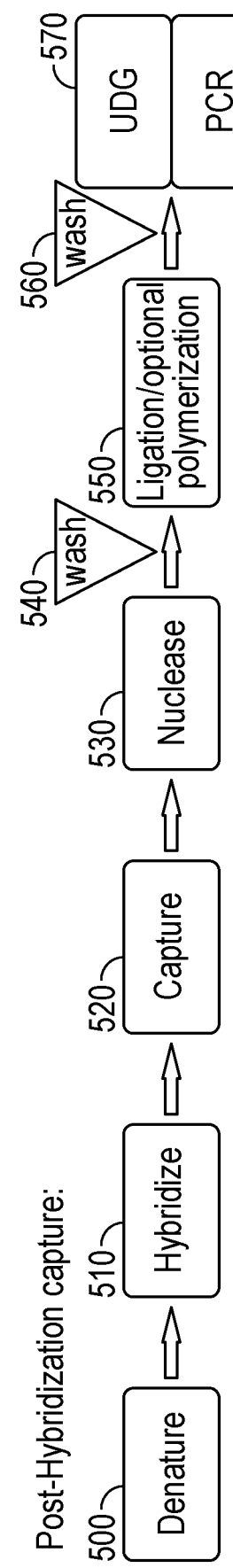

The methods can include one or more steps that allow for capture or retrieval of the target to be sequenced, for example by use of the NPPF, 5CFS or 3CFS. For example, as shown in FIGS. 2B-2D, such capture can occur during hybridization, following nuclease digestion, or following hybridization, but prior to ligation. FIGS. 2A and 2C show an example in which the capture is done after nuclease digestion. Furthermore, additional capture steps can be included, for example following ligation. In one example, the NPPF, 5CFS or 3CFS is attached to a solid substrate (such as a multi-well plate), allowing for molecules to be captured when they hybridize to the anchored NPPF, 5CFS or 3CFS. In another example, a capture moiety (such as a particle or label attached to the target, NPPF, 5CFS or 3CFS) can be used to allow for physical separation of molecules attached or hybridized to the molecule containing the capture moiety from the other components of the sample. Depending on the method of capture, such methods can include centrifugation to collect solid capture moieties, magnetic bead capture, binding or hybridization to a solid support, filtration, etc. In addition, such capture steps can include washing the captured nucleic acid molecules (thereby allowing uncaptured molecules, such as non-hybridized NPPFs and non-hybridized CFS, to be separated or removed). Such methods can include releasing the captured nucleic acid molecules from a solid support, such as a well of a multiwell plate or a single-reaction tube or vessel, or the captured nucleic acid molecules can remain affixed to or within the solid support. In some examples, this step includes centrifugation, for example to capture the target nucleic acid molecule to the bottom of a vessel or tube, and washing to allow removal of undesired or unneeded agents. In some examples, this step includes magnetic bead capture of the target nucleic acid molecule, and washing to allow removal of undesired or unneeded agents. In some examples, this step includes filtration to capture the target nucleic acid molecule, and washing to allow removal of undesired or unneeded agents. This step can include washing the target nucleic acid molecule, which in some examples removes agents no longer needed (e.g., the nuclease) and/or permits the target nucleic acid molecule to be suspended in another solution, which may facilitate one or more next steps in a particular method embodiment.

In some examples, multiple steps of the method (such as two, three, or four of the steps shown in FIG. 2A) are performed in the same vessel or container. For example, the disclosed methods allow the desired component(s) to remain in the same vessel for multiple steps, while undesired or unneeded components are removed (e.g., using repeated capture and washing steps). For example, the sample to be analyzed can be lysed in a vessel. Appropriate NPPFs and CFSs are added to that vessel, the nuclease added to that vessel, and the ds nucleic acid molecule captured in the vessel (e.g., with magnetic beads drawn to the bottom of the vessel). The captured ds nucleic acid molecule is washed to remove undesired agents, and desired buffers or reagents added to the vessel (e.g., a ligase buffer). The ss ligated target nucleic acid molecules can then be captured in the vessel, and washed.

The ligated target nucleic acid molecules are optionally amplified, for example using PCR amplification. Such methods can be used to add an experiment tag and/or sequence adaptor to the ligated target, and/or to increase the number of copies of the ligated target. At least a portion of the ss ligated target nucleic acid molecule (or amplicon thereof) is sequenced, thereby determining the sequence of the at least one target nucleic acid molecule in the sample. In some examples, the target nucleic acid molecules are RNA, and the method includes reverse transcribing them into DNA prior to sequencing.

Ligated targets can be amplified using one or more amplification primers, thereby generating ligated target amplicons. At least one amplification primer includes a region that is complementary to a CFS ligated to the target. In some examples, the target is ligated to a 5CFS at its 5'-end and to a 3CFS at its 3'-end, and two amplification primers are used, wherein one amplification primer has a region that is identical to a region of the 5CFS and the other amplification primer has a region that is complementary to a region of the 3CFS. In some examples, the target is ligated to either a 5CFS or a 3CFS at its 5'-end and 3'-end, respectively, and one amplification primer is used (for example using rapid amplification or cDNA ends), wherein the amplification primer has a region that is complementary to a region of the 5CFS or 3CFS. One or both of the amplification primers can include a sequence that permits attachment of an experiment tag and/or sequencing adaptor to the ligated target amplicon during the amplification, and one or both primers can be labeled to permit labeling of the NPPF amplicon. In some examples, both an experiment tag and a sequencing adaptor are added, for example at opposite ends of the ligated target amplicon. For example, the use of such primers can generate an experiment tag and/or sequence adaptor extending from the 5'-end or 3'-end of the ligated target amplicon, or from both the 3'-end and 5'-end to increase the degree of multiplexing possible. The experiment tag can include a unique nucleic acid sequence that permits identification of a sample, subject, or target nucleic acid sequence. The sequencing adaptor can include a nucleic acid sequence that permits capture of the resulting ligated target amplicon onto a sequencing platform. In some examples, primers are removed from the mixture prior to sequencing.

The ligated target or ligated target amplicons (or portion thereof) is sequenced. Any method can be used to sequence the ligated target or ligated target amplicons, and the disclosure is not limited to particular sequencing methods. In some examples, the sequencing method used is chain termination sequencing, dye termination sequencing, pyrosequencing, nanopore sequencing, or massively parallel sequencing (also called, next-generation sequencing (or NGS)), which is exemplified by ThermoFisher ION TORRENT™ Personal Genome Machine (PGM™) NGS sequencers, and ILLUMINA® NGS sequencers (e.g., MiSeq™, HiSeq™) (or as otherwise derived from Solexa™ sequencing), and 454 sequencing available from Roche Life Sciences. In some examples, single molecule sequencing is used. In some examples, the method also includes comparing the obtained target sequence to a sequence database, for example to determine if a target mutation is present or absent. In some examples, the method includes determining the number of (e.g., counting) each target sequence obtained (e.g., wild type, SNPs, newly identified variant, etc.), for example using bowtie, bowtie2, or TMAP sequence aligners. In some examples, the method includes aligning the sequencing results to an appropriate genome (e.g., if the target nucleic acid molecule is a human gene, then the appropriate genome is the human genome) or portions thereof. In one example, the method includes aligning to only the expected target sequences but enumerating both matches to the expected sequence and any changes within the expected sequence.

II. Methods of Direct Sequencing of Target Nucleic Acid Molecules

Disclosed herein are methods of direct sequencing of one or more target nucleic acid molecules present in a sample. In some examples, at least two different target nucleic acid molecules are detected in the same sample or same assay. In some examples, the same target nucleic acid molecule(s) is detected in at least two different samples or assays (for example, in samples from different patients). Thus, the disclosed methods can be multiplexed (e.g., detecting a plurality of targets in a single sample), high-throughput (e.g., detecting a target in a plurality of samples), or multiplexed and high-throughput (e.g., detecting a plurality of targets in a plurality of samples).

In the disclosed methods, following hybridization of NPPFs to their target and corresponding CFSs, nuclease digestion, the CFSs are ligated to the target (and in some examples treated with a polymerase), generating a ligated target. The ds NPPF: ligated target is then separated (e.g., denatured), resulting in ss NPPF and ss ligated target. In some examples, the ss ligated target is retrieved or captured (e.g., isolated from the NPPF), for example by using a capture moiety on the 3CFS or 5CFS. In some examples, the ss ligated target is amplified, for example by using primers having a region that is complementary to the CFS(s) (and can include sequences that allow the incorporation of an experiment tag and/or sequence adaptor to the ligated target). This ss ligated target can then be sequenced directly (or amplicons thereof can be sequenced). In some examples, the disclosed methods provide sequenced nucleic acid molecules that similar relative quantities of the nucleic acid molecules as in the test sample, such as a variation of no more than 20%, no more than 15%, no more than 10%, no more than 9%, no more than 8%, no more than 7%, no more than 6%, no more than 5%, no more than 4%, no more than 3%, no more than 2%, no more than 1%, no more than 0.5%, or no more than 0.1%, such as 0.001%-5%, 0.01%-5%, 0.1%-5%, or 0.1%-1%.

Figure 1B:
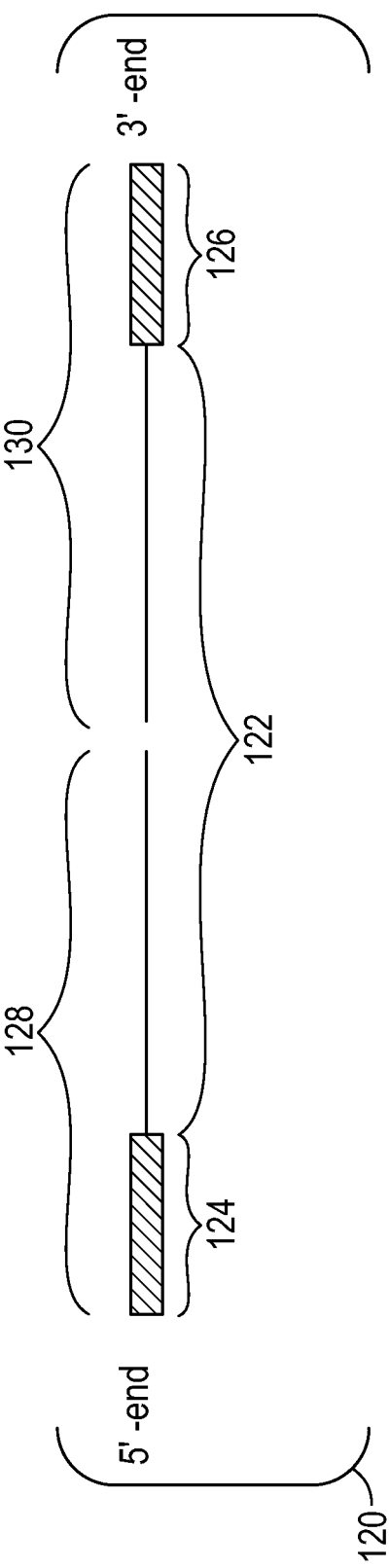
FIG. 1B is a schematic diagram showing an exemplary nuclease protection probe having flanking sequences (NPPF), 120. In this example, the NPPF 120 is composed of two separate nucleic acid molecules 128, 130, instead of a single nucleic acid molecule as shown in FIG. 1A. The NPPF 120 includes a region 122 having a sequence that specifically binds to/hybridizes to a target nucleic acid sequence. The NPPF also includes a 5'-flanking sequence 124, a 3'-flanking sequence 126, or both (the embodiment with both is shown).

FIGS. 1A and 1B are schematic diagrams showing exemplary NPPFs. As shown in FIG. 1A, the nuclease protection probe having at least one flanking sequence (NPPF) 100 includes a region 102 that includes a sequence that specifically binds to (e.g., hybridizes to) the target nucleic acid sequence (e.g., at least a portion of the target nucleic acid sequence). The region 102 that includes a sequence that specifically binds to (e.g., hybridizes to) the target nucleic acid sequence, or a flanking sequence 104, 106, can include a deliberate nucleotide mismatch (that is, the nucleotide is not complementary to the corresponding nucleotide in the target sequence or in the CFS, respectively), for example to allow one to distinguish an NPPF from a target molecule. The target nucleic acid sequence can be DNA (e.g., genomic DNA or cDNA) or RNA (such as mRNA, miRNA, tRNA, siRNA), or both. The NPPF includes one or more flanking sequences 104 and 106. FIG. 1A shows an NPPF 100 with both a 5'-flanking sequence 104 and a 3'-flanking sequence 106. However, NPPFs can in some examples have only one flanking sequence (e.g., only one of 104 or 106). In some examples, NPPF 100 includes at least one dUTP, such as in at least one of the flanking sequences 104, 106, for example to permit degradation of the NPPF 100. FIG. 1A shows an exemplary NPPF 100 that is a single nucleic acid molecule. FIG. 1B shows an exemplary NPPF 120 that is composed of two separate nucleic acid molecules 128, 130 that cannot be ligated together. For example if NPPF 100 is a 100-mer, NPPF 120 could be two 50-mers. Like the NPPF 100 shown in FIG. 1A, the NPPF 120 includes a region 122 that includes a sequence that specifically binds to (e.g., hybridizes to) the target nucleic acid sequence (e.g., at least a portion of the target nucleic acid sequence), and one or more flanking sequences 124 and 126. The use of an NPPF composed of two separate nucleic acid molecules (FIG. 1B) may be used to decrease background signal due to incomplete nuclease digestion.

FIG. 2A is a schematic diagram showing an overview of an embodiment of the disclosed methods for using NPPFs 202 to sequence a nucleic acid molecule. As shown in step 1, a sample (such as one known or suspected of containing a target nucleic acid, 200 that has been treated with a sample disruption buffer (e.g., lysed or otherwise treated to make nucleic acids accessible) is contacted or incubated with a plurality of nuclease protection probes having one or more flanking sequences (NPPFs) 202 (shown here with both a 5'- and a 3'-flanking sequence, 204 and 206, respectively), including at least one NPPF which specifically binds to a first target nucleic acid 200 (such as a target DNA or RNA). In some examples, the at least one NPPF 202 can bind to a plurality of target nucleic acid molecules, such as a wild type and variant sequences of a particular gene (e.g., see FIG. 10). The reaction can also include other NPPFs which specifically bind to a second target nucleic acid (or to a plurality of additional target nucleic acid molecules), and so on.

In one example, the method uses one or more different NPPFs designed to be specific for each unique target nucleic acid molecule. Thus, the measurement of 100 different nucleic acid targets (e.g., genes or gene expression product(s)) can use at least 100 different NPPFs, with at least one NPPF specific per target (such as several different NPPFs/target). In another example, the method uses one or more different NPPFs designed to be specific for a plurality of target nucleic acid molecules, such as a wild type gene and variations thereof. Thus, the measurement of multiple different nucleic acid targets can use a single NPPF. In some examples, combinations of these two types of NPPFs are used in a single reaction. Thus, the method can use at least 2 different NPPFs, at least 3, at least 4, at least 5, at least 10, at least 25, at least 50, at least 75, at least 100, at least 200, at least 500, at least 1000, at least 2000, or at least 2000 different NPPFs (such as 2 to 500, 2 to 100, 5 to 10, 2 to 10, 2 to 20, 100 to 500, 100 to 1000, 500 to 5000 or 1000 to 3000 different NPPFs). In addition, one will appreciate that in some examples, the plurality of NPPFs can include more than one (such as 2, 3, 4, 5, 10, 20, 50 or more) NPPFs specific for a single target nucleic acid molecule (which is referred to as a tiled set of NPPFs). The reaction also includes nucleic acid molecules that are complementary to the flanking sequences (CFS) 208, 210. Thus, if the NPPF has a 5'-flanking sequence 204, the reaction will include a sequence complementary to the 5'-flanking sequence (5CFS) 208 and if the NPPF has a 3'-flanking sequence 206, the reaction will include a sequence complementary to the 3'-flanking sequence (3CFS) 210. In some examples, the 5CFS 208 has a 5'-end phosphate (e.g., see FIG. 3), which allows for ligation to the target 200 at a later step. In some examples, at least one of the CFSs includes a capture moiety 212, which permits retrieval of the target at the desired time. Although the capture moiety 212 is shown in the 5CFS 208, it will be appreciated that in embodiments where it is present, it can alternatively be on the 3CFS 210, the NPPF 202 or the target 200. One skilled in the art will appreciate that the sequence of the CFSs will vary depending on the flanking sequence present. In addition, more than one CFS can be used to ensure a flanking region is protected (e.g., at least two CFSs can use that bind to different regions of a single flanking sequence). The CFS can include natural or unnatural bases.

Figure 3:
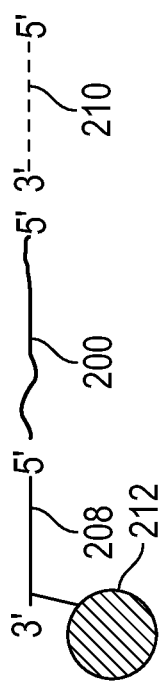
FIG. 3 is a schematic diagram showing details of the arrangement of illustrative 5CFS 208, target 200, and 3CFS 210 prior to ligation. Although the capture moiety 212 is shown on 5CFS 208, it can alternatively be on the 3CFS 210 or the NPPF 202. Other embodiments (not shown) involve 5CFS 208 and target 200, or target 200 and 3CFS 210.

FIG. 3 shows further details on the orientation of the 5CFS 208, target 200, and 3CFS 208 (e.g., with respect to the 5'- and 3'-end of each molecule). As discussed above for FIG. 2, the capture moiety 212 in FIG. 3 is optional, or can be on the 3CFS 210 or target 200. The sample, NPPFs and CFSs are incubated under conditions sufficient for NPPFs to specifically bind to (e.g., hybridize to) their respective target nucleic acid molecule, and for CFSs to bind to (e.g., hybridize to) their complementary sequence on the NPPF flanking sequence. In some examples, the CFSs 208, 210 are added in excess of the NPPFs 202, for example at least 2-fold more CFSs than NPPFs (molar excess), such as at least 3-fold, at least 4-fold, at least 5-fold, at least 6-fold, at least 7-fold, at least 8-fold, at least 9-fold, at least 10-fold, at least 20-fold, at least 40-fold, at least 50-fold, or at least 100-fold more CFSs than the NPPFs. In some examples, the NPPFs 202 are added in excess of the total nucleic acid molecules in the sample, for example at least 50-fold more NPPF than total nucleic acid molecules in the sample (molar excess), such as at least 75-fold, at least 100-fold, at least 200-fold, at least 500-fold, or at least 1000-fold more NPPF than the total nucleic acid molecules in the sample. For experimental convenience a similar concentration of each NPPF can be included to make a cocktail, such that for the most abundant nucleic acid target measured there will be at least 50-fold more NPPF for that nucleic acid target, such as an at least 100-fold excess. The actual excess and total amount of all NPPFs used is limited only by the capacity of the nuclease (e.g., S1 nuclease) to destroy all NPPF's that are not hybridized to target nucleic acid targets. In some examples the reaction is heated, for example incubated for overnight (such as for 16 hours) at 50° C.

As shown in step 2 in FIG. 2A, after allowing the binding/hybridization reactions to occur, the sample is contacted with a reagent (such as, a nuclease) specific for single-stranded (ss) nucleic acid molecules under conditions sufficient to remove (or digest) ss nucleic acid molecules, such as unbound nucleic acid molecules (such as unbound NPPFs, unbound CFSs, and unbound target nucleic acid molecules, or portions of such molecules that remain single stranded, such as portions of a target nucleic acid molecule not bound to the NPPF). This results in the generation of a ds NPPF/target hybridized complex (or duplex) 214. As shown in FIG. 2A, incubation of the sample with a nuclease specific for ss nucleic acid molecules results in degradation of any ss nucleic acid molecules present, leaving intact double-stranded nucleic acid molecules, including NPPFs that have bound thereto and CFSs and target nucleic acid molecule. For example, the reaction can be incubated at 50° C. for 1.5 hours with S1 nuclease (though hydrolysis can occur at other temperatures and be carried out for other periods of time, and in part that the time and temperature required will be a function of the amount of nuclease, and on the amount of nucleic acid required to be hydrolyzed, as well as the Tm of the double-stranded region being protected).

Figure 4:
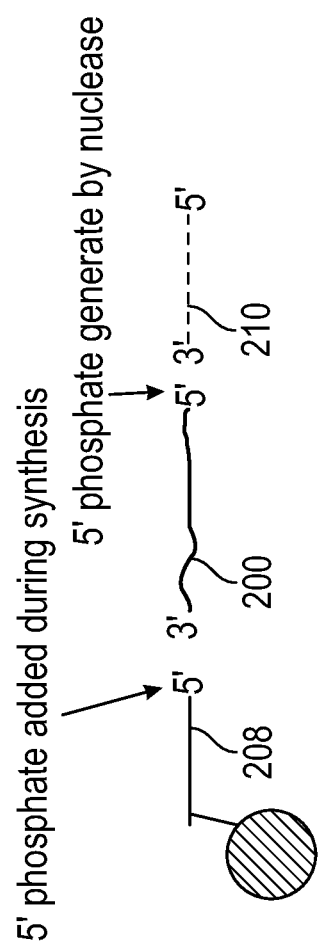
FIG. 4 is a schematic diagram showing that how the 5CFS 208 and 3CFS 210 can ligate to the target 200, by appropriate 5' phosphate groups.

As shown in step 3 of FIG. 2A, the NPPF/target complex 214 (which is captured or retrieved at some time prior to the ligation, see FIGS. 2B-2D, and non-hybridized material removed), is exposed to ligation conditions, that allow the target sequence 200 (which can be DNA or RNA) to be ligated to the CFSs (e.g., to the 5CFS 208, 3CFS 210, or both), thereby generating a ligated target 216. Any ligase capable of covalently joining the target sequence and CFS(s) can be used, such as a T4 DNA ligase, T4 RNA ligase, or Taq ligase. The ligase used may depend on the nucleotide (ribonucleotide or deoxyribonucleotide) present on the CFS that is closest to the target sequence. FIG. 4 shows a larger detail view of the elements that are ligated. The 5CFS 208 can include a 5'-end phosphate, which can be ligated to the 3'-end of the target 200. The 3CFS 210 can include a 3'-end (such as a 3'-terminal nucleotide), which can be ligated to the 5'-end phosphate of the target. The 3CFS 210 can include an internal biotinylated T near the 5'-end (but not at the 5'-end) of the oligonucleotide, which allows for binding to streptavidin beads or other solid support. Alternatively, the 5CFS 208 can include an internal biotinylated T near the 3' end (but not at the 3' end) of the oligonucleotide, allowing binding to streptavidin beads or other solid support. Although two CFSs are shown, single CFS embodiments are also contemplated by this disclosure. If only one flanking sequence is present on the NPPF, only one CFS will have been bound in the NPPF/target complex, and the target will be ligated to only one CFS. The CFSs can be DNA or RNA (or a mixture of both nucleotide types). If the CFS or target is DNA, the 5'-end phosphate donor for ligation to DNA cannot be a ribonucleotide. In one example if the target is RNA, the 5CFS 208 is DNA or RNA and the 3CFS 210 is RNA. In one example if the target is DNA, the 5CFS 208 is DNA (or at least the 5'-end nucleotide of the 5CFS 208 is a dNTP that will ligate to the 3'-end of the target) or RNA and the 3CFS 210 is RNA.

In some examples, step 3 of FIG. 2A also includes a polymerization step, in addition to the ligation. For example, the polymerization can be performed at the same time as the ligation (e.g., in the same reaction), or prior to ligation. This can allow nucleotides that were inadvertently removed from the CFS or the target during the nuclease step to be restored. In some examples, the polymerase used does not have significant strand-displacement activity or 5'-3' exonuclease capability (which may remove and replace the target hybridized to the probe, rather than simply replacing missing bases). In one example, a DNA polymerase is used, such as T4 or T7 DNA polymerase or an exonuclease-free thermostable polymerase, in the presence of dNTPs. In one example, the polymerase is not Taq polymerase (unless it lacks exonuclease activity). In one example, an RNA polymerase is used, such as *E. coli* RNA polymerase, with rNTPs added. If an RNA polymerase is used, the method can further include a reverse transcription step (e.g., at the time of PCR amplification of ligated target 216 discussed below). In some examples, for example if the targets include DNA and RNA, both a DNA polymerase and an RNA polymerase are used.

As shown in step 4 of FIG. 2A, after ligating the CFS(s) to the target, the NPPF 202 is separated from the ligated target 216. That is, the NPPF/target complex 214 (e.g., double stranded nucleic acid molecule) is separated into two single stranded nucleic acid molecules, the NPPF 202 and the ligated target 216. In some examples, the NPPF 202 is treated with a DNase, thereby allowing for its separation from the ligated target 216. In such an example, the NPPF 202 can be DNA, the target 200 RNA, the 5CFS 208 RNA, and 3CFS 210 RNA. In some examples, the NPPF 202 is treated with a RNase, thereby allowing for its separation from the ligated target 216. In such an example, the NPPF 202 can be RNA, the target 200 DNA, the 5CFS 208 DNA, and 3CFS 210 DNA. This step can also remove unligated nucleic acid molecules (e.g., unligated CFS). For example, the reaction can be heated or the pH altered (e.g., to result in the reaction having a basic pH) under conditions that allow the NPPF 202 to dissociate from the ligated target 216, resulting in a mixed population of single stranded NPPFs 202 and single stranded ligated targets 216. In some examples, DNase is added to the reaction to allow the NPPF 202 composed of DNA to be degraded, digested, cleaved, separated, or any combination thereof, which permits the ligated target 216 (which can be RNA in this example) to be liberated or separated from the NPPF 202. In some examples, RNase is added to the reaction to allow the NPPF 202 composed of RNA to be degraded, digested, cleaved, separated, or any combination thereof, which permits the ligated target 216 (which can be DNA in this example) to be liberated or separated from the NPPF 202. In some examples, the ligated target 216 is separated from this mixture by using the capture moiety 212 on the CFS. Capture methods described herein can be used to capture the ligated target 216. For example if the capture moiety 212 is a bead, the ligated target 216 can be retrieved using centrifugation. If the capture moiety 212 is a metal bead, the ligated target 216 can be retrieved using a magnet. If the capture moiety 212 includes a carboxyl group, the ligated target 216 can be captured using an appropriately amine-labeled solid substrate. Following capture of the ligated target 216, the remainder of the reaction (e.g., the NPPF 202) can be removed (e.g., by washing). In some examples, the ligated target 216 is captured using filtration.

As shown in step 5 of FIG. 2A, the isolated ligated target 216 (or amplicons thereof) is then sequenced. In some examples, a plurality of ligated targets are sequenced in parallel, for example simultaneously or contemporaneously. This method can thus be used to sequence a plurality of ligated target sequences.

Figure 5:
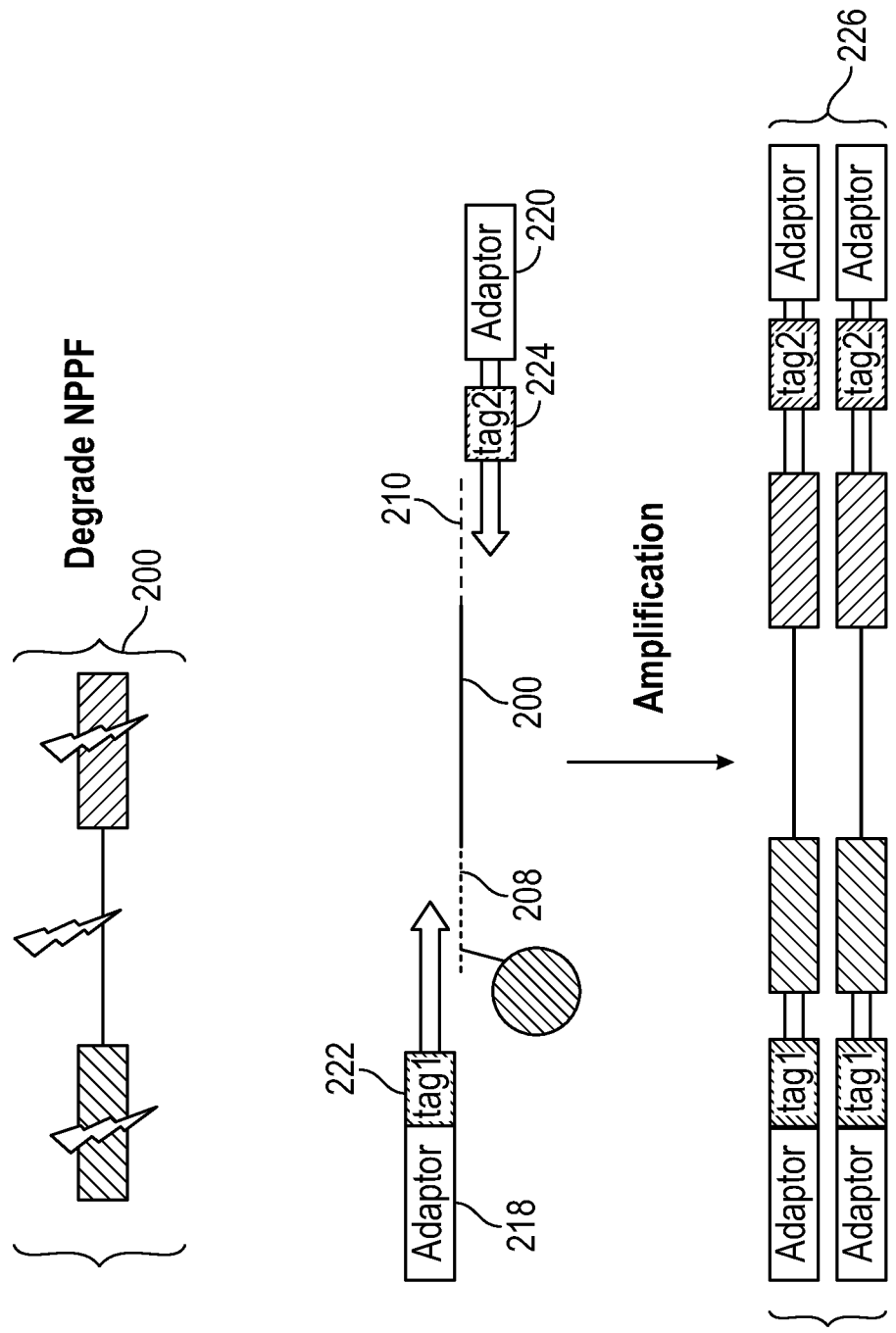
FIG. 5 is a schematic diagram showing that, in some embodiments, ligated target can be amplified using primers (arrows) and the NPPFs 200 degraded, resulting in ligated target amplicons 226. The primers can include sequences that allow sequencing adaptors 218, 220 and/or experiment tags 222, 224, to be added to the ligated target amplicons 226.

Optionally, the ligated targets 216 are amplified (e.g., using PCR), washed, or both, prior to the sequencing. In some examples, the NPPFs 202 are degraded with uracil DNA deglycosylase (UDG), for example if at least one flanking sequence (e.g., 104, 106 of FIG. 1A), or the capture sequence (e.g., 102 of FIG. 1A), includes dUTP (see FIG. 5). Such degradation can occur before or during the amplification. In some examples, such as if the target is RNA, a reverse transcription step can be included as part of the amplification. Thus, the resulting ligated target amplicons 226 can then be sequenced. FIG. 5 shows the PCR primers or probes as arrows. The PCR primers or probes can include one or more experiment tags 222, 224 and/or sequencing adaptors 218, 220 (e.g., that allow the ligated targets to be sequenced by a particular sequencing platform, and thus such adaptors are complementary to capture sequences on a sequencing chip). At least a portion of the PCR primers/probes are specific for the 5CFS 208 and/or 3CFS 210. In some examples, the concentration of the primers are in excess of the ligated target 216, for example in excess by at least 10,000-fold, at least 50,000-fold, at least 100,000-fold, at least 150,000-fold, at least 200,000-fold, at least 400,000-fold, at least 500,000-fold, at least 600,000-fold, at least 800,000-fold, or at least 1,000,000-fold. In some examples, the concentration of primers 208 in the reaction is at least 200 nM (such as at least 400 nM, at least 500 nM, at least 600 nM, at least 750 nM, or at least 1000 nM).

As shown in FIGS. 2B-2D, at a point(s) prior to ligation (e.g., step 3 of FIG. 2A), the target (200 of FIG. 2A) and other molecules attached/hybridized thereto, is retrieved or captured (step 320), thus allowing for removal of the remaining agents in the sample (e.g., non-hybridized material), and addition of new reagents. In addition, capture of the target allows for subsequent washing of nucleic acid molecules hybridized or otherwise attached to the target (e.g. to inactivate or remove residual enzymes).

In one example, the target is retrieved or captured at hybridization (FIG. 2B). As shown in FIG. 2B, following optional denaturation 300, the sample containing the target is incubated with the NPPF and CFS(s) under conditions that permit hybridization 310, thereby producing a hybridized complex. In such an example, the target, along with the NPPF to which it will hybridize, and the CFS(s) that can hybridize to the NPPF, are incubated in the presence of a solid support containing a material that allows capture of the resulting hybridized complex 320. For example, the capture moiety (e.g., 212 in FIG. 2A) present on the 3CSF, 5CSF, and/or NPPF can be utilized as the solid support. For example if the capture moiety is a bead or plate (e.g., attached to a CFS using a carboxy-amine linkage, such as an amino group on the CFS and a carboxy on the bead), the solid support is the bead or plate. In this case, the capture moiety/solid support allows the hybridized complex to bind to the solid support (e.g., because the NPPF will hybridize to the CFS attached to the solid support, and the target and other CFS will hybridize to the NPPF). The method can include wash steps following the hybridization. One or more of the subsequent steps, such as the nuclease digestion 330, washes 340, ligation 350, UDG digestion 370 (optional, only if the NPPF includes dUTP), and/or the PCR amplification 380 can take place in the presence of the solid support, which allows reagents to be removed and added to the captured target.

In one example, the target is retrieved or captured following nuclease treatment (e.g., after step 2 in FIG. 2A), but before ligation (e.g., before step 3 in FIG. 2A) (FIG. 2C). As shown in FIG. 2C, following optional denaturation 400, hybridization 410, and nuclease digestion 430, which produces a NPPF/target complex (214 in FIG. 2A), the NPPF/target complex is retrieved from the sample mixture at step 420. In some examples, the NPPF/target complex is retrieved by using a capture moiety on the CFS, without separating the NPPF/target duplex into ss nucleic acid molecules. For example, the capture moiety (e.g., 212 in FIG. 2A) present on the 3CSF, 5CSF, and/or NPPF can be utilized as the solid support. For example if the capture moiety is a bead or plate (e.g., attached to a CFS using a carboxy-amine linkage, such as an amino group on the CFS and a carboxy on the bead), the solid support is the bead or plate. In this case, the capture moiety/solid support is part of the NPPF/target complex, which allows for its capture or retrieval. The method can include wash steps 440 following the retrieval. One or more of the subsequent steps, such as the ligation 450, washing 460, UDG digestion 470 (optional, only if the NPPF includes dUTP), and/or the PCR amplification 480 can take place in the presence of the solid support, which allows reagents to be removed and added to the captured target.

In one example, the target is retrieved or captured following hybridization (e.g., after step 1 in FIG. 2A), but before nuclease digestion (e.g., before step 2 in FIG. 2A) (FIG. 2D). As shown in FIG. 2D, following optional denaturation 500 and hybridization 510, which produces a hybridized complex, the resulting hybridized complex is retrieved from the sample mixture at step 520. In some examples, the hybridized complex is retrieved by using a capture moiety on the CFS. For example, the capture moiety (e.g., 212 in FIG. 2A) present on the 3CSF, 5CSF, and/or NPPF can be utilized as the solid support. For example if the capture moiety is a bead or plate (e.g., attached to a CFS using a carboxy-amine linkage, such as an amino group on the CFS and a carboxy on the bead), the solid support is the bead or plate. In this case, the capture moiety/solid support is part of the hybridized complex, which allows for its capture or retrieval. The method can include wash steps following the retrieval. One or more of the subsequent steps, such as the nuclease digestion 530, ligation 550, washing 540, 560, UDG digestion 570 (optional, only if the NPPF includes dUTP), and/or the PCR amplification 580 can take place in the presence of the solid support, which allows reagents to be removed and added to the captured target.

A. Exemplary Hybridization Conditions

Disclosed herein are conditions sufficient for a NPPF or a plurality of NPPFs to specifically hybridize to target nucleic acid molecule(s), such as DNAs and RNAs present in a sample from a subject, as well as specifically hybridize to CFS complementary to the flanking sequence(s). In some examples, a plurality of NPPFs include at least 2, at least 5, at least 10, at least 20, at least 100, at least 500, at least 1000, or at least 3000 (such as 2 to 5000, 2 to 3000, 10 to 1000, 50 to 500, 25 to 300, 50 to 300, 10 to 100, 50 to 100, 500 to 1000, or 1000 to 5000) unique NPPF sequences.

Hybridization is the ability of complementary single-stranded DNA, RNA, or DNA/RNA hybrids, to form a duplex molecule (also referred to as a hybridization complex). For example, the features (such as length, base composition, and degree of complementarity) that will enable a nucleic acid (e.g., an NPPF) to hybridize to another nucleic acid (e.g., a target DNA or target RNA or CFS) under conditions of selected stringency, while minimizing non-specific hybridization to other substances or molecules can be determined based on the present disclosure. "Specifically hybridize" and "specifically complementary" are terms that indicate a sufficient degree of complementarity such that stable and specific binding occurs between a first nucleic acid molecule (e.g., an NPPF) and a second nucleic acid molecule (such as a nucleic acid target, for example, a DNA or RNA target, or a CFS). The first and second nucleic acid molecules need not be 100% complementary to be specifically hybridizable. Specific hybridization is also referred to herein as "specific binding." Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, NY (chapters 9 and 11).

Characteristics of the NPPFs are discussed in more detail in Section III, below. Typically, a region of an NPPF will have a nucleic acid sequence (e.g., FIG. 1A, 102) that is of sufficient complementarity to its corresponding target nucleic acid molecule(s) to enable it to hybridize under selected stringent hybridization conditions, as well as a region (e.g., FIG. 1A, 104, 106) that is of sufficient complementarity to its corresponding CFS to enable it to hybridize under selected stringent hybridization conditions. In some examples, an NPPF shares at least 90%, at least 92%, at least 95%, at least 98%, at least 99% or 100% complementarity to its target sequence(s). Exemplary hybridization conditions include hybridization at about 37° C. or higher (such as about 37° C., 42° C., 50° C., 55° C., 60° C., 65° C., 70° C., 75° C., or higher, such as 45-55° C. or 48-52° C.). Among the hybridization reaction parameters which can be varied are salt concentration, buffer, pH, temperature, time of incubation, amount and type of denaturant such as formamide. For example, nucleic acid (e.g., a plurality of NPPFs) can be added to a sample at a concentration ranging from about 10 pM to about 10 nM (such as about 30 PM to 5 nM, about 100 pM to about 1 nM, such as 1 nM NPPFs), in a buffer (such as one containing NaCl, KCl, H$_2$PO$_4$, EDTA, 0.05% Triton X-100, or combinations thereof) such as a lysis buffer.

In some examples, the NPPFs are added in excess of the corresponding target nucleic acid molecules in the sample, such as an at least 10-fold, at least 50-fold, at least 75-fold, at least 100-fold, at least 250-fold, at least 1,000 fold, at least 10,000 fold, at least 100,000 fold, at least 1,000,000 fold, or at least 10,000,000 fold molar excess or more of NPPF to corresponding target nucleic acid molecules in the sample. In one example, each NPPF is added to the sample at a final concentration of at least 10 pM, such as at least 20 pM, at least 30 pM, at least 50 pM, at least 100 pM, at least 150 pM, at least 200 pM, at least 500 pM, at least 1 nM, or at least 10 nM. In one example, each NPPF is added to the sample at a final concentration of about 30 pM. In another example, each NPPF is added to the sample at a final concentration of about 167 pM. In a further example, each NPPF is added to the sample at a final concentration of about 1 nM. In a further example, each NPPF is added to the sample at least about 100,000,000, at least 300,000,000, or at least about 3,000,000,000 copies per µl. In some examples, the CFSs are added in excess of the NPPFs, such as an at least 2-fold, at least 3-fold, at least 4-fold, at least 5-fold or at least 10-fold molar excess of CFS to NPPF. In one example, each CFS is added to the sample at a final concentration of about at least 6-times the amount of probe, such as at least 10-times or at least 20-times the amount of probe (such as 6 to 20 times the amount of probe). In one example, each CFS (e.g., 5CFS and 3CFS) is added at least 1 nM, at least 5 nM, at least 10 nM, at least 50 nM, at least 100 nM, or at least 200 nm, such as 1 to 100, 5 to 100 or 5 to 50 nM. For example if there are six probes, each at 166 pM, each CFSs can be added at 5 to 50 nM.

Prior to hybridization, the nucleic acids in the sample are denatured, rendering them single stranded and available for hybridization (for example at about 95° C. to about 105° C. for about 5-15 minutes, such as 95° C. for 10 minutes). By using different denaturation solutions, this denaturation temperature can be modified, so long as the combination of temperature and buffer composition leads to formation of single stranded target DNA or RNA or both. The nucleic acids in the sample and the 5CFS, 3CFS, or both, are then hybridized to the plurality of NPPFs for between about 10 minutes and about 72 hours (for example, at least about 1 hour to 48 hours, about 2 to 16 hours, about 6 hours to 24 hours, about 12 hours to 18 hours, about 16 hours, or overnight, such as 2 to 20 hours) at a temperature ranging from about 4° C. to about 70° C. (for example, about 37° C. to about 65° C., about 42° C. to about 60° C., or about 50° C. to about 60° C., such as 50° C.). In one example, hybridization is performed at 50° C. for 2 to 20 hours. Hybridization conditions will vary depending on the particular NPPFs and CFSs used, but are set to ensure hybridization of NPPFs to the target molecules and the CFSs. In some examples, the plurality of NPPFs and CFSs are incubated with the sample at a temperature of at least about 37° C., at least about 40° C., at least about 45° C., at least about 50° C., at least about 55° C., at least about 60° C., at least about 65° C., or at least about 70° C. In one example, the plurality of NPPFs and CFSs are incubated with the sample at about 37° C., at about 42° C., or at about 50° C.

In some embodiments, the methods do not include nucleic acid purification (for example, nucleic acid purification is not performed prior to contacting the sample with the NPPFs and CFSs and/or nucleic acid purification is not performed following contacting the sample with the NPPFs and CFSs). In some examples, no pre-processing of the sample is required except for cell lysis. In some examples, cell lysis and contacting the sample with the plurality of NPPFs and CFSs occur sequentially. In other examples, cell lysis and contacting the sample with the plurality of NPPFs and CFSs occur concurrently, in some non-limiting examples without any intervening steps.

B. Treatment with Nuclease

Following hybridization of the NPPFs to target nucleic acids in the sample and to CFS(s), the sample is subjected to a nuclease protection procedure. The target nucleic acid molecules and CFSs (one or two CFSs, depending if there are both 5'- and 3'-flanking sequence on the NPPF or just one) which have hybridized to the NPPF are not hydrolyzed by the nuclease and can be subsequently sequenced (and optionally amplified).

Nucleases are enzymes that cleave a phosphodiester bond. Endonucleases cleave an internal phosphodiester bond in a nucleotide chain (in contrast to exonucleases, which cleave a phosphodiester bond at the end of a nucleotide chain). Thus, endonucleases, exonuclease, and combinations thereof, can be used in the disclosed methods. Endonucleases include restriction endonucleases or other site-specific endonucleases (which cleave DNA at sequence specific sites), DNase I, pancreatic RNAse, Bal 31 nuclease, S1 nuclease, mung bean nuclease, Ribonuclease A, Ribonuclease T1, RNase I, RNase PhyM, RNase U2, RNase CLB, micrococcal nuclease, and apurinic/apyrimidinic endonucleases. Exonucleases include exonuclease III and exonuclease VII. In particular examples, a nuclease is specific for single-stranded nucleic acids, such as S1 nuclease, P1 nuclease, mung bean nuclease, or BAL 31 nuclease. Reaction conditions for these enzymes are well-known in the art and can be optimized empirically.

Treatment with one or more nucleases can destroy all ss nucleic acid molecules (including RNA and DNA in the sample that is not hybridized to (thus not protected by) NPPFs, NPPFs that are not hybridized to target nucleic acid, and CFSs not hybridized to an NPPF), but will not destroy ds nucleic acid molecules such as NPPFs which have hybridized to CFSs and a target nucleic acid molecule present in the sample. For example, if the sample includes a cellular extract or lysate, unwanted nucleic acids, such as one or more of non-target genomic DNA (such as denatured genomic DNA), tRNA, rRNA, mRNA, miRNA, and portions of the target nucleic acid molecule(s) that are not hybridized to complementary NPPF sequences (such as overhangs), which in the case of mRNA or DNA nucleic acid targets will constitute the majority of the nucleic target sequence, can be substantially destroyed in this step. In some embodiments, this step leaves behind approximately a stoichiometric amount of target nucleic acid/CFS/NPPF duplex. If the target molecule is cross-linked to tissue that occurs from fixation, the NPPFs hybridize to the cross-linked target molecule without the need, in some embodiments, to reverse cross-linking, or otherwise release the target nucleic acid from the tissue to which it is cross-linked.

In some examples, S1 nuclease diluted in a buffer (such as one containing sodium acetate, NaCl, KCl, ZnSO$_4$, an antimicrobial agent (such as ProClin™ biocide), or combinations thereof) is added to the hybridized probe/sample mixture and incubated at about 37° C. to about 60° C. (such as about 50° C.) for 10-120 minutes (for example, 10-30 minutes, 30 to 60 minutes, 60-90 minutes, 90 minutes, or 120 minutes) to digest non-hybridized nucleic acid from the sample and non-hybridized NPPFs and CFSs. In one example, the nuclease digestion is performed by incubating the sample with the nuclease in a nuclease buffer at 50° C. for 60 to 90 minutes.

The samples can optionally be treated to inactivate or remove residual enzymes (e.g., by phenol extraction, precipitation, column filtration, addition of proteinase k, addition of a nuclease inhibitor, chelating divalent cations required by the nuclease for activity, or combinations thereof). In some examples the sample is treated to adjust the pH to about 7 to about 8, for example by addition of KOH or NaOH or a buffer (such as one containing Tris-HCl at pH 9 or Tris-HCl at pH 8). Raising the pH can prevent the depurination of DNA and also prevents many ss-specific nucleases (e.g., S1) from functioning fully. In some examples, the sample is heated (for example 80-100° C.) to inactivate the nuclease, for example for 10-30 minutes.

In some examples, following nuclease digestion, the sample is washed with a buffer that includes SSC, which can be followed by a more stringent wash (e.g., 50-60° C. water, 50 mM NaOH, or formamide).

C. Capture of Target

At some time during the method, the target nucleic acid molecule to be sequenced is retrieved or captured, which allows for separation of the target from other molecules in the reaction mixture. Examples of when the target can be captured are shown in FIGS. 2B-2D. Once the target is captured, it can remain captured during later steps of the method, or can be released when desired. In some examples, target is retrieved from the reaction by using a capture moiety present on the NPPF, 5CFS, or 3CFS. The capture moiety allows for physical separation of the target from non-tagged molecules in the reaction, such as portions of one or more of unbound NPPFs, unbound targets, and unbound CFS.

In one example, the capture moiety is covalently attached to the NPPF, 5CFS, or 3CFS. Examples of such attachments include an amine and carboxyl linkage (e.g., an amine group attached to the NPPF, 5CFS, or 3CFS, such as the 3'-end of the 5CFS (e.g., see FIG. 3), which can bind to a carboxyl group (e.g., carboxylic acid) on a capture moiety, such as a magnetic bead (e.g., Dynabeads)), and carbon-carbon bonds. In one example, the NPPF, 5CFS, or 3CFS includes an amine, and the capture moiety includes a primary aliphatic amine, aromatic amine, chloromethyl, amide, hydrazide, aldehyde, hydroxyl, thiol, or epoxy, which allows the nucleic acid molecule to be attached to the capture moiety. Other exemplary attachments are provided by Integrated DNA Technologies (for example see www.idtdna.com/pages/docs/default-source/technical-reports/strategies-for-attaching-oligonucleotides-to_v6-3-14-14.pdf?sfvrsn=2).

Examples of capture moieties that can be used with such linkages include but are not limited to beads (e.g., magnetic beads or polystyrene beads), agarose, sepharose, and the like, as well as plates (e.g., multi-well), slides (e.g., glass, which in some examples are coated with silane). In some examples, covalent attachment of the NPPF, 5CFS, or 3CFS to the capture moiety is used to capture the target during the hybridization step, and the target remains captured through at least the ligation step.

In another example, the capture moiety is non-covalently attached to the NPPF, 5CFS, or 3CFS. Examples of such attachments include a chemical group or label, such as avidin-biotin, streptavidin-biotin, neutravidin-biotin, digoxigenin/anti-digoxigenin (or any protein/antibody combination, such as protein A or protein G and their antibodies), glutathione, and hapten/protein. Thus, the reaction mixture containing the target and its hybridized NPPF, 5CFS, or 3CFS non-covalently attached to a capture moiety, is incubated with an appropriate solid support containing a complementary binding molecule (complementary to the capture moiety) under conditions that allow the capture moiety to bind to the solid support. Unbound materials can then be simply washed away or removed. For example, the capture moiety can include biotin. In such an example, the reaction mixture is incubated with a solid support (such as a bead or multiwell plate) that includes (e.g., is coated with) avidin, neutravidin or streptavidin. The target complex containing the biotin tag will bind to the avidin, neutravidin or streptavidin, allowing the untagged molecules in the reaction mixture to be removed (e.g., washed away). In another example, the capture moiety can include an amine. In such an example, the reaction mixture is incubated with a solid support (such as a bead or multiwell plate) that includes (e.g., is coated with) a carboxyl group (e.g., carboxycylic acid). The target complexes with the amine group will bind to the carboxyl groups, allowing the untagged molecules in the reaction mixture to be removed. In another example, the capture moiety can include digoxigenin or hapten. In such an example, the reaction mixture is incubated with a solid support (such as a bead or multiwell plate) that includes (e.g., is coated with) anti-digoxigenin antibodies or anti-hapten antibodies, respectively. The target complexes with the digoxigenin (or hapten) will bind to the anti-digoxigenin (or anti-hapten) antibodies, allowing the untagged molecules in the reaction mixture to be removed.

In some examples, the capture moiety includes both a solid support and a chemical group (e.g., carboxyl-terminated beads).

The presence of the scaffold allows the target (e.g., NPPF/target duplexes 214 of FIG. 2A) to be captured or retrieved from the reaction mixture. For example, the reaction can be centrifuged and washed, to allow for concentration and collection of the target. Or the scaffold to which the target is bound can be allowed to settle to the bottom of a vessel and washed. In another example, the scaffold is magnetic, which allows its collection (and collection of the target) using a magnet. In some examples, the target is retrieved by using filtration (e.g., by using a filter to capture beads). After the target is immobilized, the remainder of the reaction mixture can be removed (e.g., by washing). Appropriate reagents suitable for subsequent method steps can then be added to the target. In some examples, the target is captured without denaturing the target complex. Subsequent to capture, the target complexes attached to (or associated with, e.g., in a vessel) the solid support or scaffold can be released from (or removed from) the solid support. Alternatively, the target complexes can remain attached to (or associated with, e.g., in a vessel) the solid support and regents for the next step in the reaction added.

In some examples, capture is performed at room temperature (such as 15-35° C., such as 20-30° C. or 25-30° C., for at least 10 minutes, such as 10-120 minutes, 10-30 minutes, 30 to 60 minutes, 60-90 minutes, 30 minutes, or 60 minutes). In some examples following capture, one or more wash steps are performed, such as with SSC-T buffer (1×SSC, 0.02% TWEEN®-20 detergent).

Examples of solid supports that can be used with such attachments include but are not limited to beads (e.g., magnetic beads or polystyrene beads), agarose, sepharose, and the like, as well as plates (e.g., multi-well), and slides (e.g., glass, which in some examples are coated with silane). In some examples, non-covalent attachment of the NPPF, 5CFS, or 3CFS to the capture moiety is used to capture the target at a step subsequent to the hybridization step (but prior to ligation), and the target remains captured through at least the ligation step.

The capture moiety can be attached or conjugated directly or indirectly (e.g., via a spacer, such as a carbon spacer) to the 5CFS or 3CFS (or NPPF). The capture moiety can be attached to an internal nucleotide of the 5CFS or 3CFS (or NPPF). In one example, the capture moiety is attached to (or near, for example using a biotin-dT near, but not at the 3'-end) the 3'-end nucleotide of the 5CFS. In one example, the capture moiety is attached to (or near, for example using a biotin-dT near, but not at the 5'-end) the 5'-nucleotide of the 3CFS. In some examples, the capture moiety is not attached to the 5'-end nucleotide of the 5CFS or the 3'-end nucleotide of the 3CFS. In some examples, the capture moiety is attached indirectly to the 5CFS or 3CFS, for example by using a carbon spacer (such as about 6 to 60 carbon atoms, such as about 6, 7, 8, 9, 10, 11, 12, 24, 30, 36, 42, 48, 54, or 60 carbon atoms), bases with phosphothiorate linkages, biotin-avidin, or combinations thereof.

Solid supports that can be used with the disclosed methods and kits include those that allow access by detector reagents and a suitable surface affinity to immobilize capture reagents (e.g., oligonucleotides). Exemplary solid supports or scaffolds that can be used include, beads or particles (such as agarose, sepharose (or other matrix/resin), latex particle, polystyrene bead, superparamagnetic bead, or magnetic bead), multi-well plates (e.g., 96-, 384-, or 1536-well microtiter plate), the walls of wells of a reaction tray, test tubes, centrifuge tubes, membranes, and microparticles (such as latex particles). The solid support can be made of any suitable material, such as glass, plastic, membranes, metals, latex, agar, agarose, and the like. In some examples the solid support is an agarose bead or magnetic bead. In some examples the bead or particle is at least 1 μm, at least 2 μm, at least 3 μm, at least 4 μm, at least 10 μm, or at least 50 μm, such as 50 μm to 140μ, 1μ m to 2 μm, 1μ m to 3 μm, 1μ m to 4 μm, 1μ m to 5 μm, or 1 μm to 10μ m.

D. Ligation of CFS and Target and Optional Polymerization

After removing non-hybridized material, and recovering the NPPF/target duplexes, the target sequence (which can be DNA or RNA) is ligated to the CFSs (e.g., to the 5CFS, 3CFS, or both), thereby generating a ligated target. Thus, the "gap" between the target and each CFS (e.g., see FIGS. 3 and 4), is "closed" by use of a ligase. In some examples, a polymerase step is included, for example to replace nucleotides of the CFS or the target, which may have been removed by the nuclease. For example the nuclease my remove a few nucleotides (such as 1, 2, 3 or 4 nucleotides) from the 5'- and/or 3'-end of the CFS and/or the target. A polymerase can be included with the ligase, or polymerization can be performed prior to the ligation step.

A ligase is an enzyme that facilitates the joining of nucleic acid molecules together by catalyzing the formation of a phosphodiester bond. Examples include DNA ligase (e.g., EC 6.5.1.1) and RNA ligase (e.g., EC 6.5.1.3). Any ligase can be used, such as a T4 DNA ligase, T4 RNA ligase 1, T4 RNA ligase 2 (such as a truncated form), or Taq ligase. The ligase used may depend on the nucleotide (ribonucleotide or deoxyribonucleotide) present on the CFS that is closest to the target sequence, as well as the type of target sequence (e.g., DNA or RNA). For example, RNA will ligate to RNA, and DNA will ligate to DNA, and an RNA 3'-end will ligate to a DNA 5'-end. In some examples, the CFS includes a phosphate or other 5'-end modification to ensure the ligase has the proper substrate. For example, a CFS (e.g., 210 in FIG. 2A) can be a DNA molecule including 1 or more RNA bases at the 3'-end. For example, a CFS (e.g., 208 in FIG. 2A) can be an RNA molecule including 1 or more DNA bases at the 5'-end. In some examples, a combination of ligases is used. In some examples, separate ligations (which optionally includes polymerization) are used when the targets include both DNA and RNA molecules, while in other examples a single ligation (which optionally includes polymerization) is used when the targets include both DNA and RNA molecules. Some non-limiting examples are shown below.

| | DNA target only | | RNA target only | | Combination DNA and RNA target | |
|---|---|---|---|---|---|---|
| | 5'CFS | 3'CFS | 5'CFS | 3'CFS | 5'CFS | 3'CFS |
| RNA LIGASES | | | | | | |
| T4 RNA ligase 2 truncated or with mutations | RNA, target 5' pre-adenylated | | RNA, target 5' pre-adenylated | DNA or RNA, 5' pre-adenylated | | |
| T4 RNA Ligase 1 | DNA or RNA | DNA, 5' phosphorylated | RNA | DNA or RNA, 5' phosphorylated or 5' pre-adenylated | RNA | DNA, 5' phosphorylated or 5' pre- |

|  | DNA target only | | RNA target only | | Combination DNA and RNA target | |
| --- | --- | --- | --- | --- | --- | --- |
|  | 5'CFS | 3'CFS | 5'CFS | 3'CFS | 5'CFS | 3'CFS |
| T4 RNA Ligase 2 | RNA | DNA 5' phosphorylated | RNA | DNA or RNA, 5' phosphorylated | RNA | adenylated DNA, 5' phosphorylated |
| 5'App DNA/RNA Ligase | target is 5' pre adenylated | DNA, 5' pre-adenylated | Target 5' pre-adenylated | DNA or RNA, 5' pre-adenylated | target 5' pre-adenylated | DNA, 5' pre-adenylated |
| DNA LIGASES | | | | | | |
| SplintR Ligase | DNA | DNA, 5' phosphorylated | | | | |
| T3 DNA Ligase | DNA | DNA, 5' phosphorylated | RNA | RNA, 5' phosphorylated | | |
| T4 DNA Ligase | DNA or RNA | DNA, 5' phoshoprylated | RNA | DNA or RNA, 5' phosphorylated | RNA | DNA, 5' phosphorylated |
| Taq Ligase/Ampligase 9N DNA Ligase | DNA or RNA | DNA, 5' phosphorylated | | | | |
| *E. coli* Ligase | DNA | DNA, 5' phosphorylated | | | | |

T4 DNA ligase is an ATP-dependent enzyme that catalyzes the formation of a phosphodiester bond between juxtaposed 5' phosphoryl (such as one present on a 5CFS and one present on a target DNA or RNA following nuclease digestion, e.g., see FIGS. 3 and 4) and 3'-hydroxyl termini (such as one present on a 3CFS and one present on a target DNA or RNA, e.g., see FIGS. 3 and 4) in duplex DNA or RNA. T4 DNA ligase can also repair single-stranded nicks in duplex DNA, RNA, or DNA/RNA hybrids. T4 DNA ligase can also join both blunt-end and cohesive-end fragments of duplex DNA or RNA.

Taq DNA ligase catalyzes the formation of a phosphodiester bond between juxtaposed 5' phosphate (such as one present on a 5CFS and one present on a target DNA or RNA following nuclease digestion, e.g., see FIGS. 3 and 4) and 3' hydroxyl termini (such as one present on a 3CFS and one present on a target DNA, e.g., see FIGS. 3 and 4) of two adjacent oligonucleotides which are hybridized to a complementary target DNA. The ligation occurs when the oligonucleotides are perfectly paired to the complementary target DNA and have no gaps between them. Taq DNA Ligase is active at elevated temperatures (45° C.-65° C.).

T4 RNA ligase 1 (ssRNA ligase) catalyzes the ligation of a 5' phosphoryl-terminated nucleic acid donor (such as one present on a 5CFS and one present on a target DNA or RNA following nuclease digestion, e.g., see FIGS. 3 and 4) to a 3' hydroxyl-terminated nucleic acid acceptor (such as one present on a 3CFS and one present on a target DNA or RNA, e.g., see FIGS. 3 and 4) through the formation of a 3'→5' phosphodiester bond, with hydrolysis of ATP to AMP and PPi. Substrates include single-stranded RNA and DNA as well as dinucleoside pyrophosphates.

T4 RNA ligase 2, also known as T4 Rn1-2, has both intermolecular and intramolecular RNA strand joining activity. It catalyzes the ligation of a 5' phosphate (such as one present on a target DNA or RNA following nuclease digestion, e.g., see FIGS. 3 and 4) to a 3' hydroxyl (such as one present on a 3CFS, e.g., see FIGS. 3 and 4). T4 RNA Ligase 2 can also ligate the 3' hydroxyl of RNA to the 5' phosphate of DNA. In some examples, a truncated form of T4 RNA ligase 2 is used (e.g., amino acids 1-249).

In some examples, a ligase is diluted in a buffer (such as one containing essential cofactors such as NAD+ or ATP, a buffering agent, and cations is added to the mixture containing NPPF/target duplexes and incubated at about 4° C.-60° C. (depending on the ligase) (such as at least 4° C., at least 20° C., at least 25° C., at least 30° C., at least 37° C., at least 50° C., or at least 60° C., such as 4 to 37° C., 4 to 25° C., or 20 to 25° C.) for at least 15 minutes, at least 30 minutes, at least 1 hour, at least 2 hours, at least 4 hours, at least 6 hours, at least 12 hours, or at least 16 hours, to ligate the CFSs to the target nucleic acid molecule (wherein the CFSs and target are already hybridized to an NPPF). In one example, a buffer for T4 DNA ligase includes 50 mM Tris-HCl, pH 7.5, 10 mM $MgCl_2$, 10 mM dithiothreitol, 1 mM ATP.

A polymerase is an enzyme that can synthesize a chain of nucleic acid molecules or a nucleic acid polymer, for example by adding one or more nucleotides to the end of a nucleic acid molecule. Examples include DNA polymerase (EC 2.7.7.7) and RNA polymerase (EC 2.7.7.6). DNA polymerases can be used to extend a DNA molecule at its 3'-end, that is, add nucleotides to its 3'-end. In one example, a DNA polymerase is used, such as T4 or T7 DNA polymerase or an exonuclease-free thermostable polymerase, in the presence of dNTPs. RNA polymerases can be used to extend an RNA molecule at its 3'-end, that is, add ribonucleotides to its 3'-end. In one example, an RNA polymerase is used, such as *E. coli* RNA polymerase, with rNTPs added. If an RNA polymerase is used, the method can further include a reverse transcription step (e.g., at the time of PCR amplification of the ligated target). In some examples, for example if the target nucleic acid molecules include both DNA and RNA, both a DNA polymerase and an RNA polymerase are used.

In some examples, the polymerization reaction is performed before the ligation reaction. For example the captured target can be incubated with a polymerase and dNTPs and/or rNPTs at about 4° C.-60° C. (such as at least 4° C., at least 20° C., at least 25° C., at least 30° C., at least 37° C., at least 50° C., or at least 60° C., such as 4° C. to 37° C., 4° C. to 25° C., or room temperature (20 to 25° C.)) for at least 15 minutes, at least 30 minutes, at least 1 hour, at least 2 hours, at least 4 hours, at least 6 hours, at least 12 hours, or at least 16 hours. In one example, the polymerase is T4 DNA Polymerase and the incubation conditions are at 37° C. for 1 hour. In one example, the polymerase is T4 DNA Polymerase and the incubation is performed at room temperature (such as 20-25° C.) for 30 minutes.

In some examples, a polymerase is added to the ligation reaction, for example along with dNTPs and/or rNPTs and incubated at about 4° C.-60° C. (depending on the ligase) (such as at least 4° C., at least 16° C., at least 20° C., at least 25° C., at least 30° C., at least 37° C., at least 50° C., or at least 60° C., such as 4 to 37° C., 4 to 25° C., or 20 to 25° C.) for at least 15 minutes, at least 30 minutes, at least 1 hour, at least 2 hours, at least 4 hours, at least 6 hours, at least 12 hours, or at least 16 hours. In one example, the polymerization/ligation reaction is incubated at room temperature (such as 20 to 25° C.) for at least 15 minutes, at least 30 minutes, or at least 1 hour, such as 30-60 minutes.

E. Separation of NPPF from the Ligated Target

After ligating the CFS(s) to the target, and forming ligated targets, the NPPF is separated (e.g., denatured) from the ligated target. Thus, the double stranded NPPF/target complex can be separated into two single stranded nucleic acid molecules, the ss NPPF and the ss ligated target. In some examples, NPPF is separated from the ligated target by degrading the NPPF with a DNase (e.g., where the NPPF is DNA, the target is RNA, and the CFSs are RNA), thereby leaving the ligated target. In some examples, NPPF is separated from the ligated target by degrading the NPPF with a RNase (e.g., where the NPPF is RNA, the target is DNA, and the CFSs are DNA), thereby leaving the ligated target. This step can also remove unligated nucleic acid molecules (e.g., unligated CFS) via physical separation.

In one example, the reaction is heated, for example in the presence of a wash buffer, under conditions that allow the NPPF to dissociate from the ligated target, resulting in a mixed population of ss NPPFs and ss ligated targets. For example, the reaction can be heated in an aqueous solution. In one example, the reaction is heated to at least about 50° C. (such as 50 to 100° C., for example 50° C.) in water, and incubated for at least ten minutes. In some examples, the reaction is subjected to three 10 minute washes with water at about 50° C. In one example, the reaction is washed three times for 10 minutes in 0.02% TWEEN® non-ionic detergent in water at about 50° C. (the detergent can be added to prevent beads from clumping). In another example, the reaction is heated to at least 90° C., such as about 98° C. in 100% formamide solution for at least ten minutes. In some examples, the addition of solution and heating steps are repeated (such as 1 to 5 times), providing subsequent washes to substantially remove the NPPF and unligated species and wash them away from the ss ligated product. In some examples, the reaction is washed with 50% formamide/0.02% TWEEN® non-ionic detergent at room temperature.

In another example, denaturation is performed by altering the pH with a base (such as KOH or NaOH), allowing the NPPF to dissociate from the ligated target, resulting in a mixed population of ss NPPFs and ss ligated targets. For example, NaOH can be added to a final concentration of 50 mM to 2M (such as 100 mM) and incubated for at least 10 minutes at room temperature. In some examples, the addition of NaOH and incubation is repeated (such as 1 to 5 times). Following the base washes, the reaction can be resuspended in an aqueous buffer, such as Tris-HCl, or the reaction neutralized with an equal-normal amount of an appropriate acid solution of buffered solution.

In some examples, the sample is incubated with a DNAse, for example at a concentration of at least 1 unit DNase I per sample (such as at least 5 units, at least 10 units, or at least 20 units, such as 1 to 10 units, 1 to 20 units, or 5, 6, 7, 8, 9 or 10 units), for at least 10 minutes, at least 30 minutes, at least 60 minutes, or at least 120 minutes, such as 10 minutes, 30 minutes, 60 minutes, 90 minutes, or 2 hours, at 37° C.

In some examples, the sample is incubated with a RNAse, such as RNase H, for example at a concentration of at least 1 unit RNase H per sample (such as at least 5 units, at least 10 units, at least 20 units, or at least 50 units, such as 1 to 10 units, 1 to 20 units, or 1 to 50 units, such as 5, 6, 7, 8, 9, 10, 20, 30, 40 or 50 units), for at least 10 minutes, at least 30 minutes, at least 60 minutes, or at least 120 minutes, such as 10 minutes, 30 minutes, 60 minutes, 90 minutes, or 2 hours, at 37° C.

F. Capture of the Ligated Target

The ss ligated target can be retrieved, for example by using the capture moiety on the CFS (which is ligated to the target), using methods similar to those described above in section II. C. In some examples, following the capture, the sample is washed with a buffer that includes SSC (such as SSC-T), which can be followed by a more stringent wash (e.g., 50-60° C. water, 50 mM NaOH, or formamide) or by a wash that includes TWEEN® non-ionic detergent. The resulting ss ligated target can then be sequenced. In some examples, the ss ligated target is amplified prior to sequencing, thereby generating ligated target amplicons.

G. Optional Amplification of Ligated Targets

The resulting captured ligated target molecules can be amplified prior to sequencing, for example using methods such as polymerase chain reaction (PCR) or other forms of enzymatic amplification or ligation based methods of amplification. If the target is RNA, or if an RNA Polymerase was used (see section D above) with rNTPs, a reverse transcription step can be included.

In some examples, no more than 30 cycles of amplification are performed, such as no more than 25 cycles of amplification, no more than 20 cycles of amplification, no more than 15 cycles of amplification, no more than 10 cycles of amplification, no more than 8 cycles of amplification, or no more than 5 cycles of amplification, such as 2 to 30 cycles, 5 to 30 cycles, 8 to 30 cycles, 8 to 25 cycles, 2 to 25 cycles, 5 to 25 cycles, 5 to 20 cycles, 5 to 15 cycles, or 5 to 10 cycles of amplification.

Nucleic acid amplification methods that can be used include those that result in an increase in the number of copies of a nucleic acid molecule, such as a ligated target or portion thereof. The resulting products are called amplification products or amplicons. Generally, such methods include contacting material to be amplified (e.g., ligated target) with one or a pair of oligonucleotide primers, under conditions that allow for hybridization of the primer(s) to the nucleic acid molecule to be amplified. The primers are extended under suitable conditions, dissociated from the template, and then re-annealed, extended, and dissociated to amplify the number of copies of the nucleic acid molecule.

Examples of in vitro amplification methods that can be used include, but are not limited to, PCR, reverse-transcription PCR (RT-PCR), quantitative real-time PCR, quantitative real-time reverse transcriptase PCR, isothermal amplification methods, strand displacement amplification; transcription-free isothermal amplification; repair chain reaction amplification; and NASBA™ RNA transcription-free amplification. In one example, a ligation-based method of amplification is used, wherein the primers specifically hybridize to at least a portion of the CFSs. Ligation can be enzymatic or non-enzymatic. In one example, helicase-dependent amplification is used.

During amplification of the ligated target, an experiment tag, and/or sequencing adaptor can be incorporated as, for instance, part of the primer and extension constructs, (see FIG. 5). However, addition of such tags/adpators is optional. For example, an amplification primer, which includes a first portion that is complementary to all or part of a 5CFS or 3CFS, can include a second portion that is complementary to a desired experiment tag and/or sequencing adaptor. One skilled in the art will appreciate that different combinations of experiment tags and/or sequencing adaptors can be added to either end of the ligated target. In one example, the ligated target is amplified using a first amplification primer that includes a first portion complementary to all or a portion of the 5CFS and a second portion complementary to (or comprising) a desired sequencing adaptor, and the second amplification primer includes a first portion complementary to all or a portion of the 3CFS and a second portion complementary to (or comprising) a desired experiment tag (e.g., see FIG. 5). In one example, two different sequencing adapters and two different experiment tags are used. In some examples, two different sequencing adapters and one experiment tag are used. In another example, the ligated target is amplified using a first amplification primer that includes all or a portion of a first portion complementary to the 5CFS and a second portion complementary to (or comprising) a desired sequencing adaptor and a desired experiment tag, and the second amplification primer includes a first portion complementary to all or a portion of the 3CFS and a second portion complementary to (or comprising) a desired experiment tag.

Amplification can also be used to introduce a detectable label into the generated ligated target amplicons (for example if additional labeling is desired), or other molecule that permits detection or quenching. For example, the amplification primer can include a detectable label, hapten, or quencher which is incorporated into the ligated target during amplification. Such a label, hapten, or quencher can be introduced at either end of the ligated target amplicon (or both ends), or anywhere in between.

In some examples, the resulting ligated target amplicons are purified before sequencing. For example, the amplification reaction mixture can be purified before sequencing using known in the art (e.g., gel purification, biotin/avidin capture and release, capillary electrophoresis, size-exclusion purification, or binding to and release from paramagnetic beads (solid phase reversible immobilization)). In one example, the ligated target amplicons are biotinylated (or include another hapten) and captured onto an avidin or anti-hapten coated bead or surface, washed, and then released for sequencing. Likewise, the ligated target amplicons can be captured onto a complimentary oligonucleotide (such as one bound to a surface), washed and then released for sequencing. The capture of amplicons need not be particularly specific, as the disclosed methods eliminate most of the genome or transcriptome, leaving the ligated target. Other methods can be used to purify the amplified product, if desired.

The amplified products can also be purified after the last step of amplification, while still double stranded, by a method which uses a nuclease that hydrolyzes single stranded oligonucleotides (such as Exonuclease I), which nuclease can in turn be inactivated before continuing to the next step such as sequencing.

1. Primers that Bind the CFS

The amplification primers that specifically bind or hybridize to the CFSs (5CFS, 3CFS) can be used to initiate amplification, such as PCR amplification. Thus, primers can be annealed to a complementary sequence in the CFS by nucleic acid hybridization to form a hybrid between the primer and the CFS of the ligated target, and then the primer extended along the complement strand by a polymerase enzyme. In addition, the amplification primers can be used to introduce nucleic acid markers (such as one or more experiment tags and/or sequencing adaptors) and/or detectable labels to the resulting ligated target amplicons. Primers are short nucleic acid molecules, such as a DNA oligonucleotides that are at least 12 nucleotides in length (such as about 15, 20, 25, 30, 50, 60, 61, 62, 63, 64, 65, 66, 67, 68, 69, 70, 75 or 80 nucleotides or more in length, such as 15 to 25 nt, 50 to 80 nt, 60-70 nt or 62-66 nt). For example, such primers can have a portion complementary to the CFS (such as at least 10 at least 15, at least 20, or at least 25 nt complementary to the CFS). In some examples the primers include a detectable label, such as a fluorophore or biotin, which gets incorporated into the ligated target amplicons.

For example, in addition to the amplification primer having a region complementary to the CFS, it can also include a second region having a nucleic acid sequence that results in addition of an experiment tag, sequencing adaptor, detectable label, or combinations thereof, to the resulting ligated target amplicon. An experiment tag and/or sequencing adaptor can be introduced at the 5'-and/or 3'-end of the ligated target. In some examples, two or more experiment tags and/or sequencing adaptors are added to a single end or both ends of the ligated target amplicon, for example using a single primer having a nucleic acid sequence that results in addition of two or more experiment tags and/or sequencing adaptors. Experiment tags can be used, for example, to differentiate one sample or sequence from another. Sequence adaptors permit capture of the resulting ligated target amplicon by a particular sequencing platform.

2. Addition of Experiment Tags

Experiment tags are short sequences or modified bases that serve as an identifier for one or several reactions to be independently discerned by, for example: patient, sample, cell type, time course timepoint, or treatment. Experiment tags can be part of the CFS. In another example, the experiment tag is added later, for example during amplification of the ligated target, resulting in a ligated target amplicon containing an experiment tag. The presence of universal sequences in the CFS permit the use of universal primers, which can introduce other sequences onto the ligated target, for example during amplification. Experimental tags can also be used for amplification, such as nested amplification, or two stage amplification.

Experiment tags, such as one that differentiates one sample from another, can be used to identify the particular target sequence. Thus, experiment tags can be used to distinguish experiments or patients from one another. In one example, the experiment tag is the first three, five, ten, twenty, or thirty nucleotides of the 5'- and/or 3'-end of the ligated target amplicon. In some examples, the experiment tags are placed in proximity to the sequencing primer site. For ILLUMINA® sequencing, experiment tags are immediately next to the Read1 and Read 2 primer sites. For IonTorrent® sequencing, experiment tags are generally the first few bases read. In particular examples, the experiment tag is at least 3 nucleotides in length, such as at least 5, at least 10, at least 15, at least 20, at least 25, at least 30, at least 40, or at least 50 nucleotides in length, such as 3-50, 3-20, 12-50, 6-8, 6-12, or 12-30 nucleotides, for example, 3, 5, 6, 7, 8, 9, 10, 11, 12, 20, 21, 22, 23, 24, 25, 26, 27, 28, 29 or 30 nucleotides in length.

In one example an experiment tag is used to differentiate one sample from another. For example, such a sequence can function as a barcode, to allow one to correlate a particular sequence detected with a particular sample, patient, or experiment (such as a particular reaction well, day or set of reaction conditions). This permits a particular ligated target that is sequenced to be associated with a particular patient or sample or experiment for instance. The use of such tags provides a way to lower cost per sample and increase sample throughput, as multiple ligated target amplicons can be tagged and then combined (for example from different experiments or patients), for example in a single sequencing run or detection array. This allows for the ability to combine different experimental or patient samples into a single run, within the same instrument channel or sequencing consumable (such as a flow cell or a semiconductor chip). For example, such tags permitting 100's or 1,000's of different experiments to be sequenced in a single run, within a single flow cell or chip. In addition, if the method includes the step of gel purifying the completed amplification reaction (or other method of purification or clean up that does not require actual separation) only one gel (or clean up or purification reaction or process) is needed to be run per detection or sequencing run. The sequenced ligated target amplicons can then be sorted, for example by the experiment tags.

In one example the experiment tag is used to identify the particular target sequence. In this case, using an experimental tag to correspond to a particular target sequence can shorten the time or amount of sequencing needed, as sequencing the end of the ligated target instead of the entire ligated target can be sufficient. For example, if such an experiment tag is present on the 3'-end of the ligated target amplicon, the entire ligated target amplicon sequence itself does not have to be sequenced to identify the target sequence. Instead, only the 3'-end of the ligated target amplicon containing the experiment tag needs to be sequenced. This can significantly reduce sequencing time and resources, as less material needs to be sequenced.

3. Addition of Sequencing Adaptors

Sequencing adaptors can, but need not, be part of the CFS when generated. In another example, the sequencing adaptor is added later, for example during amplification of the ligated target, resulting in a ligated target amplicon containing a sequencing adaptor. The presence of a universal sequence in the CFS permit the use of universal primers, which can introduce other sequences onto the ligated target, for example during amplification.

A sequencing adaptor can be used add a sequence to a ligated target (or amplicon thereof) needed for a particular sequencing platform. For example, some sequencing platforms (such as the 454-branded (Roche), ION TORRENT®-branded and ILLUMINA®-branded) require the nucleic acid molecule to be sequenced to include a particular sequence at its 5'- and/or 3'-end, for example to capture the molecule to be sequenced. For example, the appropriate sequencing adaptor is recognized by a complementary sequence on the sequencing chip or beads, and the ligated target (or amplicon thereof) captured by the presence of the sequencing adaptor.

In one example, a poly-A (or poly-T), such as a poly-A or poly-T at least 10 nucleotides in length, is added to the ligated target during PCR amplification. In a specific example, the poly-A (or poly-T) is added to the 3'-end of the ligated target. In some examples, this added sequence is poly-adenylated at its 3' end using a terminal deoxynucleotidyl transferase (TdT).

In particular examples, the sequencing adapter added is at least 12 nucleotides (nt) in length, such as at least 15, at least 20, at least 25, at least 30, at least 40, at least 50, at least 60 or at least 70 nt in length, such as 12-50, 20-35, 50-70, 20-70, or 12-30 nt in length.

H. Sequencing of Ligated Target or Ligated Target Amplicons

The ligated target or ligated target amplicons are sequenced, for example by sequencing the entire ligated target or ligated target amplicon, or a portion thereof (such as an amount sufficient to permit identification of the target nucleic acid molecule or to permit determination that a particular mutation is or is not present). The disclosure is not limited to a particular sequencing method. It will be appreciated that the ligated target or ligated target amplicons can be designed for sequencing by any method, on any sequencer known currently or in the future. The ligated target itself does not limit the method of sequencing used, nor the enzyme used. Other methods of sequencing are or will be developed, and one skilled in the art can appreciate that the generated ligated target or ligated target amplicons will be suitable for sequencing on these systems. In some examples, multiple different ligated targets or ligated target amplicons are sequenced in a single reaction. Thus, a plurality of ligated targets can be sequenced in parallel, for example simultaneously or contemporaneously.

Exemplary sequencing methods that can be used to determine the sequence of the resulting ligated target or ligated target amplicons, such as one composed of DNA, include but are not limited to, the chain termination method, dye terminator sequencing, and pyrosequencing (such as the methods commercialized by Biotage (for low throughput sequencing) and 454 Life Sciences (for high-throughput sequencing)). In some examples, the ligated target or ligated target amplicons are sequenced using an ILLUMINA® (e.g., HiSeq), ION TORRENT®, 454®, Helicos, PacBio®, Solid® (Applied Vioasystems) or any other commercial sequencing system. In one example, the sequencing method uses bridge PCR (e.g., ILLUMINA® method). In one example, the Helicos® or PacBio® single molecule sequencing method is used. In one example, next-generation sequence (NGS) is used, such as those from ILLUMINA®, Roche, or Thermo Fisher Scientific, for example, SOLID/ION TORRENT® PGM from Thermo Fisher Scientific, Genome Analyzer/HiSeq 2000/MiSeq from ILLUMINA®, GS FLX Titanium/GS Junior from Roche, or a Qiagen GeneReader™ system. Sequencing adaptors (such as a poly-A or poly T tails present on the ligated target or ligated target amplicons, for example introduced using PCR) can be used for capture of the ligated target or ligated target amplicons for sequencing on a particular platform. In one example, a nanopore-type sequencer is used.

Although sequencing by 454® or ILLUMINA® methods typically involves nucleic acid preparation, accomplished by random fragmentation of nucleic acid, followed by in vitro ligation of common adaptor sequences, for the disclosed methods, the step of random fragmentation of the nucleic acid to be sequenced can be eliminated, and the in vitro ligation of adaptor sequences can be to the ligated target or ligated target amplicons, such as an experiment tag present in the ligated target or ligated target amplicons. For 454® sequencing, a sequencing primer is hybridized to the ligated target after amplification on the sequencing chip/bead amplicon.

I. Controls

In some embodiments, the method includes the use of one or more positive and/or negative controls. In some examples, the control(s) is subjected to the same reaction conditions as the actual experimental NPPFs and corresponding CFSs. The use of tagging permits actual different samples to be used as controls but processed for sequencing and run in the same sequencing lane as test samples.

In some examples, the control is a "positive control" NPPF included in the plurality of NPPFs and corresponding CFSs that a sample is contacted with. In some examples, this positive control is an internal normalization control for variables such as the number of cells lysed for each sample, the recovery of DNA or RNA, or the hybridization efficiency. In one example, DNA is measured as a control for the number of cells when measuring target RNA. In some examples the positive control includes one or more NPPFs and corresponding CFSs specific for a DNA or RNA known to be present in the sample (for example a nucleic acid sequence likely to be present in the species being tested, such as one or more basal level or constitutive housekeeping genes, or repetitive DNA elements). Exemplary positive control targets include, but are not limited to, structural genes (e.g., actin, tubulin, or others) or DNA binding proteins (e.g., transcription regulation factors, or others), as well as housekeeping genes. In some examples, a positive control target includes one or more NPPFs and corresponding CFSs specific for glyceraldehyde-3-phosphate dehydrogenase (GAPDH), peptidylproylyl isomerase A (PPIA), large ribosomal protein (RPLPO), ribosomal protein L19 (RPL19), SDHA (succinate dehydrogenase), HPRT1 (hypoxanthine phosphoribosyl transferase 1), HBSIL (HBS1-like protein), ß-actin (ACTB), 5-Aminolevulinic acid synthase 1 (ALAS1), B-2 microglobulin (B2M), alpha hemoglobin stabilizing protein (AHSP), ribosomal protein S13 (RPS13), ribosomal protein S20 (RPS20), ribosomal protein L27 (RPL27), ribosomal protein L37 (RPL37), ribosomal protein 38 (RPL38), ornithine decarboxylase antizyme 1 (OAZ1), polymerase (RNA) II (DNA directed) polypeptide A, 220 kDa (POLR2A), thioredoxin like 1 (TXNL1), yes-associated protein 1 (YAPI), esterase D (ESD), proteasome (prosome, macropain) 26S subunit, ATPase, 1 (PSMC1), eukaryotic translation initiation factor 3, subunit A (EIF3A), or 18S rRNA. In some examples, the positive control targets are repetitive DNA elements such as HSATI, ACRO1, and LTR3. In some examples, the positive control targets are single-copy genomic DNA sequences (assuming a haploid genome). For example, the corresponding positive control NPPFs and corresponding CFSs can be added to the sample prior to or during hybridization with the plurality of test NPPFs and corresponding CFSs. In some examples, a positive control includes one or more NPPFs and corresponding CFSs, whose complement is a spiked in (e.g., added) target nucleic acid molecule (such as one or more in vitro transcribed nucleic acids, nucleic acids isolated from an unrelated sample, or synthetic nucleic acids such as a DNA or RNA oligonucleotide) added to the sample prior to or during hybridization with the plurality of NPPFs and corresponding CFSs. In one example, the positive control NPPFs and spike ins have a single nucleotide mismatch. In one example, a plurality of NPPFs and spike ins are added, with the spike ins added at a range of known concentrations (such as 1 pM, 10 pM, and 100 pM) that form a "ladder" of input and demonstrate the dynamic range of the assay in the final sequencing output.

In some examples, a "negative control" includes one or more NPPFs and corresponding CFSs, whose complement is known to be absent from the sample, for example as a control for hybridization specificity, such as a nucleic acid sequence from a species other than that being tested, e.g., a plant nucleic acid sequence when human nucleic acids are being analyzed (for example, *Arabidopsis thaliana* AP2-like ethylene-responsive transcription factor (ANT)), or a nucleic acid sequence not found in nature.

In some examples, the control is used to determine if a particular step in the method is operating properly. In some examples, the positive or negative controls are assessed in the final sequencing results. In one example, the control includes an analysis following capture of the target, but prior to its sequencing (e.g., between steps 4 and 5 in FIG. 2A). In one such example, this analysis includes the use of TAQMAN® probes for the negative control probes to assess the effectiveness of the nuclease within the assay. All negative control probe should be removed by the nuclease step, therefore if the amount of negative control probe is high, it may indicate that the nuclease protection did not perform properly and that the sample may be compromised. In another such example, the TAQMAN® assay for negative control probes is combined with a simultaneous measurement quantification of the amount of the entire captured target (i.e., using SYBR®-based qPCR methods).

In one example, the sample to be analyzed is exposed to amplification conditions (e.g., qPCR or qRT-PCR) prior to performing the disclosed methods, to determine if the sample has a sufficient amount of (and quality of) nucleic acid molecules. For example, qPCR may be performed using primers that amplify a target region of interest such as KRAS or BRAF, a housekeeper RNA gene such as GAPDH, or a repetitive DNA element such as LTR3 to determine the assessable nucleic acid within the sample. In one example, the primers are designed such that they amplify a region close to the size of the target region, to determine whether available nucleic acid is large enough to be assessed-nucleic acid fragments that are smaller than the target site for of a given NPPF will not be assessed, as they will not protect the NPPF during nuclease digestion. In one example, the range of acceptable sample amounts and qualities is determined experimentally, for example using a particular sample type (e.g., lung or melanoma samples) or format (e.g., formalin fixed tissues or cell lines).

III. Nuclease Protection Probes with Flanking Sequences (NPPFs)

The disclosed methods permit direct sequencing of one or more target nucleic acid molecules, for example simultaneously or contemporaneously. Based on the target nucleic acid, NPPFs can be designed for use in the disclosed methods using the criteria set forth herein in combination with the knowledge of one skilled in the art. In some examples, the disclosed methods include generation of one or more appropriate NPPFs for detection of particular target nucleic acid molecules. The NPPF, under a variety of conditions (known or empirically determined), specifically binds (or is capable of specifically binding, e.g., specifically hybridizing) to a target nucleic acid or portion thereof, if such target is present in the sample.

FIG. 1A shows an exemplary NPPF 100 having a region 102 that includes a sequence that specifically binds to or hybridizes to the target nucleic acid sequence(s), as well as flanking sequences 104, 106 at the 5'- and 3'-end of the NPPF, respectively, wherein the flanking sequences bind or hybridize to their complementary sequences (referred to herein as CFSs). Although two flanking sequences are shown, in some examples the NPPF has only one flanking sequence, such as one at the 5'-end or one at the 3'-end. In some examples, the NPPF includes two flanking sequences: one at the 5'-end and the other at the 3'-end. In some examples, the flanking sequence at the 5'-end differs from the flanking sequence at the 3'-end. FIG. 1B shows an embodiment of an NPPF 120 that is composed of two separate nucleic acid molecules 128, 130. In one example, the NPPF is 100 nt, 25 nt for each flanking sequence 104, 106, and 50 nt for the region 102 that specifically binds to or hybridizes to the target nucleic acid sequence(s).

The NPPF (as well as CFSs that bind to the NPPFs) can be any nucleic acid molecule, such as a DNA or RNA molecule, and can include unnatural bases. Thus, the NPPFs (as well as CFSs that bind to the NPPFs) can be composed of natural (such as ribonucleotides (RNA), or deoxyribonucleotides (DNA)) or unnatural nucleotides (such as locked nucleic acids (LNAs, see, e.g., U.S. Pat. No. 6,794,499), peptide nucleic acids (PNAs)), and the like. The NPPFs can be single- or double-stranded. In one example, the NPPF is a ss DNA and the CFS(s) is/are RNA (e.g., and the target is RNA). In one example, the NPPF is a ss RNA and the CFS(s) is/are DNA (e.g., and the target is DNA). In some examples, the NPPFs (as well as CFSs that bind to the NPPFs) include one or more synthetic bases or alternative bases (such as inosine). Modified nucleotides, unnatural nucleotides, synthetic, or alternative nucleotides can be used in NPPFs at one or more positions (such as 1, 2, 3, 4, 5, or more positions). For example, NPPFs and/or CFSs can include one or more nucleotides containing modified bases, and/or modified phosphate backbones. In some examples, use of one or more modified or unnatural nucleotides in the NPPF can increase the $T_m$ of the NPPF relative to the $T_m$ of a NPPF of the same length and composition which does not include the modified nucleic acid. One of skill in the art can design probes including such modified nucleotides to obtain a probe with a desired $T_m$. In one example, an NPPF is composed of DNA or RNA, such as single stranded (ssDNA) or branched DNA (bDNA). In one example, an NPPF is an aptamer.

The NPPFs include a region that is complementary to one or more target nucleic acid molecules. NPPFs used in the same reaction can be designed to have similar Tm's. In one example, at least one NPPF is present in the reaction that is specific for a single target nucleic acid sequence. In such an example, if there are 2, 3, 4, 5, 6, 7, 8, 9 or 10 different target nucleic acid sequences to be detected or sequenced, the method can correspondingly use at least 2, 3, 4, 5, 6, 7, 8, 9 or 10 different NPPFs (wherein each NPPF corresponds to/has sufficient complementarity to hybridize to a particular target). Thus in some examples, the methods use at least two NPPFs, wherein each NPPF is specific for a different target nucleic acid molecule. However, one will appreciate that several different NPPFs can be generated to a particular target nucleic acid molecule, such as many different regions of a single target nucleic acid sequence. In one example, an NPPF includes a region that is complementary to a sequence found only in a single gene in the transcriptome.

However, some examples, a single NPPF is present in the reaction that is specific for two or more target nucleic acid sequences, such as a wild type sequence and one or more mutant sequences for a particular gene (e.g., see FIG. 10). Thus, in some examples, if there are 2, 3, 4, 5, 6, 7, 8, 9 or 10 different target genes (such as BRAF, KRAS and EGFR), each with two or more target nucleic acid sequences to be detected or sequenced, the method can correspondingly use at least 2, 3, 4, 5, 6, 7, 8, 9 or 10 different NPPFs (wherein each NPPF corresponds to a particular gene, but can detect multiple variations of the gene sequence).

Combinations of these types of NPPFs can be used in a single reaction, such as (1) one or more NPPFs each having specificity (e.g., complementarity) for a single target nucleic acid sequence (e.g., can only sufficiently hybridize to a single target nucleic acid molecule), and (2) one or more NPPFs each having specificity (e.g., complementarity) for a single target gene, but with the ability to detect a plurality of variations in that gene (e.g., can sufficiently hybridize to two or more variations of the target gene, such as the wild type sequence and at least one variation thereof, such as 2, 3, 4, 5, 6, 7, 8, 9 or 10 different variations of the wild type gene sequence). In some examples, the reaction includes (1) at least 2, at least 3, at least 4, at least 5, at least 10, at least 15, at least 20, at least 25, or at least 30 different NPPFs that each have specificity (e.g., complementarity) for a single target nucleic acid sequence, and (2) at least 2, at least 3, at least 4, at least 5, at least 10, at least 15, at least 20, at least 25, or at least 30 different NPPFs each having specificity (e.g., complementarity) for a single target gene, but with the ability to detect a plurality of variations in that gene.

Thus, a single sample may be contacted with one or more NPPFs. A set of NPPFs is a collection of two or more NPPFs each specific for (1) a different target sequence and/or a different portion of a same target gene, or specific for (2) a single target gene but with the ability to detect variations of the gene sequence. A set of NPPFs can include at least, up to, or exactly 2, 3, 4, 5, 6, 7, 8, 9, 10, 12, 15, 20, 25, 30, 50, 100, 500, 1000, 2000, 3000, 5000 or 10,000 different NPPFs. In some examples, a sample is contacted with a sufficient amount of NPPF to be in excess of the target(s) for such NPPF, such as a 100-fold, 500-fold, 1000-fold, 10,000-fold, 100,000-fold or 106-fold excess. In some examples, if a set of NPPFs is used, each NPPF of the set can be provided in excess to its respective target(s) (or portion of a target(s)) in the sample. Excess NPPF can facilitate quantitation of the amount of NPPF that binds a particular target(s). Some method embodiments involve a plurality of samples (e.g., at least, up to, or exactly 10, 25, 50, 75, 100, 500, 1000, 2000, 3000, 5000 or 10,000 different samples) simultaneously or contemporaneously contacted with the same NPPF or set of NPPFs.

Methods of empirically determining the appropriate size of a NPPF for use with a particular target(s) or samples (such as fixed or crosslinked samples) are routine. In specific embodiments, a NPPF can be up to 500 nucleotides in length, such as up to 400, up to 250, up to 100, or up to 75 nucleotides in length, including, for example, in the range of 20-500, 20-250, 25-200, 25-100, 25-75, or 25-50 nucleotides in length. In one non-limiting example, an NPPF is at least 35 nucleotides in length, such as at least 40, at least 45, at least 50, at least 75, at least 100, at least 150, or at least 200 nucleotides in length, such as 50 to 200, 50 to 150, 50 to 100, 75 to 200, 40 to 80, 35 to 150, or 36, 72, 75, or 100 nucleotides in length. Particular NPPF embodiments may be longer or shorter depending on desired functionality. In some examples, the NPPF is appropriately sized (e.g., sufficiently small) to penetrate fixed and/or crosslinked samples. Fixed or crosslinked samples may vary in the degree of fixation or crosslinking; thus, an ordinarily skilled artisan may determine an appropriate NPPF size for a particular sample condition or type, for example, by running a series of experiments using samples with known, fixed target concentration(s) and comparing NPPF size to target signal intensity. In some examples, the sample (and, therefore, at least a proportion of target) is fixed or crosslinked, and the NPPF is sufficiently small that signal intensity remains high and does not substantially vary as a function NPPF size.

Factors that affect NPPF-target and NPPF-CFS hybridization specificity include length of the NPPF and CFS, melting temperature, self-complementarity, and the presence of repetitive or non-unique sequence. See, e.g., Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999. Conditions resulting in particular degrees of hybridization (stringency) will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. In some examples, the NPPFs utilized in the disclosed methods have a $T_m$ of at least about 37° C., at least about 42° C., at least about 45° C., at least about 50° C., at least about 55° C., at least about 60° C., at least about 65° C., at least about 70° C., at least about 75° C., at least about 80° C., such as about 42° C.-80° C. (for example, about 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80° C.). In one non-limiting example, the NPPFs utilized in the disclosed methods have a $T_m$ of about 42° C. Methods of calculating the $T_m$ of a probe are known to one of skill in the art (see e.g., Sambrook et al., *Molecular Cloning: A Laboratory Manual*, 3d ed., Cold Spring Harbor Press, 2001, Chapter 10). In some examples, the NPPFs for a particular reaction are selected to each have the same or a similar $T_m$ in order to facilitate simultaneous detection or sequencing of multiple target nucleic acid molecules in a sample, such as $T_m$s+/−about 10° C. of one another, such as +/−10° C., 9° C., 8° C., 7° C., 6° C., 5° C., 4° C., 3° C., 2° C., or 1° C. of one another.

A. Region that Hybridizes to the Target

The portion of the NPPF sequence 102 (or 122) that specifically hybridizes to the target nucleic acid sequence is complementary in sequence to the target nucleic acid sequence(s) to be sequenced. This complementarity can be designed such that the NPP only hybridizes to a single target nucleic acid sequence, or can hybridize to a plurality of target nucleic acid sequences, such as wild type gene and variations thereof. For example, as shown in FIG. 10, a single NPPF (SEQ ID NO: 1) was designed to hybridize to not only the wild type BRAF sequence, but also to the mutant sequences that encode the V600E/K/R/E2/D mutations; a single NPPF (SEQ ID NO: 8) was designed to hybridize to not only the wild type KRAS sequence, but also to the mutant sequences that encode the G12/D/V/A/C/S/R and G12D mutations; and a single NPPF (SEQ ID NO: 17) was designed to hybridize to not only the wild type KRAS sequence, but also to the mutant sequences that encode the Q61E/R/L/H/C/T mutations. FIG. 10 shows the sequence of the NPPF, and the target sequences (thus, the NPPF shown in SEQ ID NO: 1 specific for BRAF and mutations (red nucleotides) that result in mutations at amino acid V600 hybridizes to the complement sequence of SEQ ID NOS: 2-7, the NPPF shown in SEQ ID NO: 8 specific for KRAS and mutations (red nucleotides) that result in mutations at amino acids G12 and G13 hybridizes to the complement sequence of SEQ ID NOS: 9-16, and the NPPF shown in SEQ ID NO: 17 specific for KRAS and mutations (red nucleotides) that result in mutations at amino acid Q61 hybridizes to the complement sequence of SEQ ID NOS: 18-23).

One skilled in the art will appreciate that the sequence 102 (or 122) need not be complementary to an entire target nucleic acid (e.g., if the target is a gene of 100,000 nucleotides, the sequence 102 (or 122) can be a portion of that, such as at least 10, at least 15, at least 20, at least 25, at least 30, at least 40, at least 50, at least 100, or more consecutive nucleotides complementary to a particular target nucleic acid molecule(s)). The specificity of a probe increases with length. Thus for example, a sequence 102 (or 122) that specifically binds to the target nucleic acid sequence(s) which includes 25 consecutive nucleotides will anneal to a target sequence with a higher specificity than a corresponding sequence of only 15 nucleotides. Thus, the NPPFs disclosed herein can have a sequence 102 (or 122) that specifically binds to the target nucleic acid sequence(s) which includes at least 6, at least 10, at least 15, at least 20, at least 25, at least 30, at least 40, at least 50, at least 60, at least 100, or more consecutive nucleotides complementary to a particular target nucleic acid molecule (such as about 6 to 50, 6 to 60, 10 to 40, 10 to 60, 15 to 30, 18 to 23, 19 to 22, or 20 to 25 consecutive nucleotides complementary to a target DNA or a target RNA).

Particular lengths of sequence 102 (or 122) that specifically binds to the target nucleic acid sequence(s) that can be part of the NPPFs used to practice the methods of the present disclosure include 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides complementary to a target nucleic acid molecule. In some examples where the target nucleic acid molecule is an miRNA (or siRNA), the length of the sequence 102 (or 122) that specifically binds to the target nucleic acid sequence can be shorter, such as 20-30 nucleotides in length (such as 20, 21, 22, 23, 24, 25, 26, 27, 28, 29, or 30 nucleotides) to match the miRNA (or siRNA) length. However, one skilled in the art will appreciate that the sequence 102 (or 122) that specifically binds to the target need not be 100% complementary to the target nucleic acid molecule. In some examples, the region of the NPPF complementary to the target and the target nucleic acid share at least 80%, at least 90%, at least 95%, at least 96%, at least 97%, at least 98%, at least 99%, or 100% complementarity, but wherein any mismatch can survive digestion with a nuclease. In some examples, for example if detection of a point mutation is desired, two NPPFs can be used, wherein the sequence 102 (or 122) of one NPPF is specific for the wild type sequence, and the sequence 102 (or 122) of the second NPPF is specific for the mutant sequence (which can allow quantitative measurements). Depending on the reaction conditions and the corresponding selectivity of the nuclease used, more than one mismatch may be present (such as at least two adjacent mismatches), for example to assist in nuclease digestion. In some examples, the NPPF is degenerate at one or more positions (such as 1, 2, 3, 4, 5, or more positions), for example, a mixture of nucleotides (such as 2, 3, or 4 nucleotides) at a specified position in the sequence 102 (or 122) that specifically binds to the target. In other examples, if detection of a point mutation is desired, a single NPPFs can be used, wherein the sequence 102 (or 122) of the NPPF is such that it allows hybridization to both the wild type sequence and the mutant sequence (e.g., see FIG. 10). In some examples, the NPPF includes one or more random bases, for example to identify regions containing mutations.

In some examples, the sequence 102 (or 122) of the NPPF includes at least one dUTP (such as at least 2, at least 3, at least 4, or at least 5 dUTPs, such as 1, 2, 3, 4, 5, 6, 7, 8, 9, 10 or 11 dUTPs). In some examples, all of the dTTPs are replaced with dUTPs. The presence of such bases allows the single stranded NPPF to be degraded or destroyed with uracil DNA deglycosylase (UDG) in later step (e.g., after denaturation of the NPPF from the ligated target, but before sequencing).

In one example, the sequence 102 (or 122) of the NPPF that is complementary to all or a portion of the target nucleic acid molecule includes at least one nucleotide mismatch. That is, at least one nucleotide is not complementary to its corresponding nucleotide in the target nucleic acid molecule, and thus will not form a base pair at this position. For example, as shown in FIG. 10, SEQ ID NO: 1 contains a "G" at positon 12 instead of an "A", SEQ ID NO: 8 contains a "G" at positon 15 instead of an "A", and SEQ ID NO: 17 contains a "T" at positon 13 instead of an "C". In some examples, the mismatch is not present in a flanking sequence. In some examples, the mismatch is not present within two bases of the flanking sequences (such that it is not within two bases of the 5'-end or the 3'-end of the region complementary to all or a portion of the target nucleic acid molecule of the NPPF). In some examples, the mismatch is at least two bases away from the 3'- or 5'-end of the NPPF. In some examples, the presence of the mismatch allows one to distinguish an NPPF from the target nucleic acid molecule.

B. Flanking Sequence(s)

The sequence of the flanking sequence 104, 106 (or 124, 126) provides a complementary sequence to which CFSs can specifically hybridize. Thus, each flanking sequence 104, 106 (or 124, 126) is complementary to at least a portion of a CFS (e.g., a 5'-flanking sequence is complementary to a 5CFS and a 3'-flanking sequence is complementary to a 3CFS). The flanking sequence is not similar to a sequence otherwise found in the sample (e.g., not found in the human genome). Thus, the flanking sequence includes a sequence of contiguous nucleotides not found in a nucleic acid molecule otherwise present in the sample. For example, if the target nucleic acid is a human sequence, the sequence of the flanking sequence is not similar to a sequence found in the target (e.g., human) genome. This helps to reduce non-specific binding (or cross-reactivity) of non-target sequences that may be present in the target genome to the NPPFs. Methods of analyzing a sequence for its similarity to a genome are known.

An NPPF can include one or two flanking sequences (e.g., one at the 5'-end, one at the 3'-end, or both), and the flanking sequences can be the same or different. In specific examples, each flanking sequence does not specifically bind to any other NPPF sequence (e.g., sequence 102, 122 or other flanking sequence) or to any component of the sample. In some examples, if there are two flanking sequences, the sequence of each flanking sequence 104, 106 (or 124, 126) is different. If there are two different flanking sequences (for example two different flanking sequences on the same NPPF and/or to flanking sequences of other NPPFs in a set of NPPFs), each flanking sequence 104, 106 (or 124, 126) in some examples has a similar melting temperature ($T_m$), such as a $T_m$ +/−about 10° C. or +/−5° C. of one another, such as +/−4° C., 3° C., 2° C., or 1° C.

In some examples, at least one flanking sequence includes at least one dUTP (such as at least 2, at least 3, at least 4, or at least 5 dUTPs in a flanking sequence, such as 1, 2, 3, 4, 5, 6, 7, 8, 9, 10 or 11 dUTPs per flanking sequence). The presence of such bases allows the single stranded NPPF to be degraded or destroyed with uracil DNA deglycosylase (UDG) in later step (e.g., after denaturation of the NPPF from the ligated target, but before sequencing). In some examples, the NPPF includes two flanking sequences, each having at least one dUTP. In some examples, the NPPF includes two flanking sequences, but only one flanking sequence has at least one dUTP. In some examples, the NPPF includes a single flanking sequence having at least one dUTP. In some examples, the location of the dUTP is close to the sequence complementary to a region of the target nucleic acid molecule, such as 1, 2, 3, 4, 5, bases away from (e.g., within 1, 2, 3, 4, 5, bases of) the sequence complementary to a region of the target nucleic acid molecule. In some examples, the location of the dUTP is at least two bases (such at least 3, at least 4, or at least 5 bases) away from the sequence complementary to a region of the target nucleic acid molecule. For example, at least one dUTP in the 5'-end flanking sequence 104 (or 124) can be 1, 2, 3, 4, or 5 bases from the 3'-end of the 5'-end flanking sequence 104 (or 124). For example, at least one dUTP in the 3'-end flanking sequence 106 (or 126) can be 1, 2, 3, 4, or 5 bases from the 5'-end of the 3'-end flanking sequence 106 (or 126).

In one example, the flanking sequence 104, 106 (or 124, 126) portion of the NPPF includes at least one nucleotide mismatch. That is, at least one nucleotide is not complementary to its corresponding nucleotide in the CFS, and thus will not form a base pair at this position.

In particular examples, the flanking sequence 104, 106 (or 124, 126) portion of the NPPF is at least 12 nucleotides in length, or at least 25 nucleotides in length, such as at least 15, at least 20, at least 25, at least 30, at least 40, or at least 50 nucleotides in length, such as 12 to 50, 12 to 25, or 12 to 30 nucleotides, for example, 20, 21, 22, 23, 24, 25, 26, 27, 28, 29 or 30 nucleotides in length, wherein the contiguous nucleotides not found in a nucleic acid molecule present in the sample to be tested. The flanking sequences are protected from degradation by the nuclease by hybridizing molecules to the flanking sequences which have a sequence complementary to the flanking sequences (CFSs).

IV. Complementary Flanking Sequences (CFSs)

Each CFS (e.g., 208 or 210 of FIG. 2A) is complimentary to its corresponding flanking sequence of the NPPF. For example, if an NPPF includes a 5'-flanking sequence, a 5CFS will be used in the method. If an NPPF includes a 3'-flanking sequence, a 3CFS will be used in the method. If the 5'- and the 3'-flanking sequences are different from one another, the 5CFS and 3CFS will be different from one another. One skilled in the art will appreciate that the CFS and the flanking sequence of the NPPF need not be 100% complementary, as long as hybridization can occur between the NPPF and its target and corresponding CFS(s). In some examples, the flanking sequence of the NPPF and the CFS share at least 80%, at least 90%, at least 95%, at least 98%, at least 99%, or 100% complementarity. In some examples the CFS is the same length as its corresponding flanking sequence of the NPPF. For example, if the flanking sequences 25 nt, the CFS can be 25 nt.

In some examples, the CFS is not similar to a sequence found in the target genome. For example, if the target nucleic acid is a human sequence, the sequence of the CFS (and corresponding flanking sequence) is not similar to a sequence found in the target genome. This helps to reduce binding of non-target sequences that may be present in the target genome from binding to the CFSs (and NPPFs). Methods of analyzing a sequence for its similarity to a genome are well known in the art.

CFS can provide a universal amplification point that is complementary to at least a portion of an amplification primer. The CFS thus permits use of the same amplification primers to amplify ligated targets for different target nucleic acid molecules. Thus, at least a portion of sequence of the CFS is complimentary to at least a portion of an amplification primer. As shown in FIG. 5, this allows the primer to hybridize to the CFS, and amplify the target nucleic acid molecule to which the CFS is ligated. As CFS can be identical between different target nucleic acid molecules, this permits the same primer to be used to amplify any number of different targets to which the CFS is ligated. Thus an amplification primer that includes a sequence complementary to the 5CFS, and an amplification primer that includes a sequence complementary to the 3CFS, can both be used in a single reaction to amplify multiple ligated targets, even if the target sequences differ.

In some examples, the CFS does not include an experiment tag sequence and/or a sequencing adaptor sequence. In some examples, a CFS includes or consists of an experiment tag sequence and/or sequencing adaptor sequence. In other examples, the primers used to amplify the ligated targets (which include at least one CFS) include an experiment tag sequence and/or sequencing adaptor sequence (such as a poly-A or poly-T sequence needed for some sequencing platforms), thus permitting incorporation of the experiment tag and/or sequencing adaptor into the ligated target amplicon during amplification of the ligated target. Experimental tags and sequencing adaptors are described above in Section II, G. One will appreciate that more than one experiment tag can be included (such as at least 2, at least 3, at least 4, or at least 5 different experiment tags), such as those used to uniquely identify a ligated target, ligated target amplicon, or a sample.

As illustrated in FIGS. 6A and B, the method can use a single CFS. FIGS. 6A and 6B show the CFS at the 5'-end (5CFS), but one will appreciate it could be at the 3'-end instead. FIG. 6A shows an example where all of the targets in the reaction are ligated to the same CFS F1 (and thus the NPPFs in the reaction have the same flanking sequence). Amplification with an F1-specific primer could be used to add the same 5'- or 3'-tag (e.g., sequencing adaptor or experimental tag) to each ligated target. For example, the same sequencing adaptor could be added to all of the ligated targets, permitting sequencing of the targets in the same sequencing platform. FIG. 6B shows an example where each target in the reaction is ligated to a different CFS F1, F2, and F3 (and thus the NPPFs or each subpopulation of NPPFs in the reaction have a different flanking sequence). In another example, amplification with T1-F1-, T2-F2-, and T3-F3-specific primers can be used to add a different experimental tag to each different ligated target.

As illustrated in FIGS. 6C-6F, the target can in some examples can be ligated to two CFSs (and thus the NPPFs used have two flanking sequences), one at the 5'-end, the other at the 3'-end of the target. FIG. 6C shows an example where all of the targets in the reaction are ligated to the same CFS, F1, at both ends. FIG. 6D shows an example wherein all of the CFS on the 5'-end are the same (e.g., F1), and all of the CFS on the 3'-end are the same (e.g., F(a)), but the 5'-end and 3'-end CFSs differ. In such an example, this permits the inclusion of the same experiment tag on one end of the target, and the inclusion of the same sequencing adaptor to the other side of the target. FIG. 6E shows an example wherein all of the CFSs on one end are the same (e.g., F1 on the 5'-end), but all of the CFSs on the other end differ from one another (e.g., F(a), F(b), and F(c)). In such an example, this permits the use of a sequencing adaptor for all of the ligated targets. The flanking sequences on the other end, F(a), F(b) & F(c), could be used for example to differentially label each target (such as using different experiment tags). FIG. 6F shows an example wherein all of the CFSs are different, irrespective of their position (e.g., F(a), F(b), F(c), F1, F2, and F3). In this example, each CFS can be used for a different experiment tag or for combinations of different experiment tags and different sequencing adaptors.

V. Samples

A sample is any collective comprising one or more targets, such as a biological sample or biological specimen, such as those obtained from a subject (such as a human or other mammalian subject, such as a veterinary subjects, for example a subject known or suspected of having a tumor or an infection). The sample can be collected or obtained using methods well known to those ordinarily skilled in the art The samples of use in the disclosed methods can include any specimen that includes nucleic acid (such as genomic DNA, cDNA, viral DNA or RNA, rRNA, tRNA, mRNA, miRNA, oligonucleotides, nucleic acid fragments, modified nucleic acids, synthetic nucleic acids, or the like). In one example, the sample includes RNA. In some examples, the target nucleic acid molecule to be sequenced is cross-linked in the sample (such as a cross-linked DNA, mRNA, miRNA, or vRNA) or is soluble in the sample. In some examples, the sample is a fixed sample, such as a sample that includes an agent that causes target molecule cross-linking (and thus in some examples the target nucleic acid molecule can be fixed). In some examples, the target nucleic acid in the sample is not extracted, solubilized, or both, prior to detecting or sequencing the target nucleic acid molecule. In some examples, the sample is an ex situ biological sample.

In some examples, the disclosed methods include obtaining the sample prior to analysis of the sample. In some examples, the disclosed methods include selecting a subject having a particular disease or tumor, and then in some examples further selecting one or more target DNAs or RNAs to detect based on the subject's particular disease or tumor, for example, to determine a diagnosis or prognosis for the subject or for selection of one or more therapies. In some examples, nucleic acid molecules in a sample to be analyzed are first isolated, extracted, concentrated, or combinations thereof, from the sample.

In some examples, RNA in the sample reverse transcribed prior to performing the methods provided herein.

In some examples, the sample, such as an ex situ sample, is lysed. The lysis buffer in certain examples may inactivate enzymes that degrade RNA, but after a limited dilution into a hybridization dilution buffer it permits nuclease activity and facilitates hybridization with stringent specificity. A dilution buffer can be added to neutralize the inhibitory activity of the lysis and other buffers, such as inhibitory activity for other enzymes (e.g., polymerase). Alternatively, the composition of the lysis buffer and other buffers can be changed to a composition that is tolerated, for example by a polymerase or ligase.

In some examples, the methods include analyzing a plurality of samples simultaneously or contemporaneously. For example, the methods can analyze at least two different samples (for example from different subjects, e.g., patients) simultaneously or contemporaneously. In one such example, the methods further can detect or sequence at least two different target nucleic acid molecules (such as 2, 3, 4, 5, 6, 7, 8, 9 or 10 different targets) in at least two different samples (such as at least 5, at least 10, at least 100, at least 500, at least 1000, or at least 10,000 different samples) simultaneously or contemporaneously.

Exemplary samples include, without limitation, cells, cell lysates, blood smears, cytocentrifuge preparations, flow-sorted or otherwise selected cell populations, cytology smears, chromosomal preparations, bodily fluids (e.g., blood and fractions thereof such as white blood cells, serum or plasma; saliva; sputum; urine; spinal fluid; gastric fluid; sweat; semen; etc.), buccal cells, extracts of tissues, cells or organs, tissue biopsies (e.g., tumor or lymph node biopsies), liquid biopsies, fine-needle aspirates, brocoscopic lavage, punch biopsies, circulating tumor cells, bone marrow, amniocentesis samples, autopsy material, fresh tissue, frozen tissue, fixed tissue, fixed and wax- (e.g., paraffin-) embedded tissue, bone marrow, and/or tissue sections (e.g., cryostat tissue sections and/or paraffin-embedded tissue sections). The biological sample may also be a laboratory research sample such as a cell culture sample or supernatant.

Exemplary samples may be obtained from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis. In particular examples, a biological sample includes a tumor sample, such as a sample containing neoplastic cells.

Exemplary neoplastic cells or tissues may be included in or isolated from solid tumors, including lung cancer (e.g., non-small cell lung cancer, such as lung squamous cell carcinoma), breast carcinomas (e.g. lobular and duct carcinomas), adrenocortical cancer, ameloblastoma, ampullary cancer, bladder cancer, bone cancer, cervical cancer, cholangioma, colorectal cancer, endometrial cancer, esophageal cancer, gastric cancer, glioma, granular call tumor, head and neck cancer, hepatocellular cancer, hydatiform mole, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz nevus, squamous cell cancer, teratoid cancer, and thyroid cancer. Exemplary neoplastic cells may also be included in or isolated from hematological cancers including leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

For example, a sample from a tumor that contains cellular material can be obtained by surgical excision of all or part of the tumor, by collecting a fine needle aspirate from the tumor, as well as other methods. In some examples, a tissue or cell sample is applied to a substrate and analyzed to determine presence of one or more target DNAs or RNAs. A solid support useful in a disclosed method need only bear the biological sample and, optionally, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

The disclosed methods are sensitive and specific and allow sequencing of target nucleic acid molecules in a sample containing even a limited number of cells. Samples that include small numbers of cells, such as less than 250,000 cells (for example less than 100,000, less than 50,000, less than 10,000, less than 1,000, less than 500, less than 200, less than 100 cells, or less than 10 cells, include but are not limited to, FFPE samples, fine needle aspirates (such as those from lung, prostate, lymph, breast, or liver), punch biopsies, needle biopsies, small populations of (e.g., FACS) sorted cells or circulating tumor cells, lung aspirates, small numbers of laser captured, flow-sorted, or macrodissected cells or circulating tumor cells, exosomes and other subcellular particles, or body fluids (such as plasma, serum, spinal fluid, saliva, and breast aspirates). For example, a target DNA or target RNA can be sequenced (and thus detected) in as few as 1000 cells (such as a sample including 1000 or more cells, such as 1000, 2000, 3000, 4000, 5000, 6000, 7000, 8000, 9000, 10,000, 15,000, 20,000, 50,000, or more cells). In some examples, expression of a target DNA or target RNA can be detected in about 1000 to 100,000 cells, for example about 1000 to 50,000, 1000 to 15,000, 1000 to 10,000, 1000 to 5000, 3000 to 50,000, 6000 to 30,000, or 10,000 to 50,000 cells). In some examples, expression of a target DNA or target RNA can be detected in about 100 to 250,000 cells, for example about 100 to 100,000, 100 to 50,000, 100 to 10,000, 100 to 5000, 100 to 500, 100 to 200, or 100 to 150 cells. In other examples, a target DNA or target RNA can be sequenced in about 1 to 1000 cells (such as about 1 to 500 cells, about 1 to 250 cells, about 1 to 100 cells, about 1 to 50 cells, about 1 to 25 cells, or about 1 cell).

Samples may be treated in a number of ways prior to (or contemporaneous with) contacting the sample with a target-specific reagent (such as NPPFs and corresponding CFSs). One relatively simple treatment is suspension of the sample in a buffer, e.g., lysis buffer, which conserves all components of the sample in a single solution. In some examples, the sample is treated to partially or completely isolate (e.g., extract) a target (e.g., DNA or mRNA) from the sample. A target (such as, DNA or RNA) has been isolated or extracted when it is purified away from other non-target biological components in a sample. Purification refers to separating the target from one or more extraneous components (e.g., organelles, proteins) also found in a sample. Components that are isolated, extracted or purified from a mixed specimen or sample typically are enriched by at least 50%, at least 60%, at least 75%, at least 90%, or at least 98% or even at least 99% compared to the unpurified or non-extracted sample.

Isolation of biological components from a sample is time consuming and bears the risk of loss of the component that is being isolated, e.g., by degradation and/or poor efficiency or incompleteness of the process(es) used for isolation. Moreover, with some samples, such as fixed tissues, targets (such as DNA or RNA (e.g., mRNA or miRNA)) are notoriously difficult to isolate with high fidelity (e.g., as compared to fresh or frozen tissues) because, it is thought that, at least some proportion of the targets are cross-linked to other components in the fixed sample and, therefore, cannot be readily isolated or solubilized and may be lost upon separation of soluble and insoluble fractions. Additionally, very short DNA and RNA fragments may be lost during precipitation or matrix-binding steps, leading to measurement biases. Accordingly, in some examples, the disclosed methods of sequencing a target nucleic acid do not require or involve purification, extraction or isolation of a target nucleic acid molecule from a sample prior to contacting the sample with one or more NPPFs and corresponding CFSs, and/or involve only suspending the sample in a solution, e.g., lysis buffer, that retains all components of the sample prior to contacting the sample with NPPFs and corresponding CFSs. Thus, in some examples, the methods do not include isolating nucleic acid molecules from a sample prior to their analysis.

In some examples, cells in the sample are lysed or permeabilized in an aqueous solution (for example using a lysis buffer). The aqueous solution or lysis buffer includes detergent (such as sodium dodecyl sulfate) and one or more chaotropic agents (such as formamide, guanidinium HCl, guanidinium isothiocyanate, or urea). The solution may also contain a buffer (for example SSC). In some examples, the lysis buffer includes about 8% to 60% formamide (v/v) about 0.01% to 0.1% SDS, and about 0.5-6×SSC (for example, about 3×SSC). The buffer may optionally include tRNA (for example, about 0.001 to about 2 mg/ml); a ribonuclease; DNase; proteinase K; enzymes (e.g. collagenase or lipase) that degrade protein, matrix, carbohydrate, lipids, or one species of oligonucleotides, or combinations thereof. The lysis buffer may also include a pH indicator, such as phenol red. Cells are incubated in the aqueous solution (optionally overlayed with oil) for a sufficient period of time (such as about 1 minute to about 60 minutes, for example about 5 minutes to about 20 minutes, or about 10 minutes) and at a sufficient temperature (such as about 22° C. to about 110° C., for example, about 80° C. to about 105° C., about 37° C. to about 105° C., or about 90° C. to about 100° C.) to lyse or permeabilize the cell. In some examples, lysis is performed at about 50° C., 65° C., 95° C., or 105° C. In some examples, the lysis step includes incubating the sample at about 95° C. for about 5-15 minutes to denature RNA in the sample, but not genomic DNA. In other examples, the lysis step includes incubating the sample at about 105° C. for about 5-15 minutes to denature both RNA and genomic DNA in the sample. In one example Proteinase K is included with the lysis buffer.

In some examples, the crude cell lysis is used directly without further purification. The cells may be lysed in the presence or absence of one or more of the NPPFs and corresponding CFSs. If the cells are lysed in the absence of NPPFs and corresponding CFSs, the one or more NPPFs and corresponding CFSs can be subsequently added to the crude lysate. In other examples, nucleic acids (such as DNA and/or RNA) are isolated from the cell lysate prior to contacting the lysate with one or more NPPFs and corresponding CFSs.

In other examples, tissue samples are prepared by fixing and embedding the tissue in a medium or include a cell suspension is prepared as a monolayer on a solid support (such as a glass slide), for example by smearing or centrifuging cells onto the solid support. In further examples, fresh frozen (for example, unfixed) tissue or tissue sections may be used in the methods disclosed herein. In particular examples, FFPE tissue sections are used in the disclosed methods.

In some examples an embedding medium is used. An embedding medium is an inert material in which tissues and/or cells are embedded to help preserve them for future analysis. Embedding also enables tissue samples to be sliced into thin sections. Embedding media include paraffin, celloidin, OCT™ compound, agar, plastics, or acrylics. Many embedding media are hydrophobic; therefore, the inert material may need to be removed prior to analysis, which utilizes primarily hydrophilic reagents. The term deparaffinization or dewaxing refers to the partial or complete removal of any type of embedding medium from a biological sample. For example, paraffin-embedded tissue sections are dewaxed by passage through organic solvents, such as toluene, xylene, limonene, or other suitable solvents. In other examples, paraffin-embedded tissue sections are utilized directly (e.g., without a dewaxing step).

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing tissue or cell samples is formaldehyde, generally in the form of a formalin solution (4% formaldehyde in a buffer solution, referred to as 10% buffered formalin). In one example, the fixative is 10% neutral buffered formalin, and thus in some examples the sample is formalin fixed.

In some examples, the sample is an environmental sample (such as a soil, air, air filter, or water sample, or a sample obtained from a surface (for example by swabbing)), or a food sample (such as a vegetable, fruit, dairy or meat containing sample) for example to detect pathogens that may be present.

VI. Target Nucleic Acids

A target nucleic acid molecule (such as a target DNA or RNA) is a nucleic acid molecule whose detection, amount, and/or sequence is intended to be determined (for example in a quantitative or qualitative manner), with the disclosed methods. In one example, the target is a defined region or particular portion of a nucleic acid molecule, for example a DNA or RNA of interest. In an example where the target nucleic acid sequence is a target DNA or a target RNA, such a target can be defined by its specific sequence or function; by its gene or protein name; or by any other means that uniquely identifies it from among other nucleic acids.

In some examples, alterations of a target nucleic acid sequence (e.g., a DNA or RNA) are "associated with" a disease or condition. That is, sequencing of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by nucleotide polymorphisms or mutation, and/or the two different forms can be quantitatively distinguishable, such as by the number of copies of the target nucleic acid sequence that are present in a sample.

Targets include single-, double- or other multiple-stranded nucleic acid molecules (such as, DNA (e.g., genomic, mitochondrial, or synthetic), RNA (such as mRNA, miRNA, tRNA, siRNA, long non-coding (nc) RNA, biologically occurring anti-sense RNA, Piwi-interacting RNAs (piRNAs), or small nucleolar RNAs (snoRNAs)), whether from eukaryotes, prokaryotes, viruses, fungi, bacteria, parasites, or other biological organism. Genomic DNA targets may include one or several parts of the genome, such as coding regions (e.g., genes or exons), non-coding regions (whether having known or unknown biological function, e.g., enhancers, promoters, regulatory regions, telomeres, or "nonsense" DNA). In some embodiments, a target may contain or be the result of a mutation (e.g., germ line or somatic mutation) that may be naturally occurring or otherwise induced (e.g., chemically or radiation-induced mutation). Such mutations may include (or result from) genomic rearrangements (such as translocations, insertions, deletions, or inversions), single nucleotide variations, and/or genomic amplifications. In some embodiments, a target may contain one or more modified or synthetic monomers units (e.g., peptide nucleic acid (PNA), locked nucleic acid (LNA), methylated nucleic acid, post-translationally modified amino acid, cross-linked nucleic acid or cross-linked amino acid).

The portion of a target nucleic acid molecule to which a NPPF may specifically bind also may be referred to as "target," again, as context dictates, but more specifically may be referred to as target portion, complementary region (CR), target site, protected target region or protected site, or similar. A NPPF specifically bound to its complementary region forms a complex, which complex may remain integrated with the target as a whole and/or sample, or be separate (or be or become separated) from the target as a whole and/or the sample. In some embodiments, a NPPF/CR complex is separated (or becomes disassociated) from the target as a whole and/or the sample, e.g., by the action of a nuclease, such as S1 nuclease.

All types of target nucleic acid molecules can be analyzed using the disclosed methods. In one example, the target is a ribonucleic acid (RNA) molecule, such as a messenger RNA (mRNA), a ribosomal RNA (rRNA), a transfer RNA (tRNA), micro RNA (miRNA), an siRNA, anti-sense RNA, or a viral RNA (vRNA). In another example, the target is a deoxyribonucleic (DNA) molecule, such as genomic DNA (gDNA), mitochondrial DNA (mtDNA), chloroplast DNA (cpDNA), viral DNA (vDNA), cDNA, or a transfected DNA. In a specific example, the target is an antisense nucleotide. In some examples, the whole transcriptome of a cell or a tissue can be sequenced using the disclosed methods. In one example, the target nucleic acid molecule to be sequenced is a rare nucleic acid molecule, for example only appearing less than about 100,000 times, less than about 10,000 times, less than about 5,000 times, less than about 100 times, less than 10 times, or only once in the sample, such as a nucleic acid molecule only appearing 1 to 10,000, 1 to 5,000, 1 to 100 or 1 to 10 times in the sample).

A plurality of targets can be sequenced in the same sample or assay, or even in multiple samples or assays, for example simultaneously or contemporaneously. Similarly, a single target can be sequenced in a plurality of samples, for example simultaneously or contemporaneously. In one example the target nucleic acid molecules are an miRNA and an mRNA. Thus, in such an example, the method would include the use of at least one NPPF specific for the miRNA and at least one NPPF specific for the mRNA. In one example the target nucleic acid molecules are two different DNA molecules. Thus, in such an example, the method would include the use of at least one NPPF specific for the first target DNA and at least one NPPF specific for the second target DNA. In one example the target nucleic acid molecules are two different RNA molecules. Thus, in such an example, the method would include the use of at least one NPPF specific for the first target RNA and at least one NPPF specific for the second target RNA.

In some examples, the disclosed methods permit sequencing of DNA or RNA single nucleotide polymorphisms (SNPs) or variants (sNPVs), splice junctions, methylated DNA, gene fusions or other mutations, protein-bound DNA or RNA, and also cDNA, as well as levels of expression (such as DNA or RNA expression, such as cDNA expression, mRNA expression, miRNA expression, rRNA expression, siRNA expression, or tRNA expression). Any nucleic acid molecule to which a nuclease protection probe can be designed to hybridize can be quantified and identified by the disclosed methods.

In one example, DNA methylation is detected by using an NPPF that includes a base mismatch at the site where methylation has or has not occurred, such that upon treatment of the target sample, methylated bases are converted to a different base, complementary to the base in the NPPF. Thus, in some examples, the methods include treating the sample with bisulfite.

One skilled in the art will appreciate that the target can include natural or unnatural bases, or combinations thereof.

In specific non-limiting examples, a target nucleic acid (such as a target DNA or target RNA) associated with a neoplasm (for example, a cancer) is selected. Numerous chromosome abnormalities (including translocations and other rearrangements, reduplication or deletion) or mutations have been identified in neoplastic cells, especially in cancer cells, such as B cell and T cell leukemias, lymphomas, breast cancer, colon cancer, neurological cancers and the like.

In some examples, a target nucleic acid molecule includes wild type and/or mutated: delta-aminolevulinate synthase 1 (ALAS1) (e.g., GENBANK® Accession No. NM_000688.5 or OMIM 125290), 60S ribosomal protein L38 (RPL38) (e.g., GENBANK® Accession No. NM_000999.3 or OMIM 604182), proto-oncogene B-Raf (BRAF) (e.g., GENBANK® Accession No. NM_004333.4 or OMIM 164757) (such as the wild type BRAF or the V600E, V600K, V600R, V600E2, and/or V600D mutation, e.g., see FIG. 10), forkhead box protein L2 (FOXL2) (e.g., GENBANK® Accession No. NM_023067.3 or OMIM 605597) (such as the wild type FOXL2 or the nt820 snp C→G); epidermal growth factor receptor (EGFR) (e.g., GENBANK® Accession No. NM_005228.3 or OMIM 131550) (such as the wild type EGFR, and/or one or more of a T790M, L858R, D761Y, G719A, G719S, and a G719C mutation, or other mutation shown in FIG. 9); GNAS (e.g., GENBANK® Accession No. NM_000516.5 or OMIM 139320); or KRAS (e.g., GENBANK® Accession No. NM_004985.4 or OMIM 190070) (such as the wild type KRAS, a D761Y mutation, a G12 mutation such as one or more of G12D, G12V, G12A, G12C, G12S, G12R, a G13 mutation such as G13D and/or a Q61 mutation such as one or more of Q61E, Q61R, Q61L, Q61H-C, and/or Q61H-T, e.g., see FIG. 10); (also see FIGS. 7A, 7B, 8).

In some examples, a target nucleic acid molecule includes GAPDH (e.g., GENBANK® Accession No. NM_002046), PPIA (e.g., GENBANK® Accession No. NM_021130), RPLPO (e.g., GENBANK® Accession Nos. NM_001002 or NM_053275), RPL19 (e.g., GENBANK® Accession No. NM_000981), ZEB1 (e.g., GENBANK® Accession No. NM_030751), Zeb2 (e.g., GENBANK® Accession Nos. NM_001171653 or NM_014795), CDH1 (e.g., GEN- BANK® Accession No. NM_004360), CDH2 (e.g., GENBANK® Accession No. NM_007664), VIM (e.g., GENBANK® Accession No. NM_003380), ACTA2 (e.g., GENBANK® Accession No. NM_001141945 or NM_001613), CTNNB1 (e.g., GENBANK® Accession No. NM_001904, NM_001098209, or NM_001098210), KRT8 (e.g., GENBANK® Accession No. NM_002273), SNAI1 (e.g., GENBANK® Accession No. NM_005985), SNAI2 (e.g., GENBANK® Accession No. NM_003068), TWIST1 (e.g., GENBANK® Accession No. NM_000474), CD44 (e.g., GENBANK® Accession No. NM_000610, NM_001001389, NM_00100390, NM_001202555, NM_001001391, NM_001202556, NM_001001392, NM_001202557), CD24 (e.g., GENBANK® Accession No. NM_013230), FN1 (e.g., GENBANK® Accession No. NM_212474, NM_212476, NM_212478, NM_002026, NM_212482, NM_054034), IL6 (e.g., GENBANK® Accession No. NM_000600), MYC (e.g., GENBANK® Accession No. NM_002467), VEGFA (e.g., GENBANK® Accession No. NM_001025366, NM_001171623, NM_003376, NM_001171624, NM_001204384, NM_001204385, NM_001025367, NM_001171625, NM_001025368, NM_001171626, NM_001033756, NM_001171627, NM_001025370, NM_001171628, NM_001171622, NM_001171630), HIF1A (e.g., GENBANK® Accession No. NM_001530, NM_181054), EPAS1 (e.g., GENBANK® Accession No. NM_001430), ESR2 (e.g., GENBANK® Accession No. NM_001040276, NM_001040275, NM_001214902, NM_001437, NM_001214903), PRKCE (e.g., GENBANK® Accession No. NM_005400), EZH2 (e.g., GENBANK® Accession No. NM_001203248, NM_152998, NM_001203247, NM_004456, NM_001203249), DAB2IP (e.g., GENBANK® Accession No. NM_032552, NM_138709), B2M (e.g., GENBANK® Accession No. NM_004048), and SDHA (e.g., GENBANK® Accession No. NM_004168).

In some examples, a target miRNA includes hsa-miR-205 (MIR205, e.g., GENBANK® Accession No. NR_029622), hsa-miR-324 (MIR324, e.g., GENBANK® Accession No.NR_029896), hsa-miR-301a (MIR301A, e.g., GENBANK® Accession No. NR_029842), hsa-miR-106b (MIR106B, e.g., GENBANK® Accession No. NR_029831), hsa-miR-877 (MIR877, e.g., GENBANK® Accession No. NR_030615), hsa-miR-339 (MIR339, e.g., GENBANK® Accession No. NR_029898), hsa-miR-10b (MIR10B, e.g., GENBANK® Accession No. NR_029609), hsa-miR-185 (MIR185, e.g., GENBANK® Accession No. NR_029706), hsa-miR-27b (MIR27B, e.g., GENBANK® Accession No. NR_029665), hsa-miR-492 (MIR492, e.g., GENBANK® Accession No. NR_030171), hsa-miR-146a (MIR146A, e.g., GENBANK® Accession No. NR_029701), hsa-miR-200a (MIR200A, e.g., GENBANK® Accession No. NR_029834), hsa-miR-30c (e.g., GENBANK® Accession No. NR_029833, NR_029598), hsa-miR-29c (MIR29C, e.g., GENBANK® Accession No. NR_029832), hsa-miR-191 (MIR191, e.g., GENBANK® Accession No. NR_029690), or hsa-miR-655 (MIR655, e.g., GENBANK® Accession No. NR_030391).

In one example the target is a pathogen nucleic acid, such as viral RNA or DNA. Exemplary pathogens include, but are not limited to, viruses, bacteria, fungi, parasites, and protozoa. In one example, the target is a viral RNA. Viruses include positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepataviridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); and Coronaviruses (examples of which include SARS coronaviruses, such as the Urbani strain). Exemplary negative-strand RNA viruses include, but are not limited to: Orthomyxyoviruses (such as the influenza virus), Rhabdoviruses (such as Rabies virus), and Paramyxoviruses (examples of which include measles virus, respiratory syncytial virus, and parainfluenza viruses). In one example the target is viral DNA from a DNA virus, such as Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19). In another example, the target is a retroviral nucleic acid, such as one from human immunodeficiency virus type 1 (HIV-1), such as subtype C, HIV-2; equine infectious anemia virus; feline immunodeficiency virus (FIV); feline leukemia viruses (FeLV); simian immunodeficiency virus (SIV); and avian sarcoma virus. In one example, the target nucleic acid is a bacterial nucleic acid. In one example the bacterial nucleic acid is from a gram-negative bacteria, such as *Escherichia coli* (K-12 and O157:H7), *Shigella dysenteriae*, and *Vibrio cholerae*. In another example the bacterial nucleic acid is from a gram-positive bacteria, such as *Bacillus anthracis*, *Staphylococcus aureus*, pneumococcus, gonococcus, and streptococcal meningitis. In one example, the target nucleic acid is a nucleic acid from protozoa, nemotodes, or fungi. Exemplary protozoa include, but are not limited to, *Plasmodium, Leishmania, Acanthamoeba, Giardia, Entamoeba, Cryptosporidium, Isospora, Balantidium, Trichomonas, Trypanosoma, Naegleria*, and *Toxoplasma*. Exemplary fungi include, but are not limited to, *Coccidiodes immitis* and *Blastomyces dermatitidis*.

One of skill in the art can identify additional target DNAs or RNAs and/or additional target miRNAs which can be detected utilizing the methods disclosed herein.

VII. Assay Output

In some embodiments, the disclosed methods include determining the sequence of one or more target nucleic acid molecules in a sample, which can include quantification of sequences detected. The results of the methods can be provided to a user (such as a scientist, clinician or other health care worker, laboratory personnel, or patient) in a perceivable output that provides information about the results of the test. In some examples, the output can be a paper output (for example, a written or printed output), a display on a screen, a graphical output (for example, a graph, chart, or other diagram), or an audible output. In one example, the output is a table or graph including a qualitative or quantitative indicator of presence or amount (such as a normalized amount) of a target nucleic acid sequenced (or sequence not detected) in the sample. In other examples, the embodiments, the output is the sequence of one or more target nucleic acid molecules in a sample, such a report indicting the presence of a particular mutation(s) in the target molecule.

The output can provide quantitative information (for example, an amount of a particular target nucleic acid molecule or an amount of a particular target nucleic acid molecule relative to a control sample or value) or can provide qualitative information (for example, a determination of presence or absence of a particular target nucleic acid molecule). In additional examples, the output can provide qualitative information regarding the relative amount of a target nucleic acid molecule in the sample, such as identifying an increase or decrease relative to a control or no change relative to a control.

As discussed herein, the ligated target or ligated target amplicons can include one or more experiment tags, which can be used for example to identify a particular patient, sample, experiment, or target sequence. The use of such tags permits the sequenced ligated target or ligated target amplicon to be "sorted" or even counted, and thus permits analysis of multiple different samples (for example from different patients), multiple different targets (for example at least two different nucleic acid targets), or combinations thereof, in a single reaction. In one example, ILLUMINA® software and Bowtie software can be used for such analysis.

In one example, the ligated target or ligated target amplicon includes an experiment tag unique for each different target nucleic acid molecule. The use of such a tag allows one to merely sequence or detect this tag, without sequencing the entire ligated target or ligated target amplicon, to identify the ligated target or ligated target amplicon. In addition, if multiple nucleic acid targets are to be analyzed, the use of a unique experiment tag for each target simplifies the analysis, as each detected or sequenced experiment tag can be sorted, and if desired counted. This permits for semi-quantification or quantification of the target nucleic acid that was in the sample as the ligated targets or ligated target amplicons are in roughly in stoichiometric proportion to the target in the sample. For example if multiple target nucleic acids are detected or sequenced in a sample, the methods permit the generation of a table or graph showing each target sequence and the number of copies detected or sequenced, by simply detecting or sequencing and then sorting the experimental tag.

In another example, the ligated target or ligated target amplicons include an experiment tag unique for each different sample (such as a unique tag for each patient sample). The use of such a tag allows one to associate a particular detected ligated target or ligated target amplicon with a particular sample. Thus, if multiple samples are analyzed in the same reaction (such as the same well or same sequencing reaction), the use of a unique experiment tag for each sample simplifies the analysis, as each detected or sequenced ligated target or ligated target amplicon can be associated with a particular sample. For example if a target nucleic acid is detected or sequenced in samples, the methods permit the generation of a table or graph showing the result of the analysis for each sample.

One skilled in the art will appreciate that each ligated target or ligated target amplicon can include a plurality of experiment tags (such as at least 2, 3, 4, 5, 6, 7, 8, 9 or 10 experiment tags), such as a tag representing the target sequence, and another representing the sample. Once each tag is detected or sequenced, appropriate software can be used to sort the data in any desired format, such as a graph or table. For example, this permits analysis of multiple target sequences in multiple samples simultaneously or contemporaneously.

In some examples, the sequenced ligated target or ligated target amplicon is compared to a database of known sequences for each target nucleic acid sequence. In some examples, such a comparison permits detection of mutations, such as SNPs.

VIII. Kits

Also disclosed herein are kits that can be used to directly sequence one or more target nucleic acid molecules.

The kits include one or more NPPFs that specifically hybridize to one or more nucleic acid targets. The kits also include corresponding CFS(s). For example, if the NPPF includes a 5'-flanking sequence, the kit can include a 5CFS that is complementary to the 5'-flanking sequence. If the NPPF includes a 3'-flanking sequence, the kit can include a 3CFS that is complementary to the 3'-flanking sequence. In some examples, the NPPFs and CFS(s) are in the same vial or container. In some examples, the kits include both a 5CFS and a 3CFS, wherein one of the CFSs includes a capture moiety. In some examples, the kit includes a plurality of NPPFs and corresponding CFS(s) specific for a single target nucleic acid molecule, such as at least 2, at least 3, at least 4, at least 5, at least 10, or at least 20 different NPPFs (such as 2, 3, 4, 5, 6, 7, 8, 9, 10, 12, 15 or 20 different NPPFs) that can specifically hybridize to a target nucleic acid molecule. In some examples, the kit includes a plurality of NPPFs and corresponding CFS(s) specific for a plurality of different target nucleic acid molecules, such as at least 2, at least 3, at least 4, at least 5, at least 10, at least 20, at least 50, at least 75, or at least 100 different target nucleic acid molecule (such as 2, 3, 4, 5, 6, 7, 8, 9, 10, 12, 15, 20, 40, 50, 75, 100, 200, or 500 different target nucleic acid molecule). In some embodiments, the disclosed kits include at least one NPPF and corresponding CFS(s) specific for more control nucleic acid molecules, such as a positive (e.g., housekeeper) or negative control (e.g., ANT).

In some examples, the kit includes nucleic acid probes or primers (for example in separate vials or containers) that permit amplification of a target nucleic acid molecule, such as a ligated target nucleic acid molecule. In some examples, at least a portion of such probes or primers is complementary to a CFS in the kit, thus allowing hybridization between the probes or primers and the CFS. In some examples, such probes or primers include a sequencing adaptor sequence and/or an experimental tag sequence (or a sequence having complementarity thereto).

In some examples, the kit additionally includes one or more of (such as at least 2, at least 3, at least 4, or at least 5 of): a container containing a buffer (such as a lysis buffer, a plasma lysis buffer; a hybridization buffer, a wash buffer, amplification buffer, denaturation buffer, ligation buffer, elution buffer; and/or a sequencing buffer); a container containing a nuclease specific for single-stranded nucleic acids (such as an S1 nuclease); a container containing ethanol (such as 80% ethanol); a container containing denaturation oil; a container containing proteinase K; a container containing a ligase and a polymerase (for example in a buffer); container containing a DNase (such as DNase I); a container containing a RNase (such as RNase H); a container containing beads that can specifically bind to amplicons (e.g., ligated target amplicons which include a CFS); and container(s) containing reagents for PCR (such as two or more of PCR buffer, polymerase, dNTPs, reverse transcriptase, UDG). In some examples, kits further include control samples, such as samples known to include or exclude a particular nucleic acid molecule. In some examples, kits further include control NPPFs or spike in targets for positive controls.

In some examples, the kit includes NPPFs, CFSs, a digestion solution comprising buffer and S1 enzyme, wash buffer, ligation solution comprising a ligase (and optionally a polymerase) and buffer, a PCR master mix (which can include polymerase, buffer, dNTPs, UDG (optional) reverse transcriptase, primers), a cleanup bead solution, 80% ethanol, elution solution, lysis buffer, denaturation oil, proteinase K, and optionally plasma lysis buffer (for example in separate vials). In some examples such a kit further includes a DNAse (such as DNase I), RNAse (such as RNAse H), or both.

The kits may further include instructional materials. The instructional materials may be written, in an electronic form or may be visual (such as video files).

Example 1

Simultaneous Sequencing of a Plurality of cNPPFs Designed to Detect Nucleic Acid Targets with Single Base Resolution This example describes methods used to generate and sequence cNPPFs (i.e., ligated targets). A set of 24 NPPFs were generated. Each NPPF included a region that was specific for a particular target nucleic acid molecule 50 nucleotides in length with a median $T_m$ of 70.3° C. for all 24 probes, as well as flanking sequences on both ends.

For all NPPFs, regardless of their target, the 5'- and 3'-flanking sequences differed from one another, but each 5' CFS and each 3' CFS was the same on each NPPF. The 5'-flanking sequence (5' TCCCTA-CACGACGCTCTTCCGAUCT 3'; SEQ ID NO: 24) was 25 nucleotides with a $T_m$ of 62.8° C. and the 3'-flanking sequence (5' GAUCGGAAGAGCACACGTCTGAACT 3'; SEQ ID NO: 25) was 25 nucleotides with a $T_m$ of 60.5° C. Each NPPF was designed with two dUTP bases in the flanking sequences. These dUTP bases are designated in SEQ ID NO: 24 and 25 as a "U" (underlined above).

Hybridization was performed on a mixture of target material corresponding to seven of the probes, using the NPPFs described above. Target material input was titrated to provide information on efficiency of ligation. Targets were phosphorylated at their 5' ends.

The different NPPFs were pooled, and hybridized to a dilution series of the targets in solution, as well as to CFSs complementary to the flanking regions on the NPPFs. The 3' CFS carried an internal biotin moiety and was phosphorylated at the 5' end. Hybridization was performed at 50° C. after an initial denaturation at 95° C. for 5 minutes.

Following hybridization, S1 digestion was performed on the hybridized mixture by the addition of S1 enzyme in a buffer. The S1 reaction was incubated at 50° C. for 1 hour.

Following S1-mediated digestion of unhybridized target DNA, NPPFs, and CFSs, the reaction was cooled to room temperature. Subsequently, 10 µl Dynabeads MyOne C1 streptavidin paramagnetic beads (ThermoFisher Scientific) at a concentration of 4 µg/µl were added to the reaction. The beads were incubated with the mixture for 30 minutes at room temperature, allowing the biotin moiety on the 3' CFS to be captured by the streptavidin on the beads.

The beads were washed three times in 50 µl of 1×SSC-T buffer (1×SSC buffer with 0.05% TWEEN® detergent) at room temperature. Washing was performed by placing the reaction tube on a stand magnet to allow the beads to collect, then resuspending the beads in 1×SSC-T. Washing in this mild buffer allows the hybridized structure to remain intact.

The beads were resuspended in 20 µl of ligation mixture containing 200 units of T4 DNA ligase. Ligation proceeded for 1 hour at room temperature. Following the ligation reaction, the beads were washed with 50 µl of dH$_2$O at 50° C. Washing was performed by placing the reaction tube on a stand magnet and allowing the beads to collect, then adding the wash buffer to the beads and incubating the tube at 50° C. for ten minutes. This was repeated twice for a total of three washes. These washes denature the double-stranded product and wash away the NPPFs, leaving the ligated target-CFS complex on the beads. Following washes, the beads were collected a final time and resuspended in 20 µl of dH$_2$O.

Part of the reaction described above, which contained ligated cNPPFs of the original targets used in the sample, was then incubated with PCR primers. One primer included a sequence that was complementary to the 5'-flanking sequence and the second primer included a sequence that was complementary to the 3'-flanking sequence. Both primers also included a sequence to allow for incorporation of an experiment tag into the resulting amplicon, so that each cNPPF in a single sample amplified using these primers had the same two nucleotide experiment tags.

The first primer (5' AATGATACGGCGAC-CACCGAGATCTACACxxxxxxxxACACTCTTTCCCTA-CACGACGCTCTTCCG 3'; SEQ ID NO: 26) was 66 bases in length and carried an eight-nucleotide experimental tag (designated "xxxxxxxx" in the sequence above). Twenty-two of these bases were identical to the 5'-flanking sequence. These 22 bases had a $T_m$ of 60.9° C. The second primer, (5' CAAGCAGAAGACGGCAT-ACGAGATxxxxxxGTGACTGGAGTTCA-GACGTGTGCTCTTCCG 3'; SEQ ID NO: 27) was 60 bases in length and carried a six-nucleotide experimental tag (designated "xxxxxx" in the sequence above). The first 22 nucleotides of the second primer were exactly complementary to the 3'-flanking region and had a $T_m$ of about 59.5° C.

The experimental tags designated as "xxxxxxxx" or "xxxxxx" above were one of the following sequences:

| 5' Barcode sequence (5'-3' in primer) | 3' Barcode sequence (5'-3' in primer) |
|---|---|
| F1 tgaacctt (SEQ ID NO: 28) | |
| F2 ctaatcga (SEQ ID NO: 29) | |
| R1 | gcctaa (SEQ ID NO: 30) |
| R2 | cgtgat (SEQ ID NO: 31) |
| R3 | ggctac (SEQ ID NO: 32) |
| R4 | ctgatc (SEQ ID NO: 33) |
| R5 | tgacca (SEQ ID NO: 34) |
| R6 | cttgta (SEQ ID NO: 35) |

Each reaction was amplified in a separate PCR reaction, and each was amplified with a different combination of experimental tags, so each reaction could be separately identified following sequencing of the pooled reactions. Amplification was preceded by a treatment with uracil DNA deglycosylase (UDG) in all reactions. UDG catalyzes the release of free uracil from uracil-containing DNA, including oligonucleotide or single-stranded DNA. The function of UDG is to destroy any leftover NPPFs present following the previous enzymatic and washing steps. UDG treatment was followed by 20 cycles of PCR.

The resulting amplicons were pooled together and cleaned up using bead-based sample cleanup (AMPure XP from BeckmanCoulter). The amplicons containing the cNPPF and the experimental tags were then sequenced using an ILLUMINA® MiSeq platform. While the experimental tags can be located in several places, in this example, they was located at both sides of the amplicon, immediately downstream of a region complimentary to an index-read sequencing primer. ILLUMINA® sequencing was thus done in three steps, an initial read of the sequence followed by two shorter reads of the experimental tags using two other sequencing primers (all sequencing primers were included in the standard ILLUMINA® kit). The sequencing method described herein and used is a standard method for multiplexing samples on an ILLUMINA® platform.

Each molecule sequenced was sorted based first on the experiment tags, and then within each experiment tag group, the number of molecules identified for each of the different tags was counted. The amplicons were compared to the expected sequences using the open-source software bowtie (Langmead et al., Ultrafast and memory-efficient alignment of short DNA sequences to the human genome. *Genome Biol* 10:R25).

Figure 7A:
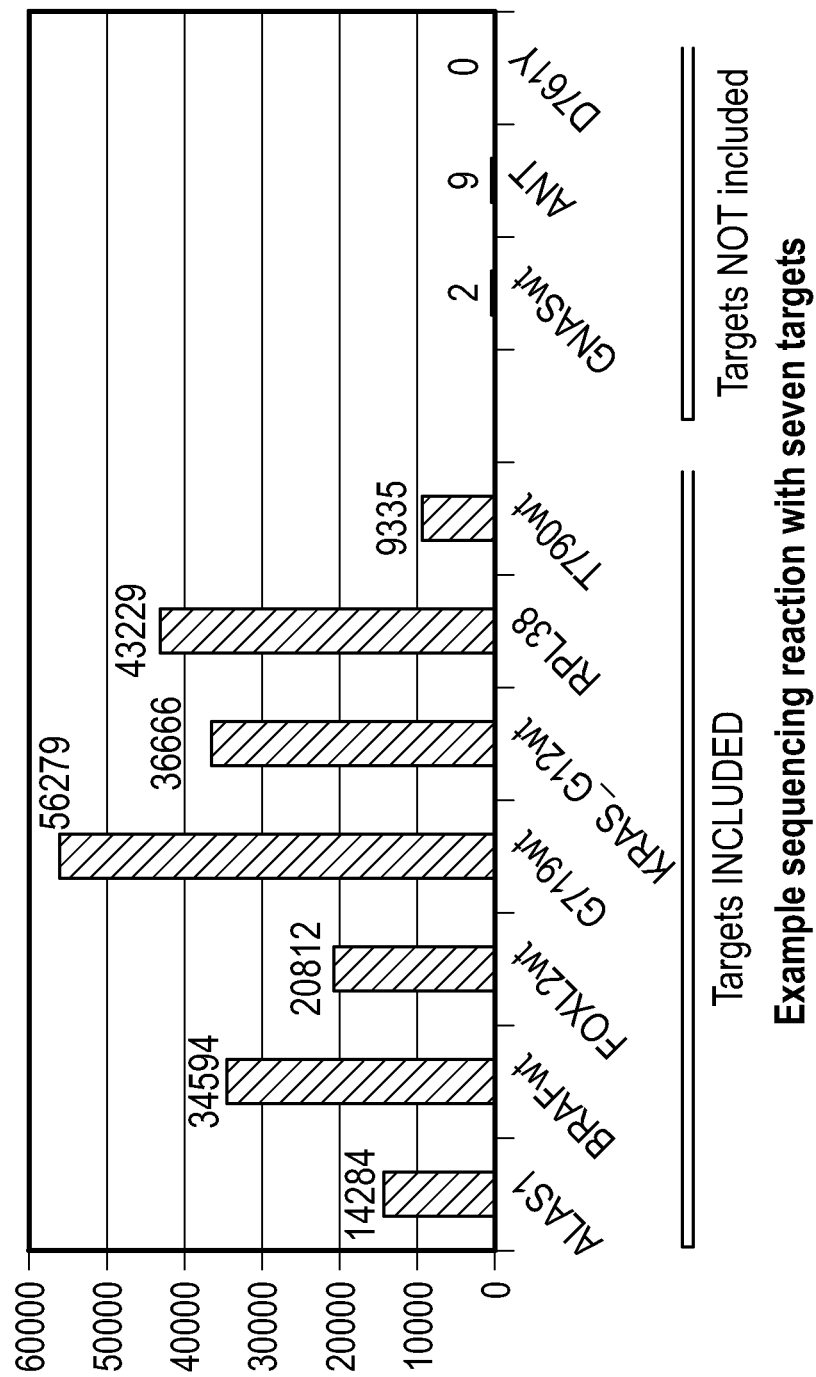
FIG. 7A is a bar graph showing the results of sequencing seven different targets using the disclosed methods.
Figure 7B:
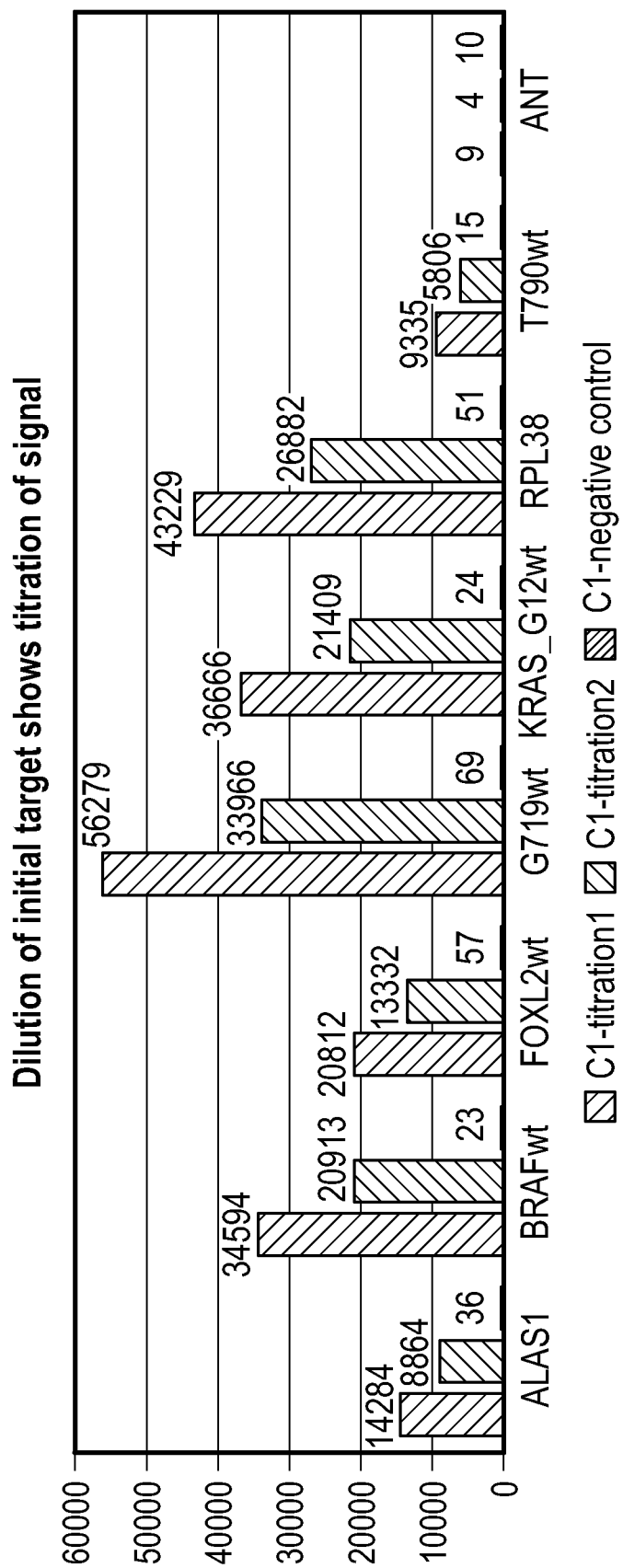
FIG. 7B is a bar graph showing the results of titrating sequencing seven different targets using the disclosed methods.
Figure 8:
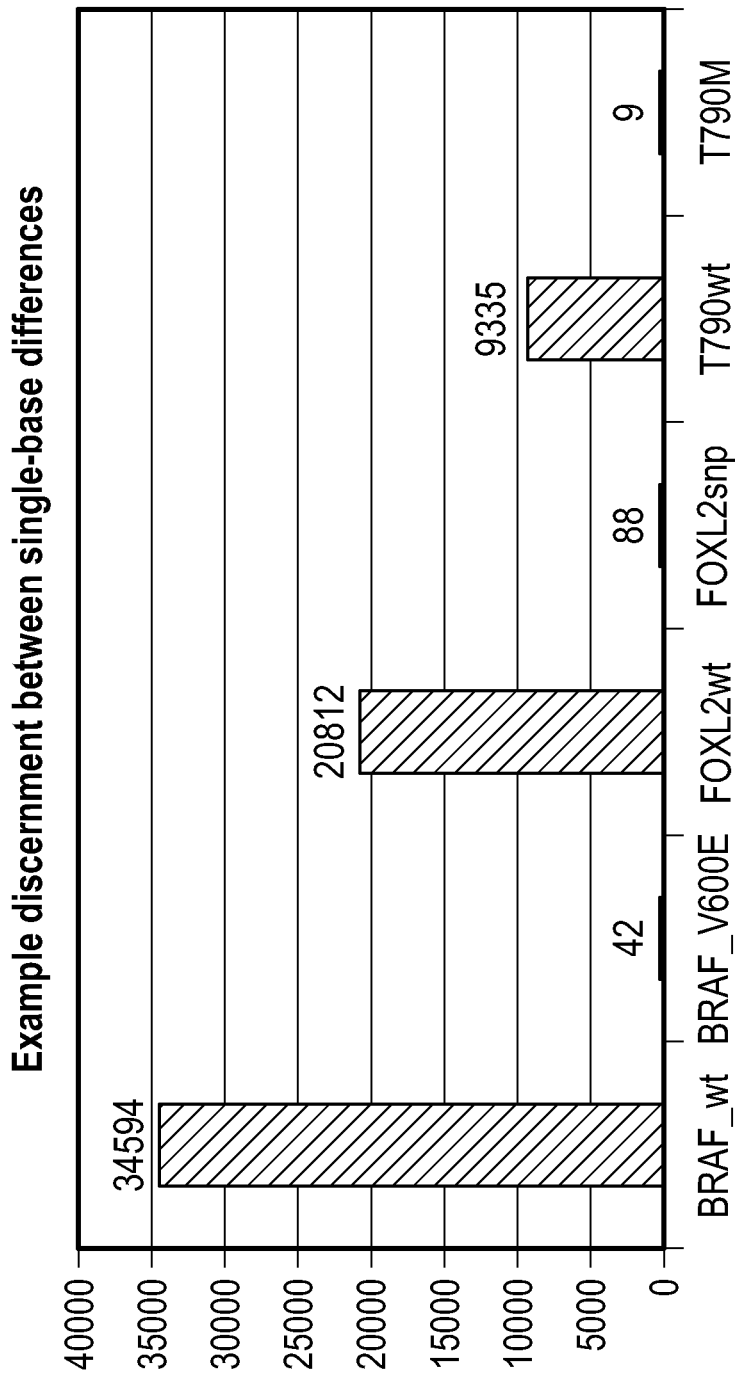
FIG. 8 is a bar graph showing the ability of the disclosed methods to discern single nucleotide variations.

FIGS. 7A-7B and FIG. 8 show the results from sequencing the ligated targets and CFSs. The graphs represents the number of amplicons detected for each of the 7 unique NPPFs corresponding to the targets added to the initial hybridization reaction. Only seven targets were added to the reaction. These were expected to have signal in the sequencing reaction, but no other signals were expected; the other 17 probes were negative controls with no target present and were not expected to generate a signal. The results were aligned to all sequences (regardless of whether a target was included for them or not). FIG. 7A shows that added targets resulted in significant detectable signal, while the others did not generate a significant signal. Raw counts are shown.

A titration of input material was added to the hybridization, and thus the target signals should represent the dilution. FIG. 7B shows the change between two reactions with two-fold differences in target input, and they indeed titrate in all seven cases. A negative control reaction with no added target is also shown (ANT). In all cases, the numbers represent raw counts.

These results indicate that the disclosed method can discern between single-base changes. Six of the 24 NPPFs were designed for wild type (WT)/single base mutation pairs. Three of the seven targets added to the hybridization matched the WT version of the probe. FIG. 8 shows the total counts identified for the WT/SNP pairs (raw counts are shown). The wild type (WT) sequence was identified but not the SNP sequence, demonstrating that this method is able to discern single base differences.

Example 2

Exemplary NPPF Designs

This example describes methods used to generate and sequence cNPPFs using two different NPPF design strategies. In both mixtures, each NPPF included a 50 nucleotide region that was specific for a particular target nucleic acid molecule.

In the first mixture, specific individual NPPFs were generated for each allele and each nucleotide difference of that allele being measured. For example, for the BRAF V600E mutation, an NPPF was generated specifically for the wild type (the nucleotide corresponding to BRAF 1799 is dTTP or T) allele and another specifically for the mutant allele (nucleotide 1799 is dATP or A). Twenty-four NPPFs were generated in this manner, such that each NPPF was designed for a specific target with 100% base complementarity.

In the second mixture, one NPPF was designed for each allele, but the probe was designed to be 100% complementary only to the mutant target (for example, for BRAF V600E, the nucleotide corresponding to position 1799 of BRAF was A). The NPPF was thus not designed to be 100% complementary to the wild type allele, or to any other allele that might carry unknown changes. Twelve such NPPFs were generated.

For all NPPFs in both mixes, although the 5'- and 3'-flanking sequences differed from one another, each 5' flanking sequence and each 3' flanking sequence was the same on each NPPF. The 5' flanking sequence (5' TCCCTACACGACGCTCTTCCGAUCT 3'; SEQ ID NO: 24) was 25 nucleotides with a $T_m$ of 62.8° C. and the 3' flanking sequence (5' GAUCGGAAGAGCACACGTCTGAACT 3'; SEQ ID NO: 25) was 25 nucleotides with a $T_m$ of 60.5° C. Each NPPF was designed with two dUTP bases in the flanking sequences. These dUTP bases are designated in the sequences above with a "U".

A set of test samples was generated utilizing twelve double-stranded DNA amplicons. Each amplicon carried a target sequence complementary to a wild type or a mutant NPPF. Each amplicon contained additional, non-target sequences. Wild type and mutant target amplicons (6 each) were mixed together in a ratios dilution series (final concentration of amplicons was the same, but the makeup differed, see Table 1) to form seven different samples:

TABLE 1

| Dilution Series | | |
|---|---|---|
| Sample number | WT amplicons | Mut amplicons |
| 1 | 100% | 0% |
| 2 | 90% | 10% |
| 3 | 80% | 20% |
| 4 | 50% | 50% |
| 5 | 20% | 80% |
| 6 | 10% | 90% |
| 7 | 0% | 100% |

Each of the two sets of NPPFs described above were mixed together with CFSs complementary to the flanking regions on the NPPFs. The 3' CFS carried an internal biotin moiety and the 5' CFS was phosphorylated at the 5' end. NPPFs and CFSs were then hybridized to the amplicon samples. For each NPPF set, each sample was run in triplicate. Hybridization of the NPPFs to their targets was performed in solution at 50° C. after an initial denaturation at 95° C. for 10 minutes.

Following hybridization, S1 digestion was performed on the hybridized mixture by the addition of S1 enzyme in a buffer. The S1 reaction was incubated at 50° C. for 90 minutes. Following S1-mediated digestion of single-stranded nucleic acids (including unhybridized DNA, NPPFs, and CFSs), the reaction was cooled to room temperature and added to 5 μl Dynabeads MyOne C1 Streptavidin paramagnetic beads (ThermoFisher Scientific) at a concentration of 4 μg/μl. The beads were incubated with the mixture for 30 minutes at room temperature, allowing the biotin moiety on the 3' CFS to be captured by the streptavidin on the beads.

The beads were washed three times in 150 μl of 1×SSC-T buffer (1×SSC buffer with 0.05% TWEEN® detergent) at room temperature. Washing in this mild buffer allows the hybridized structure to remain intact. Washing was performed by placing the reaction tube on a stand magnet to allow the beads to collect, removing the supernatant, then resuspending the beads in 1×SSC-T.

The washed beads were resuspended in 20 µl of ligation mixture containing 80 units of T4 DNA Ligase and 0.6 units of T4 DNA Polymerase in T4 DNA Ligase buffer (enzymes and buffer from New England Biolabs) supplemented with dNTPs. Ligation proceeded for 1 hour at room temperature. Following the ligation reaction, the beads were washed three times with 150 µl of 0.02% TWEEN® detergent. Washing was performed by placing the reaction tube on a stand magnet to allow the beads to collect, removing the supernatant, then resuspending the beads in 1×SSC-T and incubating the tube at 50° C. for 10 minutes. These washes denature the double-stranded product and wash away the NPPFs, leaving the ligated target-CFS complex on the beads. The beads were resuspended in 20 µl of 0.02% TWEEN® detergent prior to amplification.

Part of the reaction described above, which contained ligated cNPPFs of the original targets used in the sample, was then incubated with PCR primers. One primer included a sequence that was identical to the 5'-flanking sequence of the NPPF and the second primer included a sequence that was complementary to the 3'-flanking sequence of the NPPF. Both primers also included a sequence to allow for incorporation of an experiment tag into the resulting amplicon, so that each cNPPF in a single sample amplified using these primers had the same two nucleotide experiment tags.

The first primer (5' AATGATACGGCGACCACCGAGATCTA-CACxxxxxxxxACACTCTTTCCCTA-CACGACGCTCTTCCG 3'; SEQ ID NO: 26) was 66 bases in length and carried an eight-nucleotide experimental tag (designated "xxxxxxxx" in the sequence above). Twenty-two of these bases were identical to the 5' flanking sequence of the NPPF. These 22 bases had a T$_m$ of 60.9° C.

The second primer, (5' CAAGCAGAAGACGGCAT-ACGAGATxxxxxxGTGACTGGAGTTCA-GACGTGTGCTCTTCCG 3'; SEQ ID NO: 27) was 60 bases in length and carried a six-nucleotide experimental tag (designated "xxxxxx" in the sequence above). The first 22 nucleotides of the second primer were exactly complementary to the 3' flanking sequence of the NPPF and had a T$_m$ of about 59.5° C.

The experimental tags designated as "xxxxxxxx" or "xxxxxx" above were one of the sequences shown in Table 2.

TABLE 2

Exemplary barcode sequences

| 5' primer number | 5' Barcode sequence (5'-3' in primer) | 3' primer number | 3' Barcode sequence (5'-3' in primer) |
|---|---|---|---|
| F1 | CTAATCGA (SEQ ID NO: 29) | R1 | CGATGT (SEQ ID NO: 41) |
| F2 | ATAGAGGC (SEQ ID NO: 36) | R2 | GCCAAT (SEQ ID NO: 42) |
| F3 | GGCTCTGA (SEQ ID NO: 37) | R3 | CAGATC (SEQ ID NO: 43) |
| F4 | TATAGCCT (SEQ ID NO: 38) | R4 | GCCTAA (SEQ ID NO: 44) |

TABLE 2-continued

Exemplary barcode sequences

| 5' primer number | 5' Barcode sequence (5'-3' in primer) | 3' primer number | 3' Barcode sequence (5'-3' in primer) |
|---|---|---|---|
| F5 | CCTATCCT (SEQ ID NO: 39) | R5 | CACTGT (SEQ ID NO: 45) |
| F6 | AGGCGAAG (SEQ ID NO: 40) | R6 | ATTGGC (SEQ ID NO: 46) |
|  |  | R7 | TCAAGT (SEQ ID NO: 47) |
|  |  | R8 | CGTACG (SEQ ID NO: 48) |

Each reaction was amplified in a separate PCR reaction, and each was amplified with a different combination of experimental tags (one 5' primer and one 3' primer), so each reaction could be separately identified following sequencing of the pooled reactions. Amplification was preceded by a treatment with uracil DNA deglycosylase (UDG) in all reactions. UDG catalyzes the release of free uracil from uracil-containing DNA, including oligonucleotide or single-stranded DNA. In the reactions described, the function of UDG is to destroy any leftover NPPFs present following the previous enzymatic and washing steps. UDG treatment was followed by 22 cycles of PCR.

The resulting PCR reactions were pooled together and cleaned up using bead-based sample cleanup (AMPure XP from BeckmanCoulter). The amplicons containing the cNPPFs and the experimental tags were then sequenced using an ILLUMINA® MiSeq platform. While the experimental tags can be located in several places, in this example, they was located at both sides of the amplicon, immediately downstream of a region complimentary to an index-read sequencing primer. ILLUMINA® sequencing was thus done in three steps, an initial read of the sequence followed by two shorter reads of the experimental tags using two other sequencing primers (all sequencing primers were included in the standard ILLUMINA® kit). The sequencing method described herein and used is a standard method for multiplexing samples on an ILLUMINA® platform.

Each molecule sequenced was sorted based first on the experiment tags, and then within each experiment tag group, the number of molecules identified for each of the different tags was counted. The amplicons were compared to the expected sequences using the open-source software bowtie (Langmead et al., *Genome Biol* 10: R25).

Figure 11A:
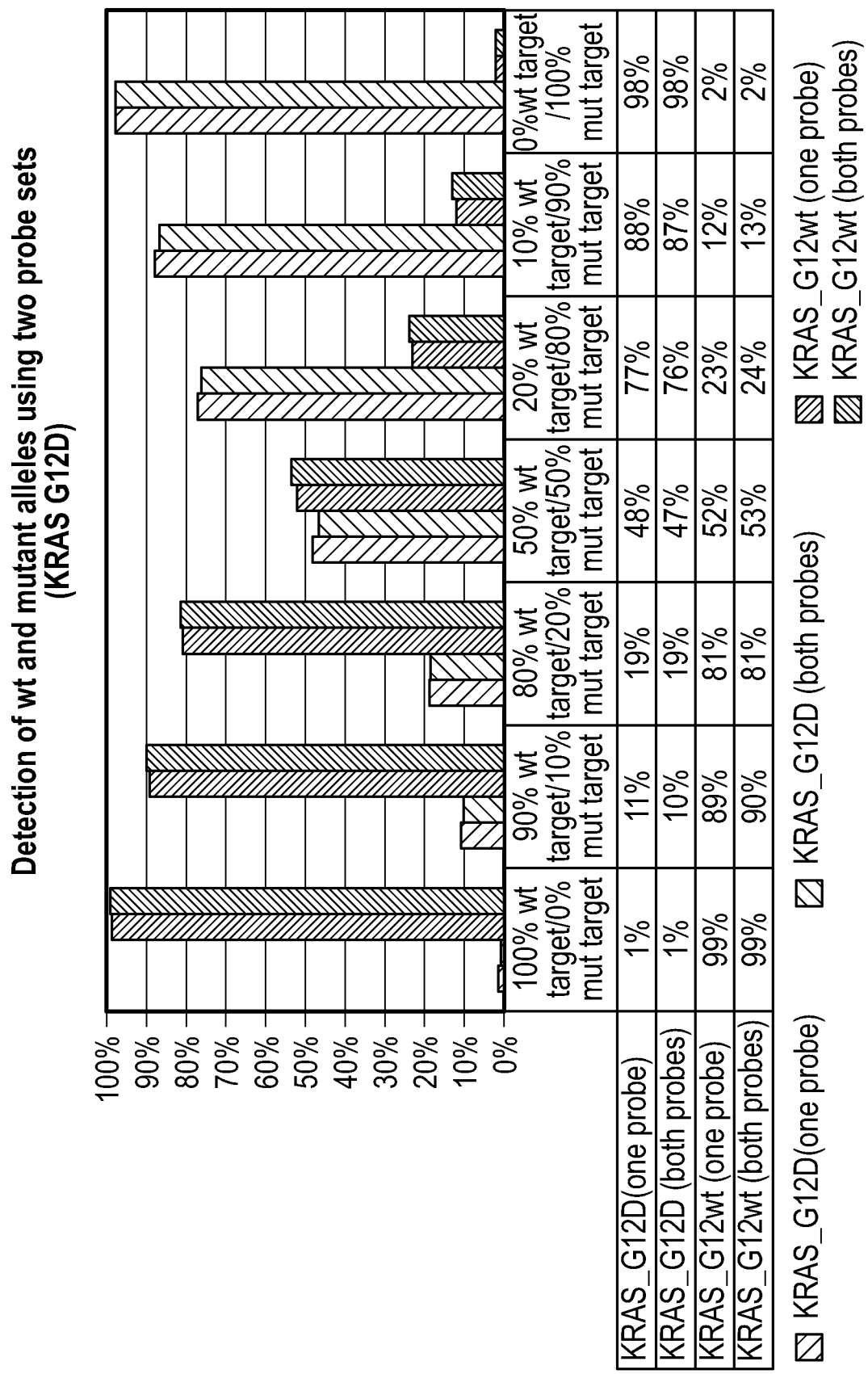
FIGS. 11A-11B are bar graphs showing the ability of the disclosed methods to discern single nucleotide variations of (A) KRAS or (B) BRAF using two different probe designs.
Figure 11B:
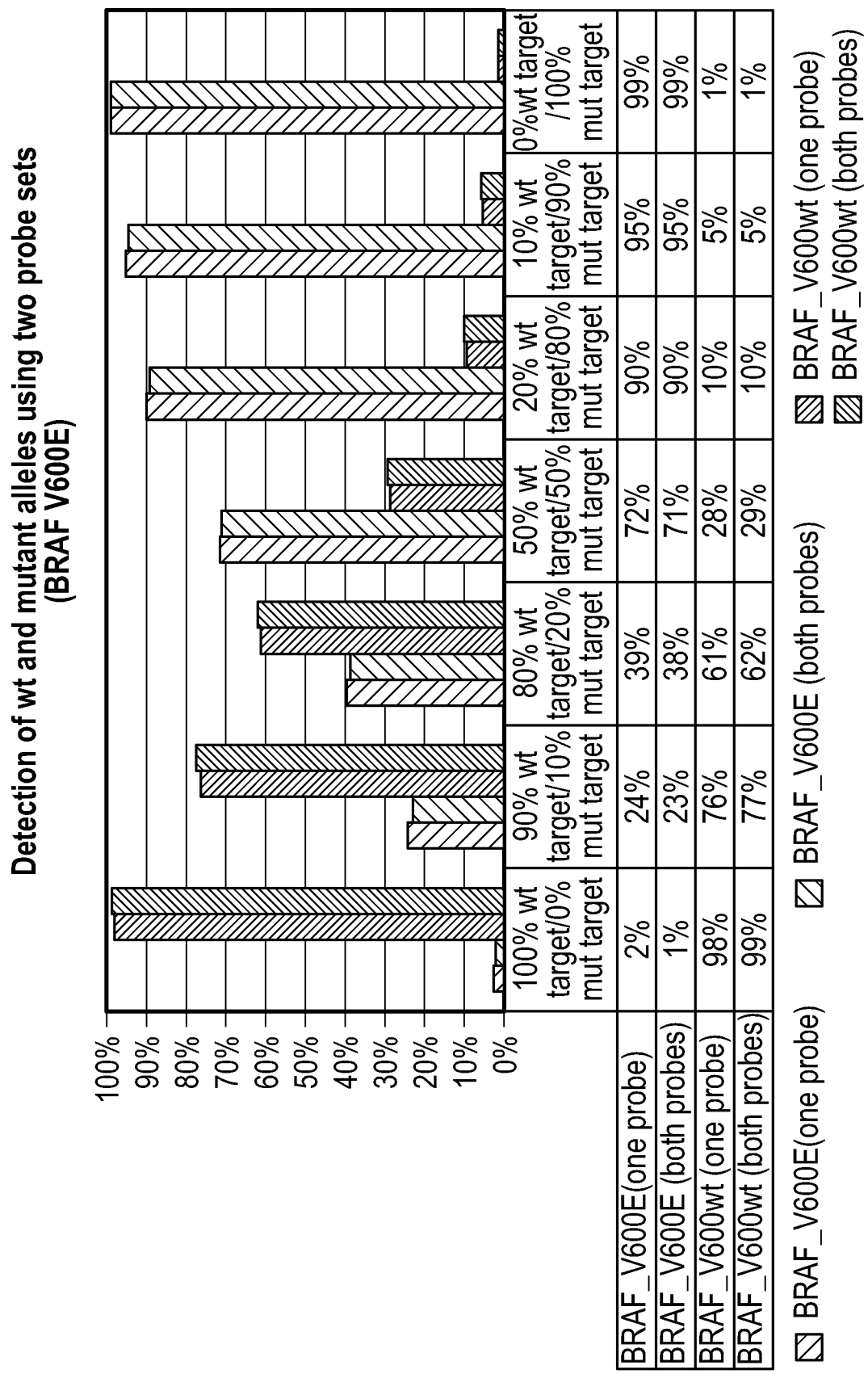

FIGS. 11A-11B show the results from sequencing the ligated targets and CFSs (cNPPFs). The graph represents the relative percentage of wild type and mutant amplicons detected in the eight samples, using the two sets of NPPFs (either a specific probe for both wild type and mutant ("both probes"), or just one probe for both ("one probe")). Raw data generated from triplicate samples were averaged to generate the numbers, then all signal for a given NPPF was set equal to 100% and the relative percentages of wild type and mutant alleles are shown as a proportion of that 100%. Both a graph and a table showing the percentages are shown. Two wild type/mutant amplicon sample dilution sets (for KRAS and BRAF) are shown (FIG. 11A and FIG. 11B, respectively).

As shown in FIGS. 11A-11B, the ratio of wild type and mutant amplicons within each sample mixture is nearly identical when using either of the two NPPF mixtures (see the table under the graph for exact numbers). This demonstrates that an NPPF with a small number of nucleotide differences (e.g., 1, 2, 3, 4 or 5 mismatches) between the NPPF and the target will still hybridize to the target and protect the target through nuclease digestion. This occurs with no meaningful loss of the target that does not exactly match the probe (compare detection of the wild type amplicon in both probe sets). This demonstrates that an NPPF can be used for both known differences and for limited discovery of mutations within a region that were not expected, i.e. de novo mutations. Not only does this allow more flexibility in an assay, it also reduces probe design time, build costs, and increases robustness in the system by simplifying the components.

Example 3

Simultaneous Sequencing of a Plurality of cNPPFs Designed to Target a Specific Region and Identify Nucleic Acid Variants within that Region in Cell Lines of Known Mutational Status This example describes methods used to assess the genomic KRAS mutation status in a set of cell line samples with known KRAS mutational status. Further, it describes a NPPF design that differentiates between probe and target, and which allows identification of unknown mutations within a target region.

Three commercially-available cell lines were used. COLO-205 ("KRAS WT" line) carries a BRAF 1799T>A base change (V600E amino acid change) but is wild type for KRAS. NCI-H1155 ("KRAS mut" line) carries the KRAS 183A>T base change (Q61H_T) and is homozygous for this mutant allele. SW948 ("KRAS heterozygous") carries both a WT allele of KRAS and a 182A>C mutant allele (Q61L). Cell lines were diluted in a lysis buffer.

A set of 19 NPPFs were generated. The design of these NPPFs builds on Example 2, where it was shown that a mismatch within a probe does not change the ability of the probe to serve as a hybridization scaffold for a target that differs by one or more bases. Each NPPF included a region that was specific for a particular target nucleic acid molecule 50 nucleotides in length with a median $T_m$ of 71.0° C. for all 19 regions, as well as flanking sequences on both ends. Each probe also includes a single mismatch relative to the genomic target sequence. In these cases, the mismatch was placed in the 5' third of the protection sequence within the NPPF. Either a C>T or a A>G change was used as the mismatch.

For all NPPFs, regardless of their intended target, although the 5'- and 3'-flanking sequences differed from one another, each 5' flanking sequence and each 3' flanking sequence was the same on each NPPF. The 5'-flanking sequence (5' TCCCTACACGACGCTCTTCCGAUCT 3' SEQ ID NO: 24) was 25 nucleotides with a $T_m$ of 62.8° C. and the 3'-flanking sequence (5' GAUCGGAAGAGCACACGTCTGAACT 3' SEQ ID NO: 25) was 25 nucleotides with a $T_m$ of 60.5° C. Each NPPF was designed with a total of four dUTP bases. Two dUTP bases were located in the flanking sequences. These dUTP bases are designated in the sequences above with a "U". An additional two dUTP bases were placed within the target-specific region of the NPPF. The location of these dUTP bases varies dependent on the placement of dTTP bases within the target-specific protection sequence. The different NPPFs were pooled with CFSs complementary to the flanking regions on the NPPFs. The 5' CFS was phosphorylated at the 5' end and the 3' CFS carried an internal biotin moiety.

Cell line lysates were run in triplicate; each replicate contained 5000 cells in a lysis buffer. Lysates were mixed with the NPPF and CFS mixture described above and hybridization was performed for 18 hours at 50° C. after an initial denaturation at 95° C. for 10 minutes.

Following hybridization, S1 digestion was performed on the hybridized mixture by the addition of S1 enzyme in a buffer. The S1 reaction was incubated at 50° C. for 90 minutes. Following S1-mediated digestion, the reaction was cooled to room temperature. At that point, the reaction was added to 5 µl Dynabeads MyOne C1 Streptavidin paramagnetic beads (ThermoFisher Scientific) at a concentration of 4 µg/µl in a buffer. The beads were incubated with the mixture for 30 minutes at room temperature, allowing the biotin moiety on the 3' CFS to be captured by the streptavidin on the beads.

The beads were washed three times in 150 µl of 1×SSC-T buffer (1×SSC buffer with 0.05% TWEEN® detergent) at room temperature. Washing in this mild buffer allows the hybridized structure to remain intact. Washing was performed by placing the reaction tube on a stand magnet to allow the beads to collect, removing the supernatant, then resuspending the beads in 1×SSC-T.

The washed beads were resuspended in 20 µl of ligation mixture containing 80 units of T4 DNA Ligase and 0.6 units of T4 DNA Polymerase in T4 DNA Ligase buffer (enzymes and buffer from New England Biolabs) supplemented with dNTPs. Ligation proceeded for 1 hour at room temperature. Following the ligation reaction, the beads were washed three times with 150 µl of 50% formamide/0.02% TWEEN® polysorbate 20 detergent and once in 150 µl of 0.02% TWEEN® polysorbate 20 detergent. These washes denature the double-stranded product and wash away the NPPFs, leaving the ligated target-CFS complex on the beads. Washes were performed by placing the reaction tube on a stand magnet to allow the beads to collect, removing the supernatant, then resuspending the beads in wash buffer. Washed beads were resuspended in 20 µl of 0.02% TWEEN® detergent prior to amplification.

Part of the reaction described above, which contained ligated cNPPFs of the targets in the sample, was then incubated with PCR primers. These primers were designed as described in Example 2. The experimental tags used are shown in Table 3.

TABLE 3

Exemplary experimental tags.

| 5' primer number | 5' Barcode sequence (5'-3' in primer) | 3' primer number | 3' Barcode sequence (5'-3' in primer) |
|---|---|---|---|
| F1 | CTAATCGA (SEQ ID NO: 29) | R1 | ACATCG (SEQ ID NO: 49) |
| F2 | ATAGAGGC (SEQ ID NO: 36) | R2 | GGCTAC (SEQ ID NO: 32) |
| F3 | GGCTCTGA (SEQ ID NO: 37) | R3 | CTTGTA (SEQ ID NO: 35) |

Each reaction was amplified in a separate PCR reaction, and each was amplified with a different combination of experimental tags (one 5' primer and one 3' primer), so each reaction could be separately identified following sequencing of the pooled reactions. Amplification was preceded by a treatment with uracil DNA deglycosylase (UDG) in all reactions. UDG catalyzes the release of free uracil from uracil-containing DNA, including oligonucleotide or single-stranded DNA. In the reactions described, the function of UDG is to destroy any leftover NPPFs present following the previous enzymatic and washing steps. UDG treatment was followed by 22 cycles of PCR.

The resulting amplicons were pooled together and cleaned up using bead-based sample cleanup (AMPure XP from BeckmanCoulter). The amplicons containing the cNPPF and the experimental tags were then sequenced using an ILLUMINA® NextSeq platform. While the experimental tags can be located in several places, in this example, they was located at both sides of the amplicon, immediately downstream of a region complimentary to an index-read sequencing primer. ILLUMINA® sequencing was thus done in three steps, an initial read of the sequence followed by two shorter reads of the experimental tags using two other sequencing primers (all sequencing primers were included in the standard ILLUMINA® kit). The sequencing method described herein and used is a standard method for multiplexing samples on an ILLUMINA® platform.

Each molecule sequenced was sorted based first on the experiment tags, and then within each experiment tag group, the number of molecules identified for each of the different tags was counted. The amplicons were compared to the expected sequences using the open-source software bowtie.

Figure 12:
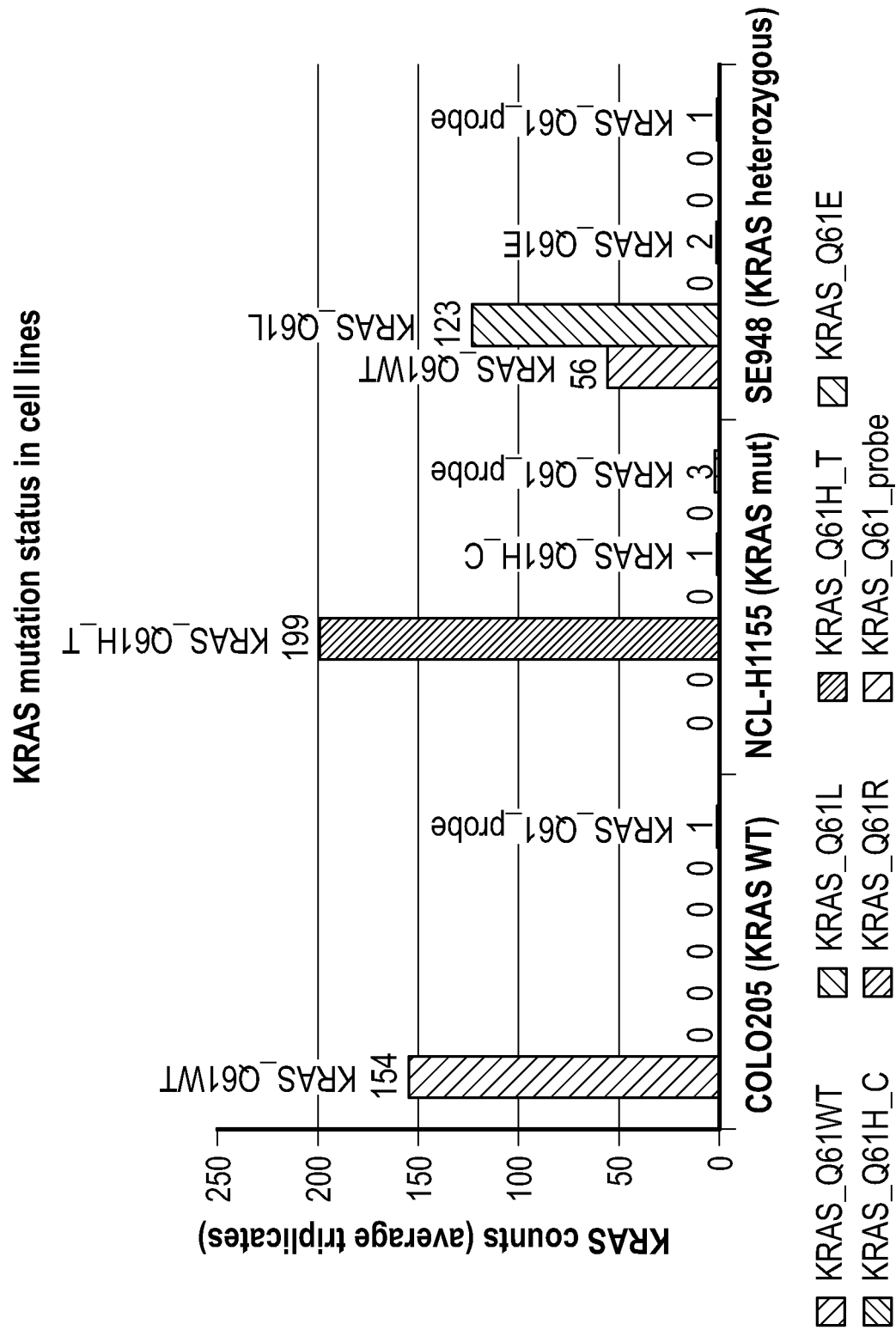
FIG. 12 is a bar graph showing the ability of the disclosed methods to discern expected target nucleotide variations within cell lines of known genomic mutational status.

FIG. 12 shows the results from sequencing the reactions. To obtain the graph, raw data from triplicate samples were averaged and all sequenced counts for the Q61 region were graphed by allele. Counts that resulted from only the probe are also shown, although no meaningful signal was detected (see "KRAS_Q61_probe" in FIG. 12).

These results demonstrate the effectiveness of the single-probe design for detecting variant or wild type alleles within the assessed sample—while various mutation in the KRAS Q61 region were assessed, a single NPPF was used. Thus, although the NPPFs are non-specific, the assay results from sequencing the captured targets (cNPPFs) are highly specific. Specificity of the assay is demonstrated by the correct detection of the specific expected KRAS alleles within known cell lines; additionally, for equivalent cellular input of all three cell lines, the amount of total KRAS signal detected was roughly equivalent between cell lines, regardless of allele status. Since the results are generated by sequencing, any unexpected mutations in the target region (none were detected, see FIG. 12) can also be identified or discovered.

Specificity is negatively impacted by false positive or false negative signals. Thus, even though the NPPF design includes a base mismatch between the NPPF and the target region, this mismatch is placed away from the region of known interest, and allows any false signal resulting from residual probe presence (within the assay or from environmental contamination in the PCR setup area) to be screened out of the results. In this experiment, there was no detectable probe sequence (see FIG. 12, "KRAS_Q61_probe").

Example 4

Simultaneous Sequencing of a Plurality of cNPPFs; Linearity, Specificity and Sensitivity in a Multiplexed Reaction This example describes methods used to generate and sequence cNPPFs. A set of 30 NPPFs were generated. Each NPPF included a region that was specific for a particular target nucleic acid molecule (50 nucleotides in length), as well as flanking sequences on both ends. NPPFs were designed as in Example 3. The NPPFs were pooled with CFSs complementary to the flanking regions on the NPPFs. The 3' CFS carried an internal biotin moiety and the 5' CFS was phosphorylated at the 5' end.

Hybridization was performed on a mixture of 23 double-stranded DNA amplicons that contained target sequences. Each amplicon carried either a wild type or a mutant copy of a known human allele, as well as additional non-target sequences. All 23 amplicons were pooled together at a high concentration and then the pool was diluted in a lysis buffer. Seven dilutions, ranging from 100 fM to 100 aM were generated. This dilution series was then used to test the reproducibility, linearity, sensitivity, and specificity of the assay in multiplex, using the NPPF pool described above. Hybridization was performed in solution, by mixing the NPPF and CFSs with amplicon sample. Hybridization was performed at 50° C. after an initial denaturation at 95° C. for 10 minutes.

Following hybridization, S1 digestion was performed on the hybridized mixture by the addition of S1 enzyme in a buffer. The S1 reaction was incubated at 50° C. for 90 minutes. Following S1-mediated digestion of single-stranded nucleic acids (including unhybridized DNA, NPPFs, and CFSs), the reaction was cooled to room temperature and added to 5 µl Dynabeads MyOne C1 Streptavidin paramagnetic beads (ThermoFisher Scientific) at a concentration of 4 µg/µl. Beads and sample mixture were incubated for 30 minutes at room temperature, allowing the biotin moiety on the 3' CFS to be captured by the streptavidin on the beads. This step also serves to stop the S1 reaction.

The beads were washed three times in 150 µl of 1×SSC-T buffer (1×SSC buffer with 0.05% TWEEN® detergent) at room temperature. Washing in this mild buffer allows the hybridized structure to remain intact. Washing was performed by placing the reaction tube on a stand magnet to allow the beads to collect, removing the supernatant, then resuspending the beads in 1×SSC-T.

Washed beads were resuspended in 20 µl of ligation mixture containing 80 units of T4 DNA Ligase and 0.6 units of T4 DNA Polymerase. Ligation proceeded for 75 minutes at room temperature. Following the ligation reaction, the beads were washed three times with 150 µl of 50% formamide in 0.02% TWEEN® polysorbate 20 detergent, followed by one wash in 0.02% TWEEN® polysorbate 20 detergent in dH$_2$O. Washing was performed by placing the reaction tube on a stand magnet and allowing the beads to collect, removing the supernatant, then adding the wash buffer to the beads. These washes denature the double-stranded product and wash away the NPPFs, leaving the ligated target-CFS complex on the beads. Washed beads were resuspended in 20 µl of 0.02% TWEEN® polysorbate 20 detergent in dH$_2$O prior to amplification.

Part of the reaction described above, which contained ligated cNPPFs of the original targets used in the sample, was then incubated with PCR primers. These primers were designed as described in Example 2. The experimental tags used are shown in Table 4.

TABLE 4

Exemplary barcode sequences

| 5' primer number | 5' Barcode sequence (5'-3' in primer) | 3' primer number | 3' Barcode sequence (5'-3' in primer) |
|---|---|---|---|
| F1 | TGAACCTT (SEQ ID NO: 28) | R1 | TGACCA (SEQ ID NO: 34) |

TABLE 4-continued

Exemplary barcode sequences

| 5' primer number | 5' Barcode sequence (5'-3' in primer) | 3' primer number | 3' Barcode sequence (5'-3' in primer) |
|---|---|---|---|
| F2 | CTAATCGA (SEQ ID NO: 29) | R2 | AAGCTA (SEQ ID NO: 52) |
| F3 | ATAGAGGC (SEQ ID NO: 36) | R3 | ACTTGA (SEQ ID NO: 53) |
| F4 | GGCTCTGA (SEQ ID NO: 37) | | |
| F5 | CCTATCCT (SEQ ID NO: 39) | | |
| F6 | AGGCGAAG (SEQ ID NO: 40) | | |
| F7 | TAATCTTA (SEQ ID NO: 50) | | |
| F8 | CAGGACGT (SEQ ID NO: 51) | | |

Each reaction was amplified in a separate PCR reaction, and each was amplified with a different combination of experimental tags (one 5' primer and one 3' primer), so each reaction could be separately identified following sequencing of the pooled reactions. Amplification was preceded by a treatment with uracil DNA deglycosylase (UDG) in all reactions. UDG catalyzes the release of free uracil from uracil-containing DNA, including oligonucleotide or single-stranded DNA. In the reactions described, the function of UDG is to destroy any leftover NPPFs present following the previous enzymatic and washing steps. UDG treatment was followed by 22 cycles of PCR.

The resulting PCR reactions were pooled together and cleaned up using bead-based sample cleanup (AMPure XP from BeckmanCoulter). Pooling was performed so that the titration samples could be analyzed relative to one another (i.e., a higher titration would have more input material into the sequencing run than a lower one). The amplicons containing the cNPPFs and the experimental tags were then sequenced using an ILLUMINA® MiSeq platform. While the experimental tags can be located in several places, in this example, they was located at both sides of the amplicon, immediately downstream of a region complimentary to an index-read sequencing primer. ILLUMINA® sequencing was thus done in three steps, an initial read of the sequence followed by two shorter reads of the experimental tags using two other sequencing primers (all sequencing primers were included in the standard ILLUMINA® kit). The sequencing method described herein and used is a standard method for multiplexing samples on an ILLUMINA® platform.

Each molecule sequenced was sorted based first on the experiment tags, and then within each experiment tag group, the number of molecules identified for each of the different tags was counted. Sequences obtained were compared to the expected sequences using the open-source software bowtie.

Figure 13A:
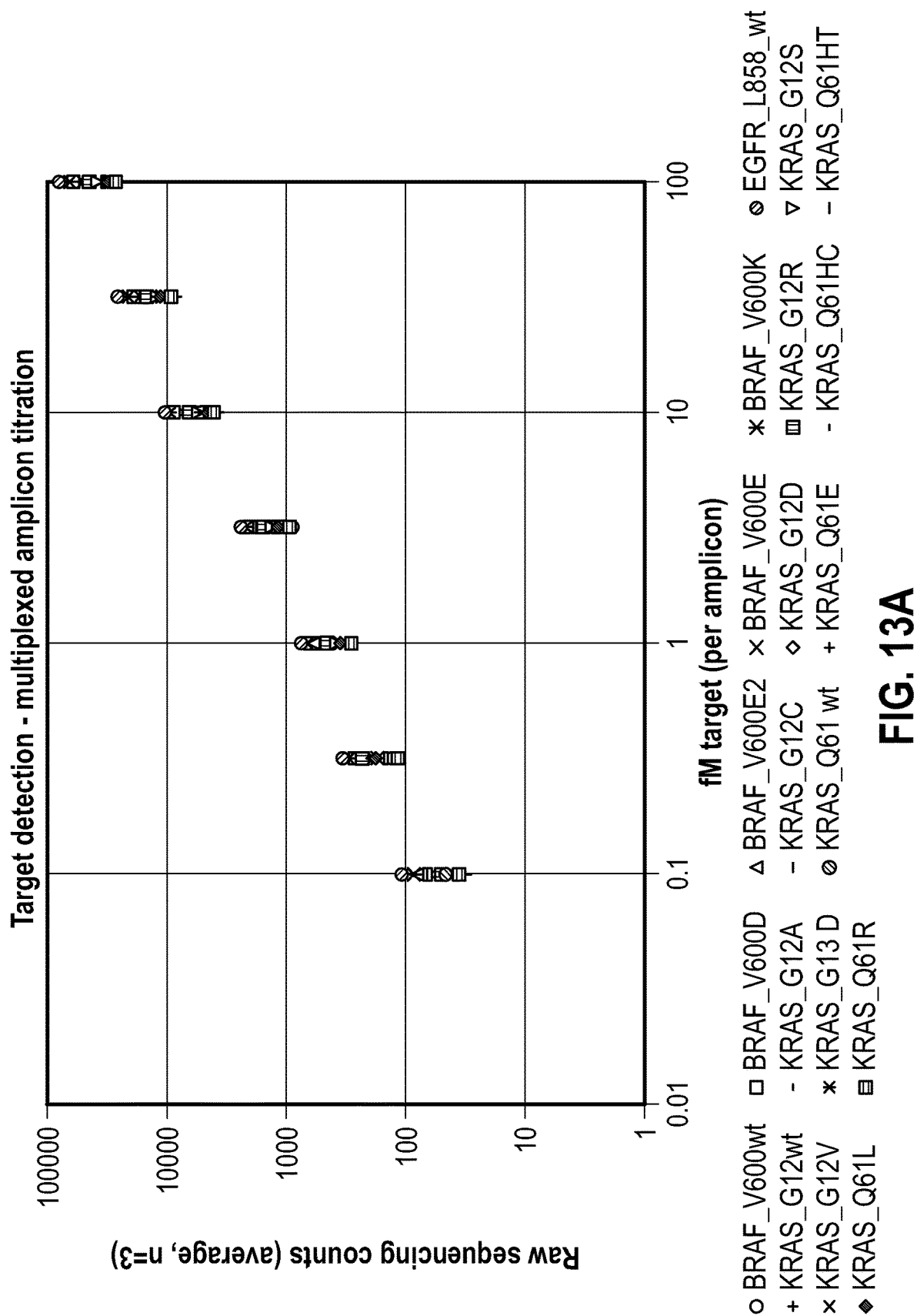
FIGS. 13A-13B are graphs showing the ability of the disclosed methods to discern nucleotide variations over a range of input concentrations, in multiplex. Detection and linearity of (A) twenty amplicons or (B) two amplicons in more detail are shown.
Figure 13B:
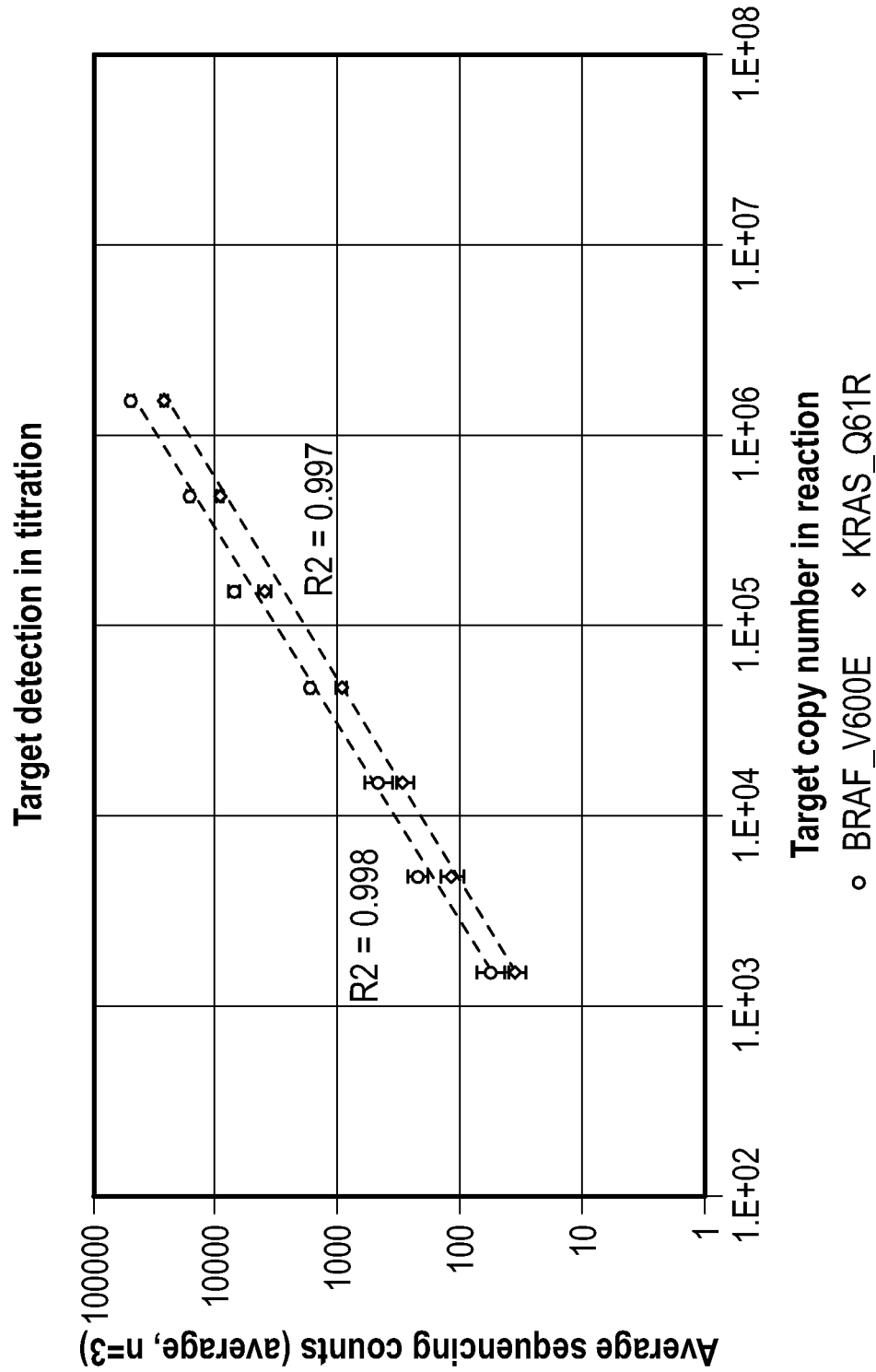

FIGS. 13A-13B and 14 show the results from sequencing the ligated targets and CFSs (cNPPFs). This was a multi-plexed sample, containing 23 amplicon targets. There were NPPFs within the reaction designed to detect 20 of the 23 amplicon targets, and all 20 were detected, demonstrating the ability of the assay to perform multiplexed detection of targets with small changes.

In addition, each amplicon was titrated over a three-log scale, and linearity was measured for each of the 20 amplicons. Data for all 20 amplicons are plotted in FIG. 13A (raw data, average of triplicates, log 10 scale), showing the linearity of all 20 amplicons. The data are highly linear—the median $R^2$ of the data from the seven titration points for all 20 amplicons was 0.998 (range 0.997-0.99, linear scale).

FIG. 13B demonstrates the reproducibility, linearity, sensitivity, and specificity of detection over the range of 1500-1.5M input copies. Two amplicons were selected to display in greater detail; each differs by only one base from a second target amplicon, yet were specifically discerned within the mixture. Raw data were averaged for triplicates for these two amplicons; reproducibility is demonstrated by the error bars (displayed; one standard deviation from the mean (plotted on log 10 scale). The data are also highly linear; the R2 values are shown on the graph and are 0.998 and 0.997 (linear scale).

The chart in FIG. 14 demonstrates the reproducibility of the assay across the dilution series of amplicon targets. The average, standard deviation, and % CV for four of the amplicon targets at each input concentration (triplicate reactions, raw data) is shown in the table. These four targets are highly representative of the entire population of 20.

Example 5

Assessment of Clinical FFPE Samples for BRAF Mutation Status Using the Disclosed Assay This example describes methods used to assess the BRAF genomic mutation status in a set of commercially-available melanoma formalin-fixed, paraffin embedded (FFPE) samples with known BRAF mutational status.

FFPE samples were lysed in a lysis buffer and 2 mm$^2$ was used per sample. Each sample was run in triplicate. The NPPF and CFSs mixture described in Example 3 was added to the samples. Hybridization was performed in solution at 50° C. overnight after an initial denaturation at 95° C. for 10 minutes.

Following hybridization, S1 digestion was performed on the hybridized mixture by the addition of S1 enzyme in a buffer. The S1 reaction was incubated at 50° C. for 90 minutes. Following S1-mediated digestion of single-stranded nucleic acids (including unhybridized DNA, NPPFs, and CFSs), the reaction was cooled to room temperature. At that point, the reactions were added to 5 µl Dynabeads MyOne C1 Streptavidin paramagnetic beads (ThermoFisher Scientific) at a concentration of 4 µg/µl. Beads and sample mixture were incubated for 30 minutes at room temperature, allowing the biotin moiety on the 3' CFS to be captured by the streptavidin on the beads. This step also serves to stop the S1 reaction.

The beads were washed three time in 150 µl of 1×SSC-T buffer (1×SSC buffer with 0.05% TWEEN® detergent) at room temperature. Washing in this mild buffer allows the hybridized structure to remain intact. Washing was performed by placing the reaction tube on a stand magnet to allow the beads to collect, removing the supernatant, then resuspending the beads in 1×SSC-T.

Washed beads were resuspended in 20 µl of ligation mixture containing 80 units of T4 DNA Ligase and 0.6 units of T4 DNA Polymerase (enzymes and buffer from New England Biolabs). Ligation proceeded for 1 hour at room temperature. Following the ligation reaction, the beads were washed three times with 150 µl of 50% formamide in 0.02% TWEEN® polysorbate 20 detergent. Washing was performed by placing the reaction tube on a stand magnet and allowing the beads to collect, removing the supernatant, then resuspending the beads in wash buffer. These washes denature the double-stranded product and wash away the NPPFs, leaving the ligated target-CFSs complex on the beads. Washed beads were collected a final time and resuspended in 20 µl of 0.02% TWEEN® polysorbate 20 detergent in dH$_2$O.

Part of the reaction described above, which contained ligated cNPPFs of the targets in the sample, was then incubated with PCR primers. These primers were designed as described in Example 2. The experimental tags used are shown in Table 5.

TABLE 5

Exemplary barcode sequences

| 5' primer number | 5' Barcode sequence (5'-3' in primer) | 3' primer number | 3' Barcode sequence (5'-3' in primer) |
|---|---|---|---|
| F1 | TGAACCTT (SEQ ID NO: 28) | R1 | TAGCTT (SEQ ID NO: 55) |
| F2 | CTAATCGA (SEQ ID NO: 29) | R2 | GAGTGG (SEQ ID NO: 56) |
| F3 | ATATATTC (SEQ ID NO: 54) | R3 | TTAGGC (SEQ ID NO: 57) |
|  |  | R4 | ATCACG (SEQ ID NO: 58) |
|  |  | R5 | TGACCA (SEQ ID NO: 34) |
|  |  | R6 | AAGCTA (SEQ ID NO: 52) |
|  |  | R7 | ACTTGA (SEQ ID NO: 53) |
|  |  | R8 | GTAGCC (SEQ ID NO: 59) |

Each reaction was amplified in a separate PCR reaction, and each was amplified with a different combination of experimental tags (one 5' primer and one 3' primer), so each reaction could be separately identified following sequencing of the pooled reactions. Amplification was preceded by a treatment with uracil DNA deglycosylase (UDG) in all reactions. UDG catalyzes the release of free uracil from uracil-containing DNA, including oligonucleotide or single-stranded DNA. In the reactions described, the function of UDG is to destroy any leftover NPPFs present following the previous enzymatic and washing steps. UDG treatment was followed by 22 cycles of PCR.

The resulting amplicons were pooled together and cleaned up using bead-based sample cleanup (AMPure XP from BeckmanCoulter). The amplicons containing the cNPPF and the experimental tags were then sequenced using an ILLUMINA® MiSeq platform. While the experimental tags can be located in several places, in this example, they was located at both sides of the amplicon, immediately downstream of a region complimentary to an index-read sequencing primer. ILLUMINA® sequencing was thus done in three steps, an initial read of the sequence followed by two shorter reads of the experimental tags using two other sequencing primers (all sequencing primers were included in the standard ILLUMINA® kit). The sequencing method described herein and used is a standard method for multiplexing samples on an ILLUMINA® platform.

Each molecule sequenced was sorted based first on the experiment tags, and then within each experiment tag group, the number of molecules identified for each of the different tags was counted. The amplicons were compared to the expected sequences using the open-source software bowtie.

Figure 15:
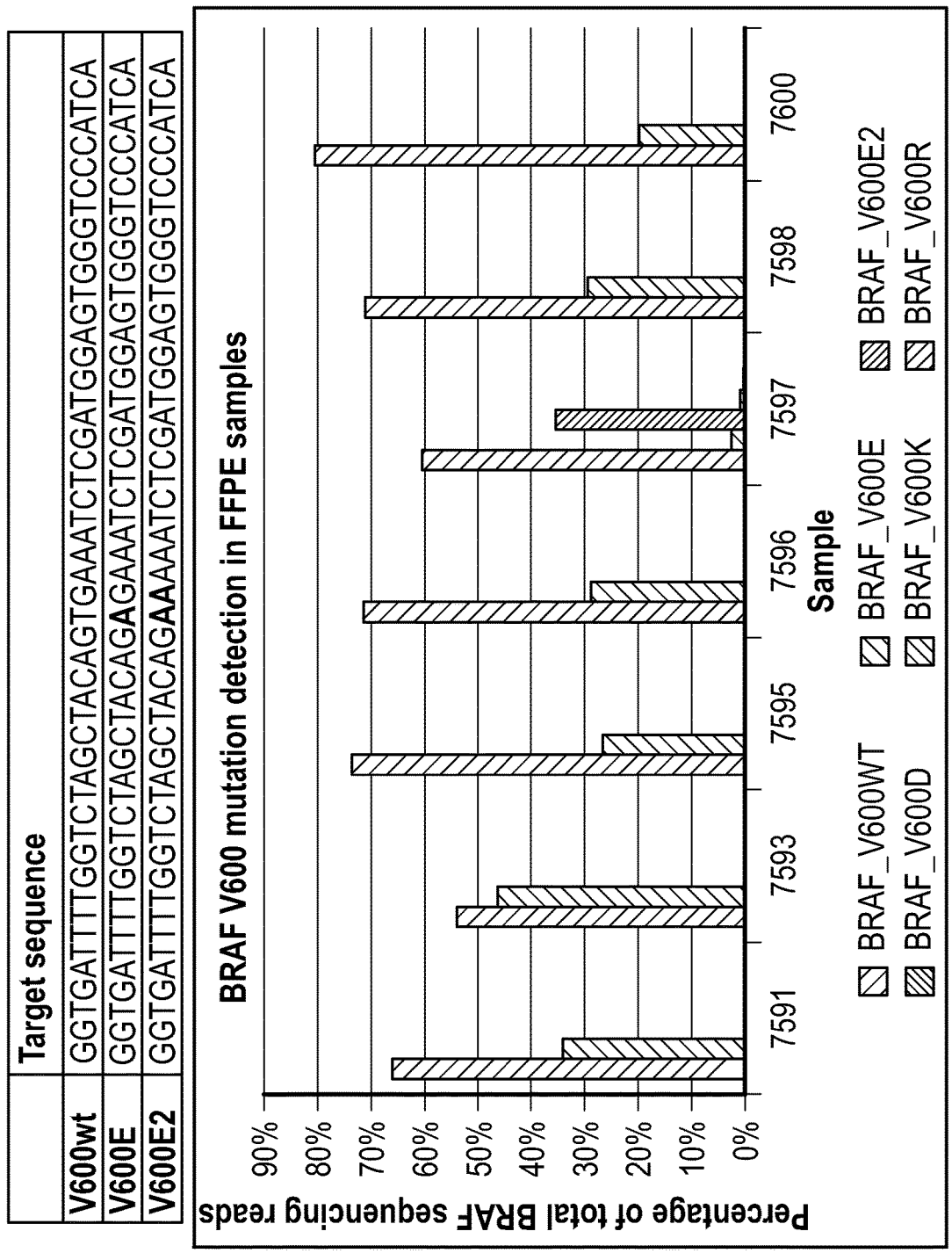
FIG. 15 is a bar graph showing the ability of the disclosed methods to discern nucleotide variations within clinical FFPE samples with known BRAF mutational status. The sequences at the top show the BRAF target sequences (SEQ ID NOS: 62, 63, and 64).

FIG. 15 shows the results from sequencing the ligated targets and CFSs (CNPPFs). The graph was generated by first averaging the raw counts from triplicate samples. The BRAF V600 location was of interest (target sequences shown in FIG. 15 for the wild type locus ("V600w"), the V600E mutation ("V600E") and the V600E2 mutation ("V600E2")). The total number of counts generated from all BRAF V600 signal (wild type and mutant) was summed, and the proportion of wild type or mutant signal for each sample was calculated. These proportions were graphed in FIG. 15.

The data demonstrate the ability to correctly identify the BRAF V600E mutation within these clinical FFPE samples. Although only a single sample carried the V600E2 mutation (sequences shown FIG. 15), the disclosed probe design allowed for differentiation between V600E and V600E2 (the E2 mutation status was unexpected; the samples were designated as BRAF mutant samples but the exact mutation was not described and may not have been known by the vendor). This is demonstrates the ability to uncover unknown mutations using the probe design used in this example (described in Example 3). Additionally, these results were generated using a parsimonious amount (2 mm$^2$) of fixed tissue, demonstrating the ability of the NPPF assay to work using small amounts of clinically-relevant samples.

Example 6

Assessment of RNA Using an NPPF Assay

This example describes methods used to assess RNA expression level quantitation using the disclosed methods, in samples comprising either tissue lysate or isolated RNA.

A set of 33 NPPFs was generated. The design of these NPPFs follows that described in Example 3. Each NPPF included a region that was specific for a particular target nucleic acid molecule 50 nucleotides in length. Each probe also includes a single mismatch relative to the target sequence. Either a C>T or a A>G change was used as the mismatch. For all NPPFs, the 5'- and 3'-flanking sequences were as described in Example 3.

The set of NPPFs was pooled with CFSs complementary to the flanking regions on the NPPFs. The 5'-CFS was an RNA-DNA hybrid oligonucleotide (the three 5'-most nucleotides were RNA bases) and was phosphorylated at the 5' end. The 3'-CFS was an RNA-DNA hybrid oligonucleotide (the three 3' most nucleotides were RNA bases) and carried an internal biotin moiety. Also included in the NPPF and CFSs mixture were two DNA oligonucleotides, 50 bases in length and phosphorylated at the 5' end, that serve as targets for two of the NPPFs in the mixture. As these are DNA and not RNA, they are used in this particular example as nucleotide-specific controls.

Three sample types were utilized. One sample type was an RNA oligo of known sequence, 50 bases in length and phosphorylated on the 5' end. A second sample type was a mixture of six in vitro transcribed RNA sequences, of known sequence, all greater than 50 bases in length. The third sample was a colon cancer tissue sample, homogenized in a lysis buffer. Each sample type was diluted in a lysis buffer and was run in a titration series. The NPPF and CFSs mixture described above was added to the samples. Hybridization was performed in solution at 50° C. overnight after an initial denaturation at 95° C. for 10 minutes.

Following hybridization, S1 digestion was performed on the hybridized mixture by the addition of S1 enzyme in a buffer. The S1 reaction was incubated at 50° C. for 90 minutes. Following S1-mediated digestion of single-stranded nucleic acids (including unhybridized nucleic acids, NPPFs, and CFSs), the reaction was cooled to room temperature. The reactions were added to 5 µl Dynabeads MyOne C1 Streptavidin paramagnetic beads (ThermoFisher Scientific) at a concentration of 4 µg/µl. The beads and sample mixture was incubated for 30 minutes at room temperature, allowing the biotin moiety on the 3' CFS to be captured by the streptavidin on the beads. This step also stops the S1 reaction.

The beads were washed three times in 150 µl of 1×SSC-T buffer (1×SSC buffer with 0.05% TWEEN® polysorbate 20 detergent) at room temperature. Washing in this mild buffer allows the hybridized structure to remain intact. Washing was performed by placing the reaction tube on a stand magnet to allow the beads to collect, removing the supernatant, then resuspending the beads in 1×SSC-T.

Washed beads were resuspended in 20 µl of ligation mixture containing 2 units of T4 RNA Ligase 2 and 0.5 units of *E. coli* RNA Polymerase (both from New England Biolabs). Ligation proceeded for 1 hour at 37° C. Following the ligation reaction, the beads were washed three times with 150 µl of 50% formamide in 0.02% TWEEN® polysorbate 20 detergent at 50° C. Washing was performed by placing the reaction tube on a stand magnet and allowing the beads to collect, removing the supernatant, then resuspending the beads in wash buffer. These washes denature the double-stranded product and wash away the NPPFs, leaving the ligated target-CFSs (CNPPF) complex on the beads. Washed beads were collected in 10 µl of 0.02% TWEEN® polysorbate 20 detergent, and 10 µl of reverse transcription mix was added (containing 200 units of reverse transcriptase (New England Biolabs), buffer, and primer to a final concentration of 500 nM). Reverse transcription was performed at 45° C. for 2 hours. The beads were then washed once in 150 µl of SSC-T and resuspended in 20 µl of 10 mM Tris pH 8.0 with 0.05% TWEEN® polysorbate 20 detergent.

Part of the reaction described above, which contained ligated cNPPFs of the targets in the sample, was then incubated with PCR primers. These primers were designed as described in Example 2. The experimental tags used are shown in Table 6.

TABLE 6

Experiment tags

| 5' primer number | 5' Barcode sequence (5'-3' in primer) | 3' primer number | 3' Barcode sequence (5'-3' in primer) |
|---|---|---|---|
| F1 | GGCTCT (SEQ ID NO: 37) | R1 | ACATCG (SEQ ID NO: 49) |
| F2 | TATAGC (SEQ ID NO: 38) | R2 | ATTGGC (SEQ ID NO: 46) |
| F3 | AGGCGA (SEQ ID NO: 40) | R3 | GATCTG (SEQ ID NO: 60) |
| F4 | TAATCT (SEQ ID NO: 50) | R4 | TTAGGC (SEQ ID NO: 57) |
|  |  | R5 | ACAGTG (SEQ ID NO: 61) |
|  |  | R6 | GCCAAT (SEQ ID NO: 42) |
|  |  | R7 | ACTTGA (SEQ ID NO: 53) |

TABLE 6-continued

Experiment tags

| 5' primer number | 5' Barcode sequence (5'-3' in primer) | 3' primer number | 3' Barcode sequence (5'-3' in primer) |
|---|---|---|---|
|  |  | R8 | CGTACG (SEQ ID NO: 48) |

Each reaction was amplified in a separate PCR reaction, and each was amplified with a different combination of experimental tags (one 5' primer and one 3' primer), to allow each reaction to be separately identified following sequencing of the pooled reactions. Amplification was preceded by a treatment with uracil DNA deglycosylase (UDG) in all reactions. UDG catalyzes the release of free uracil from uracil-containing DNA, including oligonucleotide or single-stranded DNA. In the reactions described, the UDG destroyed any remaining NPPFs present following the previous enzymatic and washing steps. UDG treatment was followed by 24 cycles of PCR.

The resulting amplicons were pooled by sample type and cleaned up using bead-based sample cleanup (AMPure XP from BeckmanCoulter). The amplicons containing the cNPPF and experimental tags were sequenced using an ILLUMINA® MiSeq platform. While the experimental tags can be located in several places, in this example, they was located at both sides of the amplicon, immediately downstream of a region complimentary to an index-read sequencing primer. ILLUMINA® sequencing was thus done in three steps, an initial read of the sequence followed by two shorter reads of the experimental tags using two other sequencing primers (all sequencing primers were included in the standard ILLUMINA® kit). The sequencing method described herein and used is a standard method for multiplexing samples on an ILLUMINA® platform.

Each molecule sequenced was sorted based first on the experiment tags. The sequencing reads thus sorted by tags were compared to the expected sequences using the open-source software bowtie (Langmead et al., Ultrafast and memory-efficient alignment of short DNA sequences to the human genome. *Genome Biol* 10: R25) and a data table constructed for number of molecules sequenced ("counts") per expected sequence per sample.

Figure 16A:
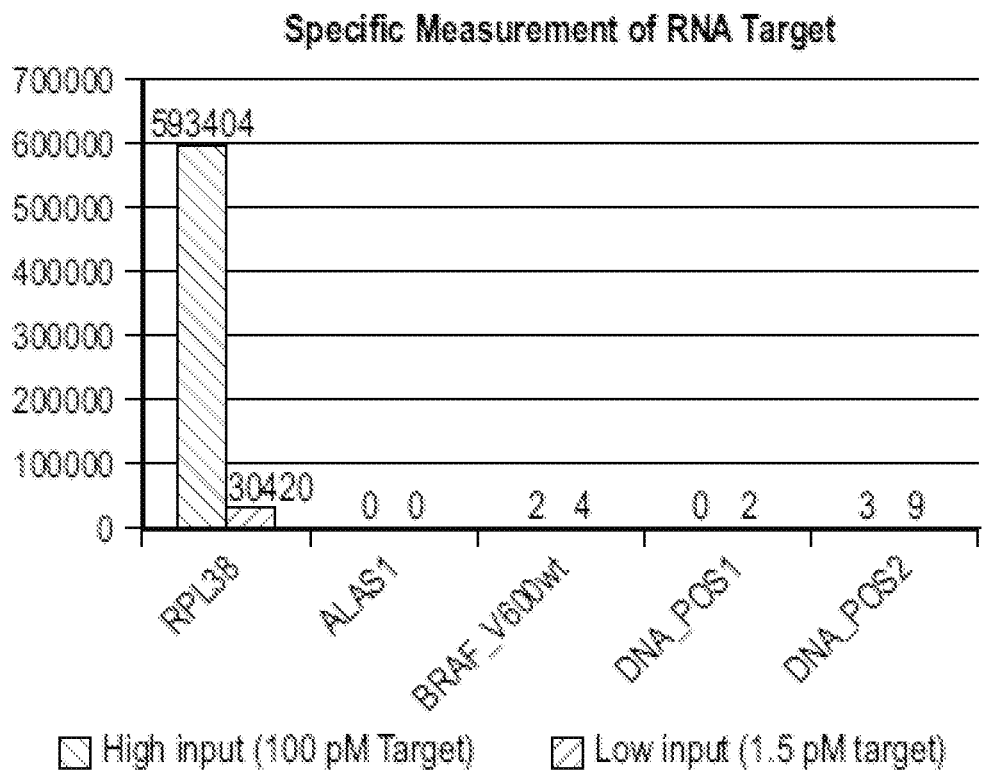
FIGS. 16A-16D are graphs showing the results from sequencing RNA targets using the disclosed methods. Raw sequencing counts are plotted. (A) sequencing counts from a sample containing a specific RNA oligonucleotide. (B) sequencing counts from a set of sample containing a specific RNA oligonucleotide at different concentrations (titration). (C) sequencing counts of three RNA targets present in a sample containing tissue lysate. Four different sample input titrations were tested. (D) sequencing counts of six different RNA targets present in a sample.

FIGS. 16A-16D show the results from sequencing the ligated targets and CFSs (CNPPFs). Raw sequencing counts are plotted. FIG. 16A shows the results for the sample containing a specific RNA oligonucleotide. These results demonstrate the ability of the disclosed methods to measure a specific RNA target. The results also demonstrate that methods correctly measured RNA and not DNA, as the two DNA oligonucleotides ("POST" and "POS2" on the graph) added to the assay were not measured, despite having complementary NPPFs within the assay. This is important, as RNA is transcribed off a DNA strand. If the methods used within this example were not specific for RNA, it would be difficult to identify whether sequencing results were stemming from an RNA or a DNA target. The results also demonstrate that only targets present in the sample are measured, without spurious or background signal ("BRAF_V600E_wt" is shown as an example of the clean background; no BRAF RNA target was present in the sample used). For this specific example, measuring only RNA demonstrated that the methods described herein can be targeted to specifically measure RNA or DNA. However, this does not mean that the methods described herein can only be used to measure one type of nucleic acid (i.e., RNA or DNA) at a given time or in a given assay. DNA and RNA may be co-measured using the methods should a mixed RNA-DNA assay be desirable.

Figure 16B:
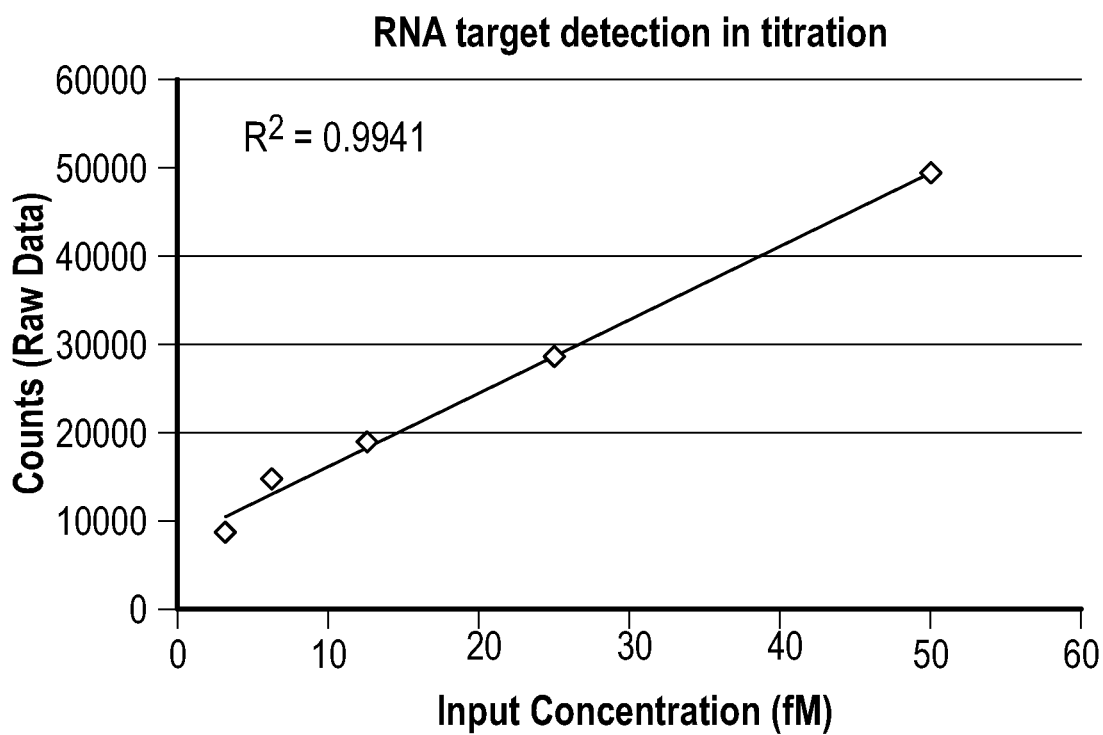

FIG. 16B shows the results from a set of samples containing a specific RNA oligonucleotide over a range of input (titration series). Raw data from a five-point titration of sample input is shown, and the R2 value for the results is 0.9941 (linear scale). This demonstrate good linearity of measurement.

Figure 16C:
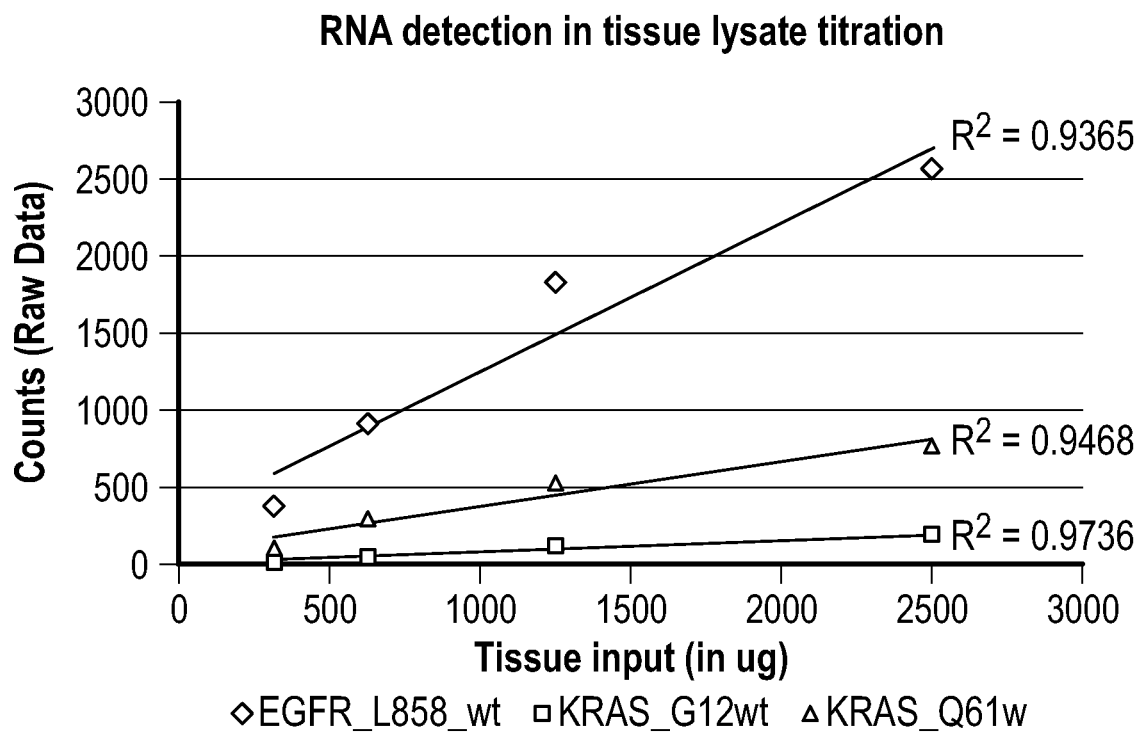

FIG. 16C shows data from a set of samples containing tissue lysate. Three RNA targets are measured over a four-point sample input titration, and the R2 values for all three are at least 0.93, demonstrating excellent linearity across a titration of input in a physiological sample.

Figure 16D:
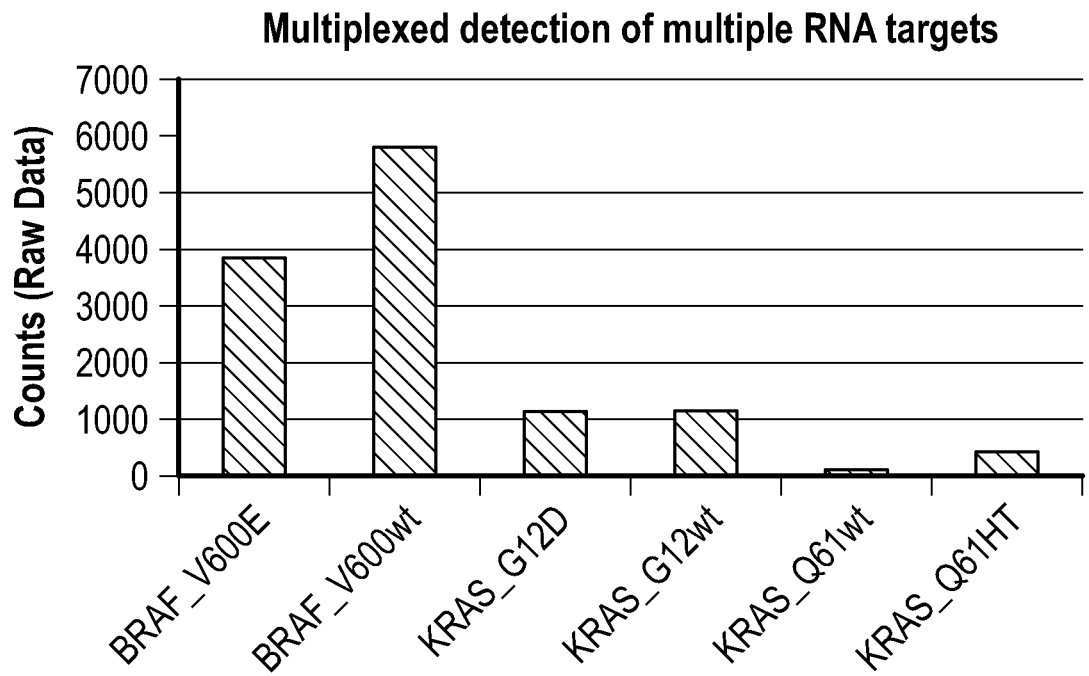

FIG. 16D shows the results from a sample comprised of six in vitro transcripts. All six are correctly and specifically measured as shown by the counts plotted for the six targets. Both FIG. 16C and FIG. 16D demonstrate multiplexed detection of RNA targets in different sample types.

These data demonstrate the ability to specifically and quantitatively measure RNA targets using the methods disclosed herein.

In view of the many possible embodiments to which the principles of the disclosed invention may be applied, it should be recognized that the illustrated embodiments are only examples of the disclosure and should not be taken as limiting the scope of the disclosure. Rather, the scope of the invention is defined by the following claims. We therefore claim as our invention all that comes within the scope and spirit of these claims.

We claim:

1. A method of determining a sequence of a target nucleic acid molecule in a sample, comprising:
contacting the sample with at least one nuclease protection probe comprising a flanking sequence (NPPF) under conditions sufficient for the NPPF to specifically bind to the target nucleic acid molecule,
wherein the NPPF comprises:
a 5'-end and a 3'-end,
a sequence complementary to a region of the target nucleic acid molecule, permitting specific binding between the NPPF and the target nucleic acid molecule,
wherein the flanking sequence is located 5', 3', or both, to the sequence complementary to the target nucleic acid molecule, wherein the 5'-flanking sequence is 5' of the sequence complementary to the target nucleic acid molecule, and the 3'-flanking sequence is 3' of the sequence complementary to the target nucleic acid molecule,
wherein the flanking sequence comprises at least 12 contiguous nucleotides not found in a nucleic acid molecule present in the sample,
if the NPPF comprises a 5'-flanking sequence, contacting the sample with a nucleic acid molecule comprising a sequence complementary to the 5'-flanking sequence (5CFS), a 5'-end phosphate, under conditions sufficient for the 5'-flanking sequence to specifically hybridize to the 5CFS;
if the NPPF comprises a 3'-flanking sequence, contacting the sample with a nucleic acid molecule comprising a sequence complementary to the 3'-flanking sequence (3CFS) under conditions sufficient for the 3'-flanking sequence to specifically hybridize to the 3CFS;
wherein at least one of the 3CFS and the 5CFS comprises a capture moiety;
wherein at least one nucleotide in the NPPF does not have complementarity to the corresponding nucleotide in the target nucleic acid molecule, or does not have complementarity to the corresponding nucleotide in the 5CFS or 3CFS,
generating an NPPF hybridized to the target nucleic acid molecule, hybridized to the 3CFS, hybridized to the 5CFS, or hybridized to both the 3CFS and the 5CFS;
contacting the sample with a nuclease specific for single-stranded nucleic acid molecules under conditions sufficient to remove unbound nucleic acid molecules, thereby generating a digested sample comprising NPPF hybridized to the target nucleic acid molecule, hybridized to the 3CFS, hybridized to the 5CFS, or hybridized to both the 3CFS and the 5CFS;
capturing the NPPF hybridized to the target nucleic acid molecule, hybridized to the 3CFS, hybridized to the 5CFS, or hybridized to both the 3CFS and the 5CFS;
ligating the 5'-phosphate of the 3CFS to a 3'-end of the target nucleic acid molecule, and ligating a 3'-end of the 5CFS to a 5'-end of the target nucleic acid molecule, thereby generating a ligated target nucleic acid molecule;
separating the NPPF from the ligated target nucleic acid molecule, thereby generating a mixture comprising single stranded NPPF and single stranded ligated target nucleic acid molecule; and
sequencing at least a portion of the single stranded ligated target nucleic acid molecule, thereby determining the sequence of the at least one target nucleic acid molecule in the sample.

2. The method of claim 1, wherein the NPPF comprises at least one dUTP, and the method further comprises contacting the mixture comprising single stranded NPPF and single stranded ligated target nucleic acid molecule with uracil DNA deglycosylase (UDG) under conditions sufficient for degrading the single stranded NPPF, after the denaturing and before the sequencing.

3. The method of claim 2, wherein the at least one dUTP is located within 5 base pairs of the sequence complementary to a region of the target nucleic acid molecule.

4. The method of claim 1, wherein the NPPF comprises both a 5'-flanking sequence and a 3'-flanking sequence, and the method further comprises after the denaturing and before the sequencing,
contacting the single stranded ligated target nucleic acid molecule with a first amplification primer comprising a region that is complementary to the 3CFS and with a second amplification primer comprising a region that is complementary to the 5CFS; and
amplifying the single stranded ligated target nucleic acid molecule with the first and second amplification primers.

5. The method of claim 4, further comprising removing the first and second amplification primers after the amplifying and prior to the sequencing.

6. The method of claim 4, wherein
the first and/or the second amplification primer further comprises a sequence that permits attachment of an experimental tag or sequencing adaptor to the single stranded ligated target nucleic acid molecule during the amplification step, or
the first amplification primer further comprises a sequence that permits attachment of a first experiment tag and/or a first sequencing adaptor to the 5'-end of the single stranded ligated target nucleic acid molecule during the amplification step, and wherein the second amplification primer further comprises a sequence that permits attachment of a second experiment tag and/or a second sequencing adaptor to the 3'-end of the single stranded ligated target nucleic acid molecule during the amplification step.

7. The method of claim 6, wherein the experiment tag comprises a nucleic acid sequence that permits identification of a sample, subject, treatment or target nucleic acid sequence.

8. The method of claim 6, wherein the sequencing adaptor comprises a nucleic acid sequence that permits capture onto a sequencing platform.

9. The method of claim 6, wherein the experiment tag or sequence adaptor is present on the 5'-end or 3'-end of the single stranded ligated target nucleic acid molecule.

10. The method of claim 1, wherein the NPPF comprises both a 5'-flanking sequence and a 3'-flanking sequence, wherein at least one flanking sequence comprises at least one dUTP, and the method further comprises after the denaturing and before the sequencing:
   washing the mixture comprising single stranded NPPF and single stranded ligated target nucleic acid molecule comprising contacting the mixture with a surface that can bind to the capture moiety and removing undesired agents;
   contacting the mixture comprising single stranded NPPF and single stranded ligated target nucleic acid molecule with uracil DNA deglycosylase (UDG) under conditions sufficient for degrading the single stranded NPPF;
   contacting the single stranded ligated target nucleic acid molecule with a first amplification primer comprising a region that is complementary to the 3CFS and with a second amplification primer comprising a region that is complementary to the 5CFS; and
   amplifying the ligated target nucleic acid molecule with the first and second amplification primers.

11. The method of claim 1, wherein the at least one target nucleic acid molecule is
   DNA, and wherein the 5CFS and the 3CFS are DNA;
   DNA, and wherein the 5CFS is DNA and the 3CFS is RNA;
   RNA, and wherein the 5CFS is DNA and the 3CFS is RNA; or
   RNA, and wherein the 5CFS is RNA and the 3CFS is RNA.

12. The method any of claim 1, wherein the NPPF comprises a DNA molecule.

13. The method of claim 1, wherein the NPPF comprises 35-150 nucleotides.

14. The method of claim 1, wherein the sequence complementary to a region of the target nucleic acid molecule is 10-60 nucleotides in length.

15. The method of claim 1, wherein the flanking sequence is 12 to 50 nucleotides in length.

16. The method of claim 1, wherein the NPPF comprises a flanking sequence at the 5'-end and the 3'-end, wherein the flanking sequence at the 5'-end differs from the flanking sequence at the 3'-end.

17. The method of claim 1, wherein the capture moiety comprises a solid support or a label.

18. The method of claim 1, wherein the at least one target nucleic acid molecule is fixed, cross-linked, or insoluble.

19. The method of claim 1, wherein the NPPF is a DNA and the nuclease comprises an exonuclease, an endonuclease, or a combination thereof.

20. The method of claim 1, wherein the nuclease specific for single-stranded nucleic acid molecules comprises S1 nuclease.

21. The method of claim 1, wherein the method sequences or detects one or more target nucleic acid molecules in a plurality of samples simultaneously.

22. The method of claim 1, wherein the method sequences or detects at least two target nucleic acid molecules, and wherein the sample is contacted with at least two different NPPFs, each NPPF specific for a different target nucleic acid molecule.

23. The method of claim 1, wherein the method sequences or detects at least two different target nucleic acid molecules, and wherein the sample is contacted with at least one NPPF specific for the at least two different target nucleic acid molecules.

24. The method of claim 23, wherein the at least two different target nucleic acid molecules comprise a wild type gene sequence and at least one mutation in the gene sequence.

25. The method of claim 1, wherein the method is performed on a plurality of samples and at least two different target nucleic acid molecules are detected in each of the plurality of samples.

26. The method of claim 1, wherein at least one NPPF is specific for a miRNA target nucleic acid molecule and at least one NPPF is specific for an mRNA target nucleic acid molecule.

27. The method of claim 1, further comprising lysing the sample.

28. The method of claim 1, wherein determining the sequence of the target nucleic acid molecule determines if the target nucleic acid molecule comprises a point mutation.

29. The method of claim 1, wherein the method further includes polymerizing the captured target nucleic acid molecule at the same time as the ligation step, or prior to the ligation step.

* * * * *

```
                         SEQUENCE LISTING

<160> NUMBER OF SEQ ID NOS: 64

<210> SEQ ID NO 1
<211> LENGTH: 50
<212> TYPE: DNA
<213> ORGANISM: Artificial Sequence
<220> FEATURE:
<223> OTHER INFORMATION: NPPF to detect BRAF targets
<220> FEATURE:
<221> NAME/KEY: misc_feature
<222> LOCATION: (14)..(14)
<223> OTHER INFORMATION: n is dUTP
<220> FEATURE:
<221> NAME/KEY: misc_feature
<222> LOCATION: (36)..(36)
<223> OTHER INFORMATION: n is dUTP

<400> SEQUENCE: 1
tgatgggacc cgcnccatcg agatttcact gtagcnagac caaaatcacc            50

<210> SEQ ID NO 2
<211> LENGTH: 50
<212> TYPE: DNA
<213> ORGANISM: Homo sapiens

<400> SEQUENCE: 2
tgatgggacc cactccatcg agatttcact gtagctagac caaaatcacc            50

<210> SEQ ID NO 3
<211> LENGTH: 50
<212> TYPE: DNA
<213> ORGANISM: Homo sapiens

<400> SEQUENCE: 3
tgatgggacc cactccatcg agatttctct gtagctagac caaaatcacc            50

<210> SEQ ID NO 4
<211> LENGTH: 50
<212> TYPE: DNA
<213> ORGANISM: Homo sapiens

<400> SEQUENCE: 4
tgatgggacc cactccatcg agatttcttt gtagctagac caaaatcacc            50

<210> SEQ ID NO 5
<211> LENGTH: 50
<212> TYPE: DNA
<213> ORGANISM: Homo sapiens
```

<400> SEQUENCE: 5
tgatgggacc cactccatcg agatttcctt gtagctagac caaaatcacc          50

<210> SEQ ID NO 6
<211> LENGTH: 50
<212> TYPE: DNA
<213> ORGANISM: Homo sapiens

<400> SEQUENCE: 6
tgatgggacc cactccatcg agatttttct gtagctagac caaaatcacc          50

<210> SEQ ID NO 7
<211> LENGTH: 50
<212> TYPE: DNA
<213> ORGANISM: Homo sapiens

<400> SEQUENCE: 7
tgatgggacc cactccatcg agatttatct gtagctagac caaaatcacc          50

<210> SEQ ID NO 8
<211> LENGTH: 50
<212> TYPE: DNA
<213> ORGANISM: Artificial Sequence
<220> FEATURE:
<223> OTHER INFORMATION: NPPF to detect KRAS at amino acid 12
<220> FEATURE:
<221> NAME/KEY: misc_feature
<222> LOCATION: (17)..(17)
<223> OTHER INFORMATION: n is dUTP
<220> FEATURE:
<221> NAME/KEY: misc_feature
<222> LOCATION: (36)..(36)
<223> OTHER INFORMATION: n is dUTP

<400> SEQUENCE: 8
tgtatcgtca aggcgcnctt gcctacgcca ccagcnccaa ctaccacaag          50

<210> SEQ ID NO 9
<211> LENGTH: 50
<212> TYPE: DNA
<213> ORGANISM: Homo sapiens

<400> SEQUENCE: 9
tgtatcgtca aggcactctt gcctacgcca ccagctccaa ctaccacaag          50

<210> SEQ ID NO 10
<211> LENGTH: 50
<212> TYPE: DNA
<213> ORGANISM: Homo sapiens

<400> SEQUENCE: 10
tgtatcgtca aggcactctt gcctacgcca tcagctccaa ctaccacaag          50

<210> SEQ ID NO 11
<211> LENGTH: 50
<212> TYPE: DNA
<213> ORGANISM: Homo sapiens

<400> SEQUENCE: 11
tgtatcgtca aggcactctt gcctacgcca acagctccaa ctaccacaag          50

<210> SEQ ID NO 12
<211> LENGTH: 50
<212> TYPE: DNA
<213> ORGANISM: Homo sapiens -continued

<400> SEQUENCE: 12
tgtatcgtca aggcactctt gcctacgcca gcagctccaa ctaccacaag            50

<210> SEQ ID NO 13
<211> LENGTH: 50
<212> TYPE: DNA
<213> ORGANISM: Homo sapiens

<400> SEQUENCE: 13
tgtatcgtca aggcactctt gcctacgcca caagctccaa ctaccacaag            50

<210> SEQ ID NO 14
<211> LENGTH: 50
<212> TYPE: DNA
<213> ORGANISM: Homo sapiens

<400> SEQUENCE: 14
tgtatcgtca aggcactctt gcctacgcca ctagctccaa ctaccacaag            50

<210> SEQ ID NO 15
<211> LENGTH: 50
<212> TYPE: DNA
<213> ORGANISM: Homo sapiens

<400> SEQUENCE: 15
tgtatcgtca aggcactctt gcctacgcca cgagctccaa ctaccacaag            50

<210> SEQ ID NO 16
<211> LENGTH: 50
<212> TYPE: DNA
<213> ORGANISM: Homo sapiens

<400> SEQUENCE: 16
tgtatcgtca aggcactctt gcctacgtca ccagctccaa ctaccacaag            50

<210> SEQ ID NO 17
<211> LENGTH: 50
<212> TYPE: DNA
<213> ORGANISM: Artificial Sequence
<220> FEATURE:
<223> OTHER INFORMATION: NPPF to detect KRAS coding sequence at amino
      acid 61
<220> FEATURE:
<221> NAME/KEY: misc_feature
<222> LOCATION: (16)..(16)
<223> OTHER INFORMATION: n is dUTP
<220> FEATURE:
<221> NAME/KEY: misc_feature
<222> LOCATION: (37)..(37)
<223> OTHER INFORMATION: n is dUTP

<400> SEQUENCE: 17
ggtccctcat tgtacngtac tcctcttgac ctgctgngtc gagaatatcc            50

<210> SEQ ID NO 18
<211> LENGTH: 50
<212> TYPE: DNA
<213> ORGANISM: Homo sapiens

<400> SEQUENCE: 18
ggtccctcat tgcactgtac tcctcttgac ctgctgtgtc gagaatatcc            50

<210> SEQ ID NO 19
<211> LENGTH: 50

```
<212> TYPE: DNA
<213> ORGANISM: Homo sapiens

<400> SEQUENCE: 19
ggtccctcat tgcactgtac tcctcttcac ctgctgtgtc gagaatatcc            50

<210> SEQ ID NO 20
<211> LENGTH: 50
<212> TYPE: DNA
<213> ORGANISM: Homo sapiens

<400> SEQUENCE: 20
ggtccctcat tgcactgtac tcctctcgac ctgctgtgtc gagaatatcc            50

<210> SEQ ID NO 21
<211> LENGTH: 50
<212> TYPE: DNA
<213> ORGANISM: Homo sapiens

<400> SEQUENCE: 21
ggtccctcat tgcactgtac tcctctagac ctgctgtgtc gagaatatcc            50

<210> SEQ ID NO 22
<211> LENGTH: 50
<212> TYPE: DNA
<213> ORGANISM: Homo sapiens

<400> SEQUENCE: 22
ggtccctcat tgcactgtac tcctcgtgac ctgctgtgtc gagaatatcc            50

<210> SEQ ID NO 23
<211> LENGTH: 50
<212> TYPE: DNA
<213> ORGANISM: Homo sapiens

<400> SEQUENCE: 23
ggtccctcat tgcactgtac tcctcatgac ctgctgtgtc gagaatatcc            50

<210> SEQ ID NO 24
<211> LENGTH: 25
<212> TYPE: DNA
<213> ORGANISM: Artificial Sequence
<220> FEATURE:
<223> OTHER INFORMATION: 5' flanking sequence
<220> FEATURE:
<221> NAME/KEY: misc_feature
<222> LOCATION: (23)..(23)
<223> OTHER INFORMATION: n is dUTP

<400> SEQUENCE: 24
tccctacacg acgctcttcc ganct                                       25

<210> SEQ ID NO 25
<211> LENGTH: 25
<212> TYPE: DNA
<213> ORGANISM: Artificial Sequence
<220> FEATURE:
<223> OTHER INFORMATION: 3' flanking sequence
<220> FEATURE:
<221> NAME/KEY: misc_feature
<222> LOCATION: (3)..(3)
<223> OTHER INFORMATION: n is dUTP

<400> SEQUENCE: 25
gancggaaga gcacacgtct gaact                                       25
```

<210> SEQ ID NO 26
<211> LENGTH: 66
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (30)..(37)
<223> OTHER INFORMATION: the n from nucleotide 30 to 37 can be any of
      SEQ ID NOS: 28, 29, 36, 37, 38, 39, 40, 50, 51, or 54
<220> FEATURE:
<221> NAME/KEY: misc_feature
<222> LOCATION: (30)..(37)
<223> OTHER INFORMATION: the eight n from nucleotides 30 to 37 can be
      any of SEQ ID NOS: 28, 29, 36, 37, 38, 39, 40, 50, 51, or 54

<400> SEQUENCE: 26
aatgatacgg cgaccaccga gatctacacn nnnnnnnaca ctctttccct acacgacgct    60
cttccg                                                              66

<210> SEQ ID NO 27
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(30)
<223> OTHER INFORMATION: the 6 n from nucleotides 25 to 30 can be any of
      SEQ ID NOS: 30, 31, 32, 33, 34, 35, 41, 42, 43, 44, 45, 46, 47,
      48, 49, 52, 53, 55, 56, 57, 58, 59, 60 or 61

<400> SEQUENCE: 27
caagcagaag acggcatacg agatnnnnnn gtgactggag ttcagacgtg tgctcttccg    60

<210> SEQ ID NO 28
<211> LENGTH: 8
<212> TYPE: DNA
<213> ORGANISM: Artificial Sequence
<220> FEATURE:
<223> OTHER INFORMATION: experimental tag

<400> SEQUENCE: 28 tgaacctt                                                             8

<210> SEQ ID NO 29
<211> LENGTH: 8
<212> TYPE: DNA
<213> ORGANISM: Artificial Sequence
<220> FEATURE:
<223> OTHER INFORMATION: experimental tag

<400> SEQUENCE: 29 ctaatcga                                                             8

<210> SEQ ID NO 30
<211> LENGTH: 6
<212> TYPE: DNA
<213> ORGANISM: Artificial Sequence
<220> FEATURE:
<223> OTHER INFORMATION: experimental tag

<400> SEQUENCE: 30 gcctaa                                                               6

```
<210> SEQ ID NO 31
<211> LENGTH: 6
<212> TYPE: DNA
<213> ORGANISM: Artificial Sequence
<220> FEATURE:
<223> OTHER INFORMATION: experimental tag

<400> SEQUENCE: 31 cgtgat                                                                  6

<210> SEQ ID NO 32
<211> LENGTH: 6
<212> TYPE: DNA
<213> ORGANISM: Artificial Sequence
<220> FEATURE:
<223> OTHER INFORMATION: experimental tag

<400> SEQUENCE: 32 ggctac                                                                  6

<210> SEQ ID NO 33
<211> LENGTH: 6
<212> TYPE: DNA
<213> ORGANISM: Artificial Sequence
<220> FEATURE:
<223> OTHER INFORMATION: experimental tag

<400> SEQUENCE: 33 ctgatc                                                                  6

<210> SEQ ID NO 34
<211> LENGTH: 6
<212> TYPE: DNA
<213> ORGANISM: Artificial Sequence
<220> FEATURE:
<223> OTHER INFORMATION: experimental tag

<400> SEQUENCE: 34 tgacca                                                                  6

<210> SEQ ID NO 35
<211> LENGTH: 6
<212> TYPE: DNA
<213> ORGANISM: Artificial Sequence
<220> FEATURE:
<223> OTHER INFORMATION: experimental tag

<400> SEQUENCE: 35 cttgta                                                                  6

<210> SEQ ID NO 36
<211> LENGTH: 8
<212> TYPE: DNA
<213> ORGANISM: Artificial Sequence
<220> FEATURE:
<223> OTHER INFORMATION: experimental tag

<400> SEQUENCE: 36 atagaggc                                                                8

<210> SEQ ID NO 37
<211> LENGTH: 8
<212> TYPE: DNA
<213> ORGANISM: Artificial Sequence
<220> FEATURE:
<223> OTHER INFORMATION: experimental tag
```

```
<400> SEQUENCE: 37 ggctctga                                                                 8

<210> SEQ ID NO 38
<211> LENGTH: 8
<212> TYPE: DNA
<213> ORGANISM: Artificial Sequence
<220> FEATURE:
<223> OTHER INFORMATION: experimental tag

<400> SEQUENCE: 38 tatagcct                                                                 8

<210> SEQ ID NO 39
<211> LENGTH: 8
<212> TYPE: DNA
<213> ORGANISM: Artificial Sequence
<220> FEATURE:
<223> OTHER INFORMATION: experimental tag

<400> SEQUENCE: 39 cctatcct                                                                 8

<210> SEQ ID NO 40
<211> LENGTH: 8
<212> TYPE: DNA
<213> ORGANISM: Artificial Sequence
<220> FEATURE:
<223> OTHER INFORMATION: experimental tag

<400> SEQUENCE: 40 aggcgaag                                                                 8

<210> SEQ ID NO 41
<211> LENGTH: 6
<212> TYPE: DNA
<213> ORGANISM: Artificial Sequence
<220> FEATURE:
<223> OTHER INFORMATION: experimental tag

<400> SEQUENCE: 41 cgatgt                                                                   6

<210> SEQ ID NO 42
<211> LENGTH: 6
<212> TYPE: DNA
<213> ORGANISM: Artificial Sequence
<220> FEATURE:
<223> OTHER INFORMATION: experimental tag

<400> SEQUENCE: 42 gccaat                                                                   6

<210> SEQ ID NO 43
<211> LENGTH: 6
<212> TYPE: DNA
<213> ORGANISM: Artificial Sequence
<220> FEATURE:
<223> OTHER INFORMATION: experimental tag

<400> SEQUENCE: 43 cagatc                                                                   6

<210> SEQ ID NO 44
<211> LENGTH: 6
```

```
<212> TYPE: DNA
<213> ORGANISM: Artificial Sequence
<220> FEATURE:
<223> OTHER INFORMATION: experimental tag

<400> SEQUENCE: 44 gcctaa                                                                   6

<210> SEQ ID NO 45
<211> LENGTH: 6
<212> TYPE: DNA
<213> ORGANISM: Artificial Sequence
<220> FEATURE:
<223> OTHER INFORMATION: experimental tag

<400> SEQUENCE: 45 cactgt                                                                   6

<210> SEQ ID NO 46
<211> LENGTH: 6
<212> TYPE: DNA
<213> ORGANISM: Artificial Sequence
<220> FEATURE:
<223> OTHER INFORMATION: experimental tag

<400> SEQUENCE: 46 attggc                                                                   6

<210> SEQ ID NO 47
<211> LENGTH: 6
<212> TYPE: DNA
<213> ORGANISM: Artificial Sequence
<220> FEATURE:
<223> OTHER INFORMATION: experimental tag

<400> SEQUENCE: 47 tcaagt                                                                   6

<210> SEQ ID NO 48
<211> LENGTH: 6
<212> TYPE: DNA
<213> ORGANISM: Artificial Sequence
<220> FEATURE:
<223> OTHER INFORMATION: experimental tag

<400> SEQUENCE: 48 cgtacg                                                                   6

<210> SEQ ID NO 49
<211> LENGTH: 6
<212> TYPE: DNA
<213> ORGANISM: Artificial Sequence
<220> FEATURE:
<223> OTHER INFORMATION: experimental tag

<400> SEQUENCE: 49 acatcg                                                                   6

<210> SEQ ID NO 50
<211> LENGTH: 8
<212> TYPE: DNA
<213> ORGANISM: Artificial Sequence
<220> FEATURE:
<223> OTHER INFORMATION: experimental tag
```

```
<400> SEQUENCE: 50 taatctta                                                                        8

<210> SEQ ID NO 51
<211> LENGTH: 8
<212> TYPE: DNA
<213> ORGANISM: Artificial Sequence
<220> FEATURE:
<223> OTHER INFORMATION: experimental tag

<400> SEQUENCE: 51 caggacgt                                                                        8

<210> SEQ ID NO 52
<211> LENGTH: 6
<212> TYPE: DNA
<213> ORGANISM: Artificial Sequence
<220> FEATURE:
<223> OTHER INFORMATION: experimental tag

<400> SEQUENCE: 52 aagcta                                                                          6

<210> SEQ ID NO 53
<211> LENGTH: 6
<212> TYPE: DNA
<213> ORGANISM: Artificial Sequence
<220> FEATURE:
<223> OTHER INFORMATION: experimental tag

<400> SEQUENCE: 53 acttga                                                                          6

<210> SEQ ID NO 54
<211> LENGTH: 8
<212> TYPE: DNA
<213> ORGANISM: Artificial Sequence
<220> FEATURE:
<223> OTHER INFORMATION: experimental tag

<400> SEQUENCE: 54 atatattc                                                                        8

<210> SEQ ID NO 55
<211> LENGTH: 6
<212> TYPE: DNA
<213> ORGANISM: Artificial Sequence
<220> FEATURE:
<223> OTHER INFORMATION: experimental tag

<400> SEQUENCE: 55 tagctt                                                                          6

<210> SEQ ID NO 56
<211> LENGTH: 6
<212> TYPE: DNA
<213> ORGANISM: Artificial Sequence
<220> FEATURE:
<223> OTHER INFORMATION: experimental tag

<400> SEQUENCE: 56 gagtgg                                                                          6

<210> SEQ ID NO 57
```

```
<211> LENGTH: 6
<212> TYPE: DNA
<213> ORGANISM: Artificial Sequence
<220> FEATURE:
<223> OTHER INFORMATION: experimental tag

<400> SEQUENCE: 57 ttaggc                                                                    6

<210> SEQ ID NO 58
<211> LENGTH: 6
<212> TYPE: DNA
<213> ORGANISM: Artificial Sequence
<220> FEATURE:
<223> OTHER INFORMATION: experimental tag

<400> SEQUENCE: 58 atcacg                                                                    6

<210> SEQ ID NO 59
<211> LENGTH: 6
<212> TYPE: DNA
<213> ORGANISM: Artificial Sequence
<220> FEATURE:
<223> OTHER INFORMATION: experimental tag

<400> SEQUENCE: 59 gtagcc                                                                    6

<210> SEQ ID NO 60
<211> LENGTH: 6
<212> TYPE: DNA
<213> ORGANISM: Artificial Sequence
<220> FEATURE:
<223> OTHER INFORMATION: experimental tag

<400> SEQUENCE: 60 gatctg                                                                    6

<210> SEQ ID NO 61
<211> LENGTH: 6
<212> TYPE: DNA
<213> ORGANISM: Artificial Sequence
<220> FEATURE:
<223> OTHER INFORMATION: experimental tag

<400> SEQUENCE: 61 acagtg                                                                    6

<210> SEQ ID NO 62
<211> LENGTH: 50
<212> TYPE: DNA
<213> ORGANISM: Homo sapiens

<400> SEQUENCE: 62
ggtgattttg gtctagctac agtgaaatct cgatggagtg ggtcccatca                   50

<210> SEQ ID NO 63
<211> LENGTH: 50
<212> TYPE: DNA
<213> ORGANISM: Homo sapiens

<400> SEQUENCE: 63
ggtgattttg gtctagctac agagaaatct cgatggagtg ggtcccatca                   50
```

-continued

```
<210> SEQ ID NO 64
<211> LENGTH: 50
<212> TYPE: DNA
<213> ORGANISM: Homo sapiens

<400> SEQUENCE: 64
ggtgattttg gtctagctac agaaaaatct cgatggagtg ggtcccatca           50
```